(12) United States Patent
Nam et al.

(10) Patent No.: US 9,737,588 B2
(45) Date of Patent: Aug. 22, 2017

(54) METHOD FOR TREATING ARTHRITIS USING IK FACTOR OR NUCLEIC ACID ENCODING IK FACTOR

(71) Applicants: CATHOLIC UNIVERSITY INDUSTRY ACADEMIC COOPERATION FOUNDATION, Seoul (KR); CELLINBIO CO., LTD, Gyeonggi-do (KR)

(72) Inventors: Jae-Hwan Nam, Gyeonggi-do (KR); Hye-Lim Park, Gangwon-do (KR); Dong-Hee Lee, Gyeonggi-do (KR)

(73) Assignees: CELLINBIO CO., LTD, Seoul (KR); CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/784,614

(22) PCT Filed: Apr. 16, 2014

(86) PCT No.: PCT/KR2014/003282
§ 371 (c)(1),
(2) Date: Oct. 15, 2015

(87) PCT Pub. No.: WO2014/171721
PCT Pub. Date: Oct. 23, 2014

(65) Prior Publication Data
US 2016/0058836 A1 Mar. 3, 2016

(30) Foreign Application Priority Data

Apr. 16, 2013 (KR) .................. 10-2013-0041771
Apr. 1, 2014 (KR) .................. 10-2014-0038809

(51) Int. Cl.
*A61K 38/19* (2006.01)
*A61K 48/00* (2006.01)
*A01K 67/027* (2006.01)
*A61K 38/21* (2006.01)

(52) U.S. Cl.
CPC .......... *A61K 38/19* (2013.01); *A01K 67/0275* (2013.01); *A61K 48/005* (2013.01); *A01K 2217/056* (2013.01); *A01K 2217/15* (2013.01); *A01K 2227/105* (2013.01); *A01K 2267/0325* (2013.01); *C12N 2750/14143* (2013.01)

(58) Field of Classification Search
None
See application file for complete search history.

(56) References Cited

FOREIGN PATENT DOCUMENTS

KR   10-2002-0034185 A   5/2002
KR   10-2004-0031031 A   4/2004

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Viral immunology, Feb. 14, 2013 vol. 26, pp. 13-24, Park et al.
The Journal of Immunology, 2002. vol. 169, pp. 6625-6633.
NCBI Reference Sequence: NM_011879.2, (Jan. 6, 2013).
GenBank Accession No. NP_036009, (Aug. 15, 2012).
Masatake Muraoka. IK Cytokine Ameliorates the Progression of Lupus Nephritis in MRL/lpr Mice. Arthritis & Rheumatism. 2006, vol. 54, No. 11, pp. 3591-3600.
Takahiro Okabe. Detection of gene expression in synovium of patients with osteoarthritis using a random sequencing method. Acta Orthopaedica. 2007, vol. 78, No. 5, pp. 687-692.
English translation of the International Search Report, ISA/KR, PCT/KR2014/003282, Jul. 3, 2014.
Office Action, KR 10-2014-0038809, (Sep. 30, 2015).

* cited by examiner

*Primary Examiner* — Bridget E Bunner
*Assistant Examiner* — Fozia Hamud
(74) *Attorney, Agent, or Firm* — Faegre Baker Daniels LLP

(57) ABSTRACT

The present invention relates to a pharmaceutical composition for treating and/or preventing arthritis, which comprising, as an active ingredient, a gene delivery vehicle into which an IK factor or a fragment thereof, or a nucleic acid encoding thereof is inserted. IK factor or the fragment thereof, and the nucleic acid encoding thereof, which are the active ingredient of the pharmaceutical composition according to the present invention, are derived from an organism and therefore, show no side effects in administered into a subject for a long time. Accordingly, they ensures safety and are expected to effectively treat arthritis by being involved in the upstream mechanism for suppressing arthritis.

3 Claims, 16 Drawing Sheets

[FIG. 1]
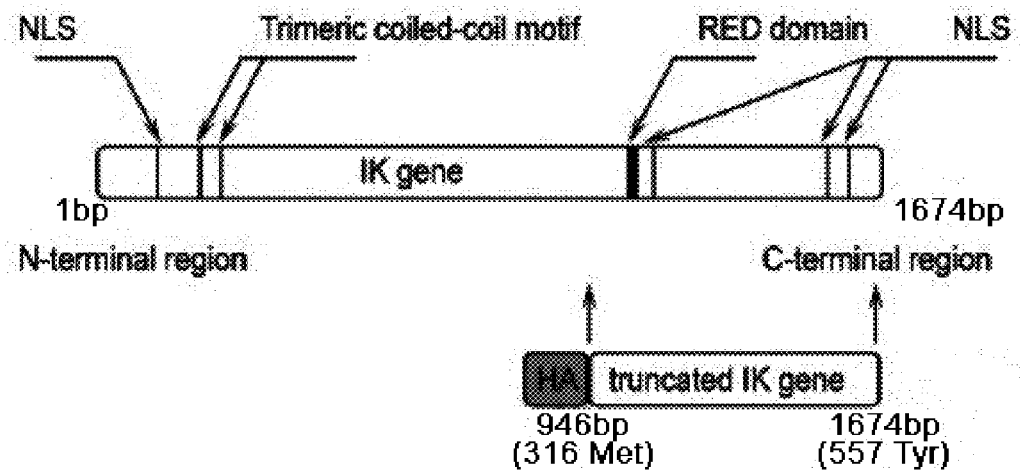
[FIG. 2]
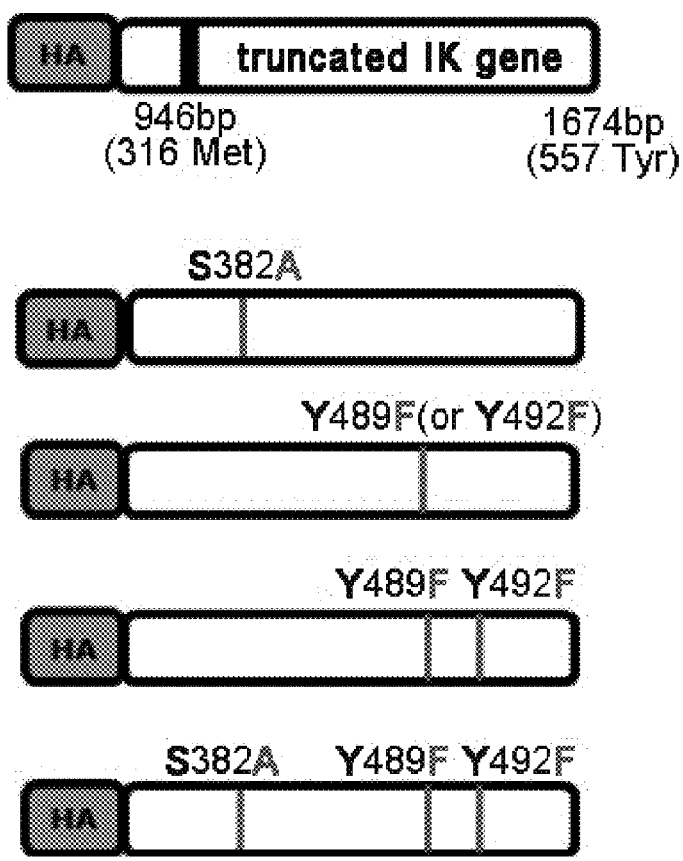

[FIG. 3]
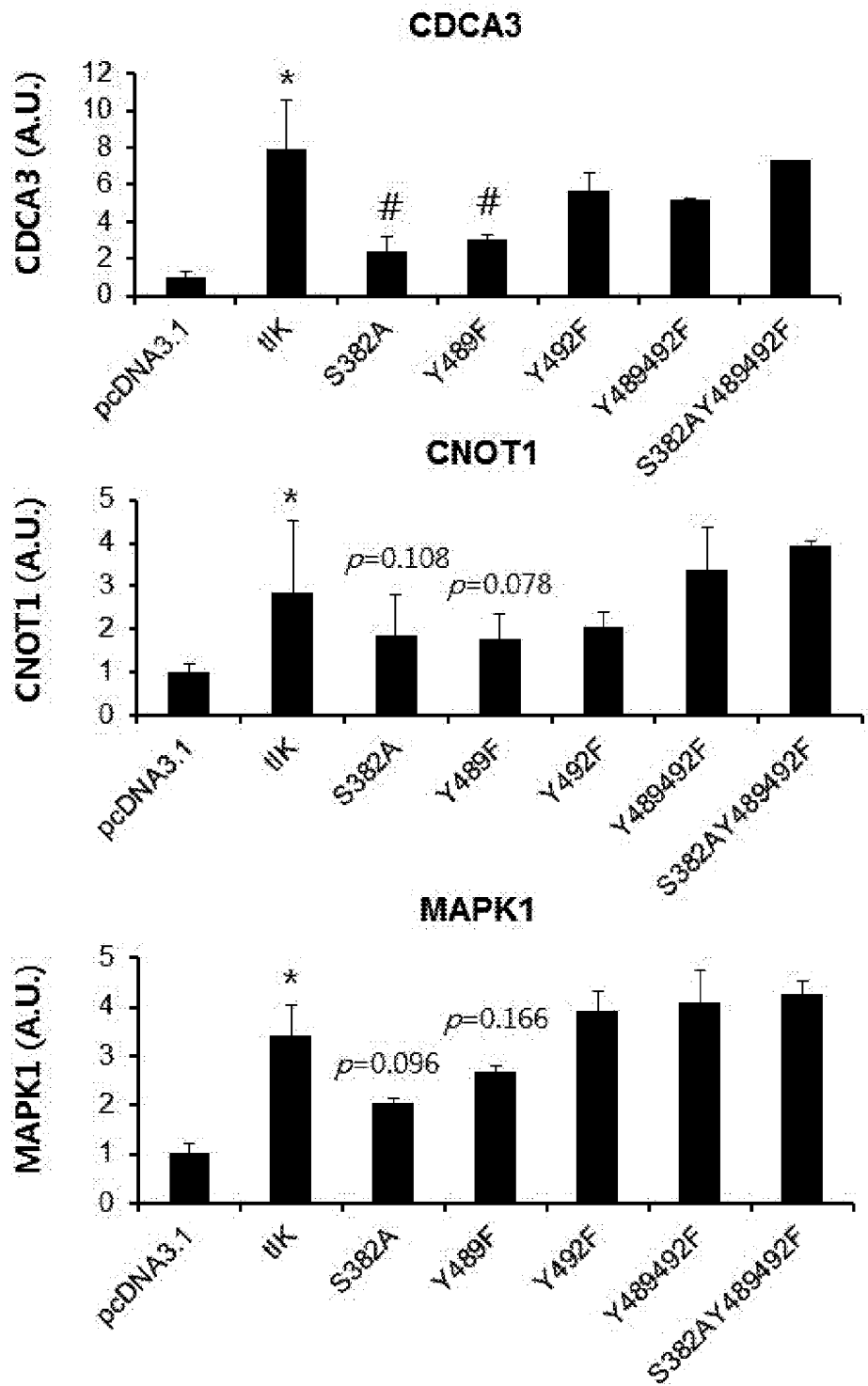

[FIG. 4A]
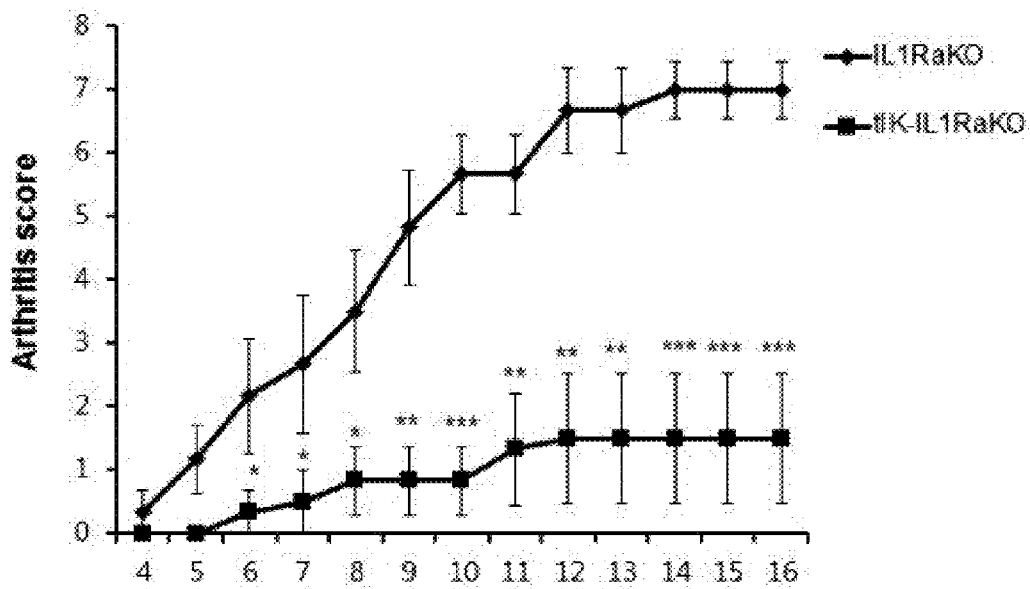
[FIG. 4B]
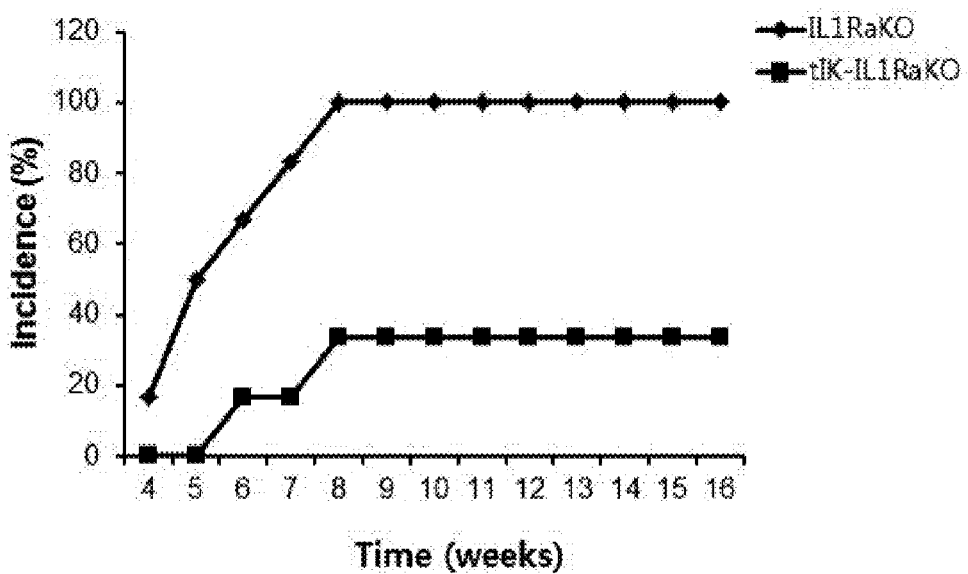

[FIG. 5]
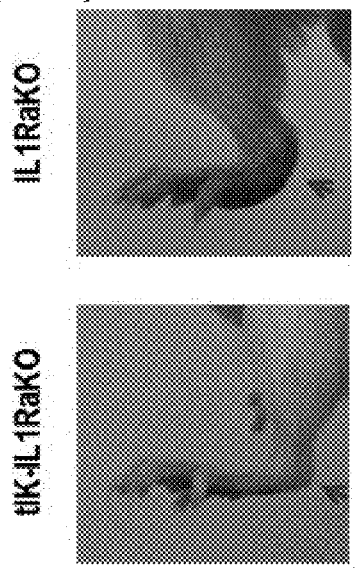
[FIG. 6A]
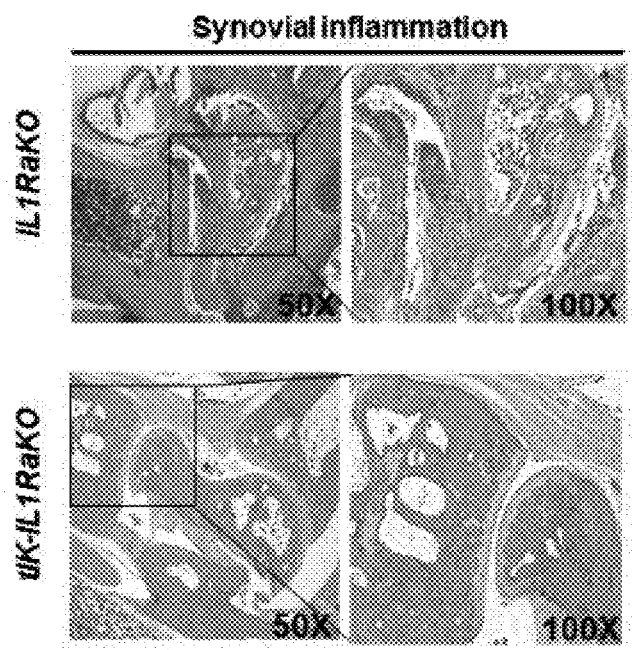
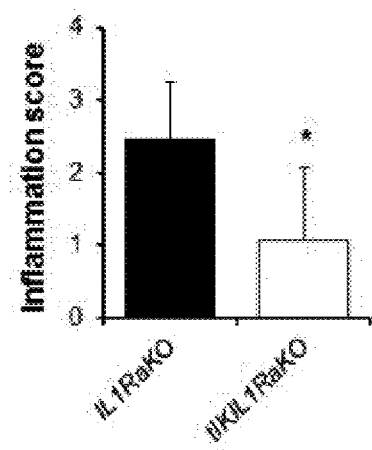

[FIG. 6B]
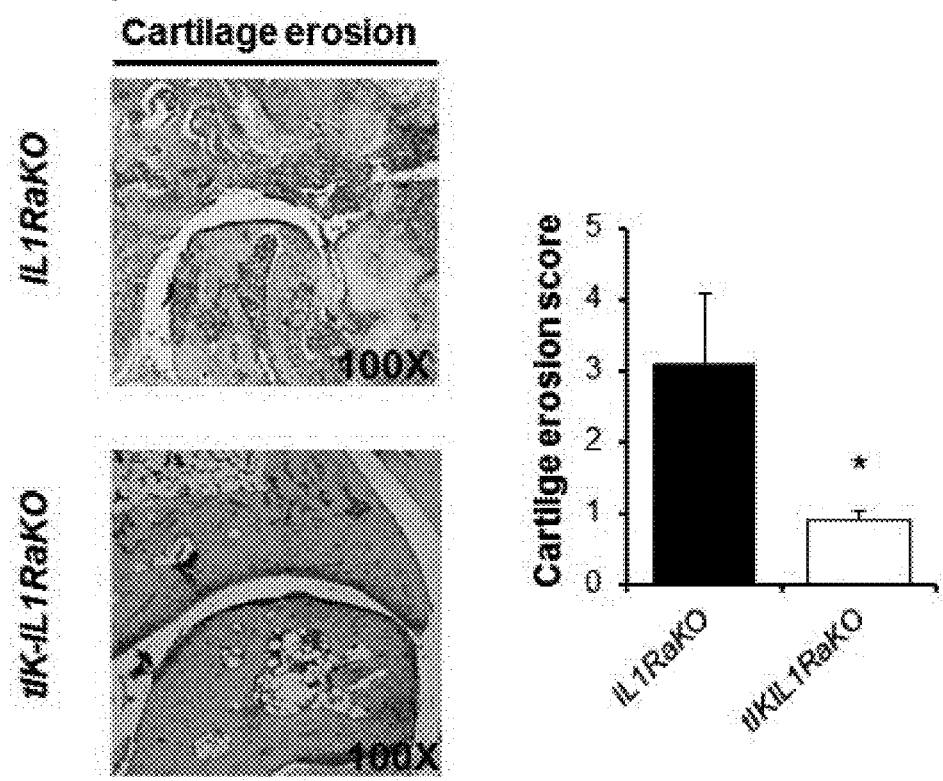

[FIG. 7]
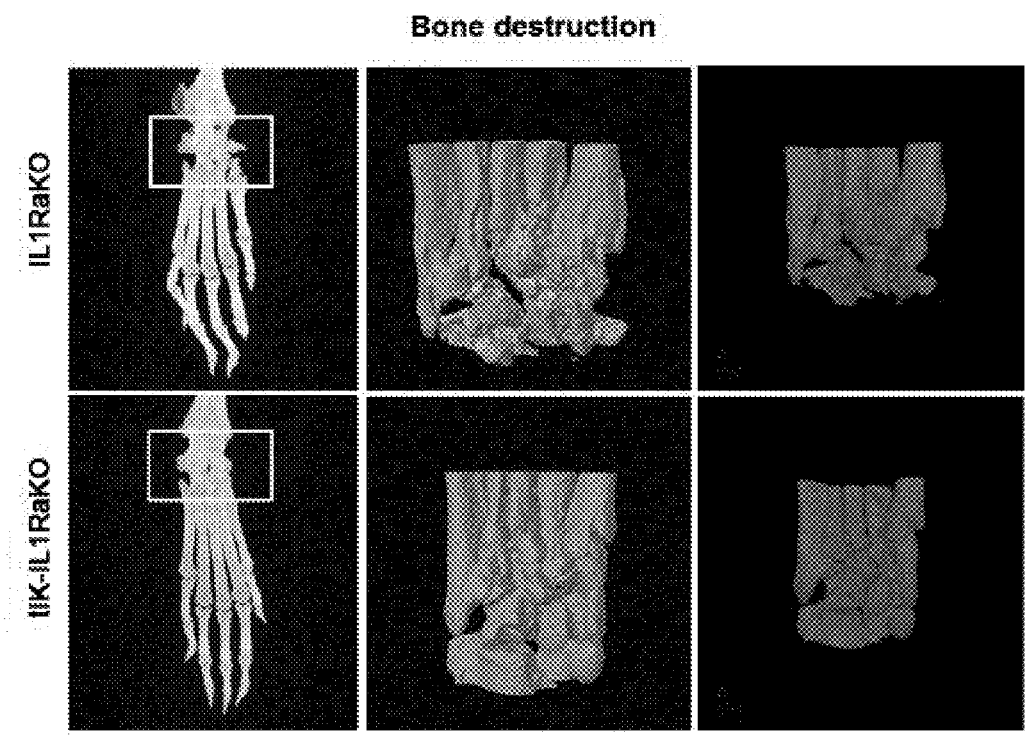
[FIG. 8A]
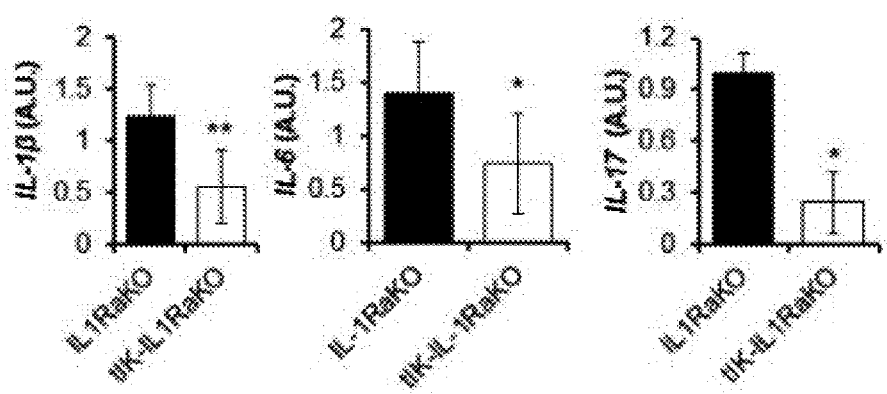

[FIG. 8B]
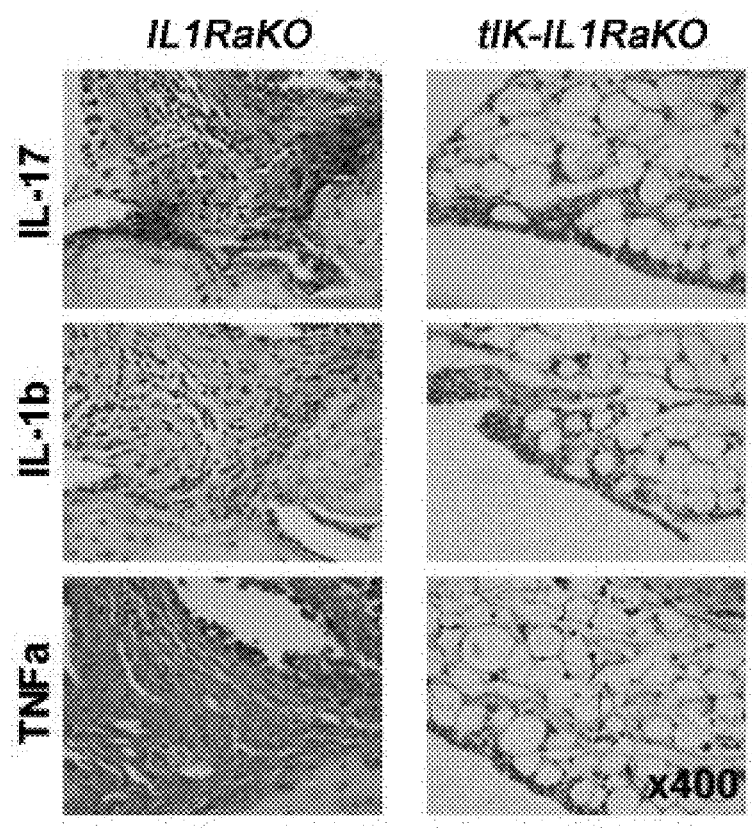

[FIG. 9]
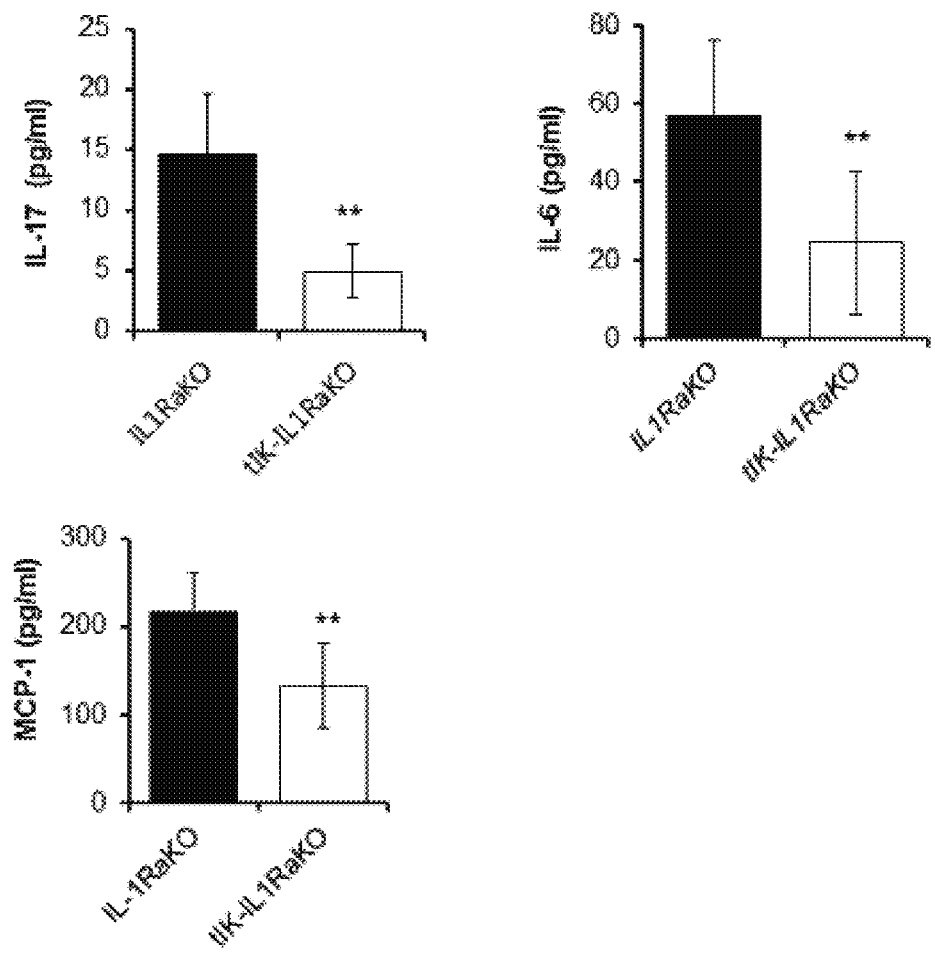

[FIG. 10A]
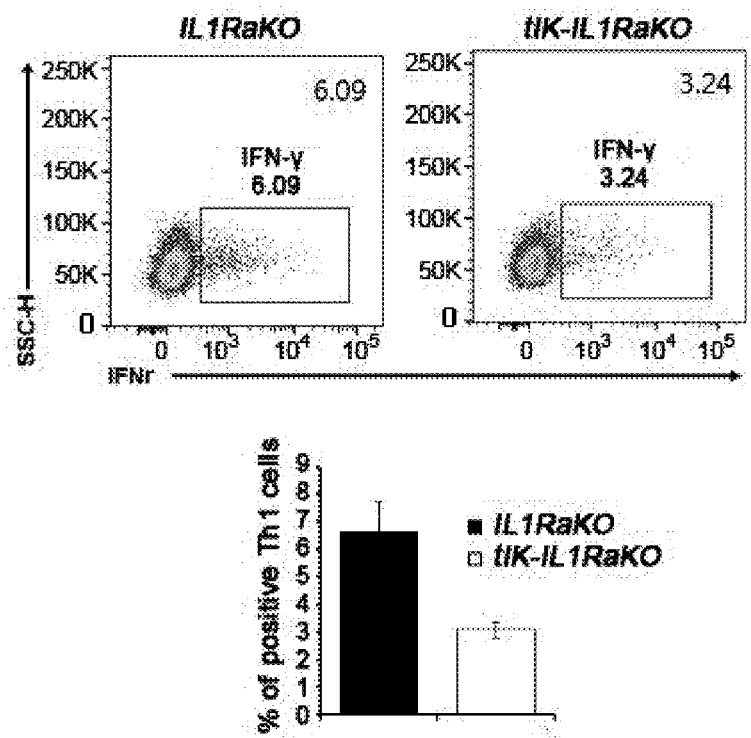
[FIG. 10B]
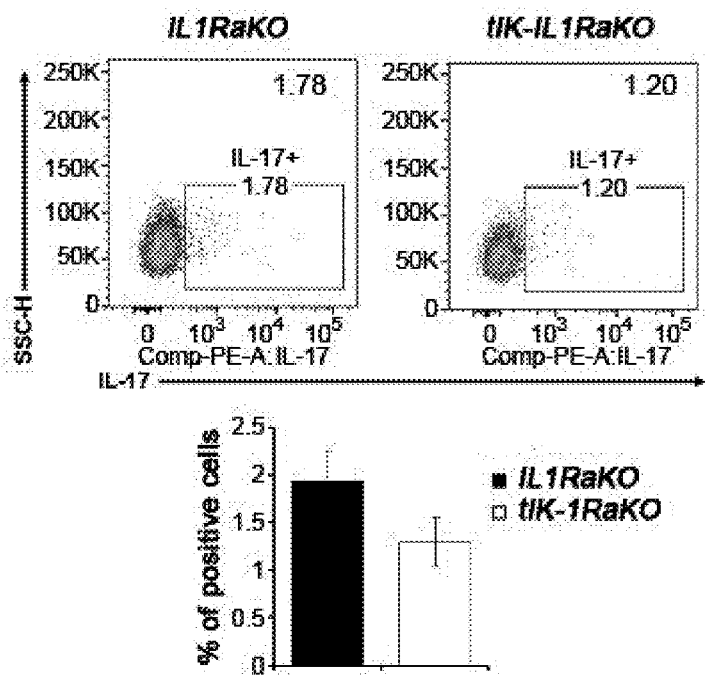

[FIG. 11]
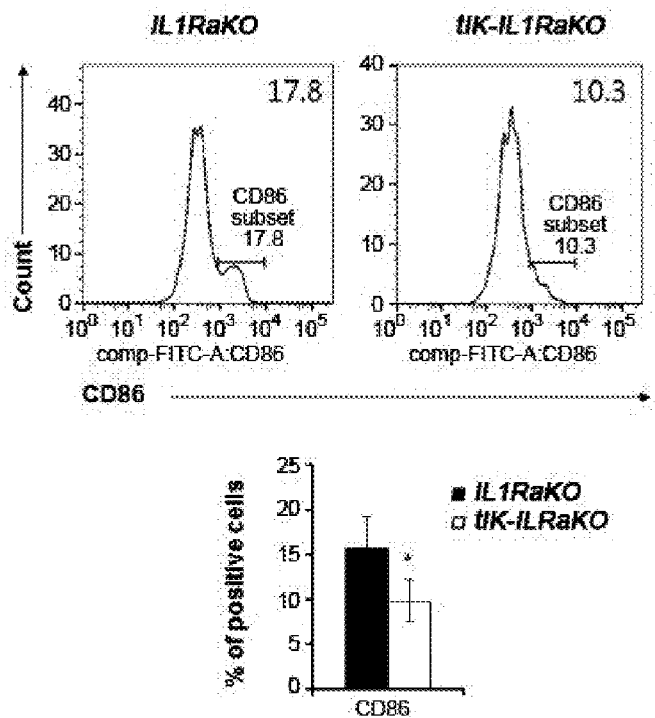
[FIG. 12A]
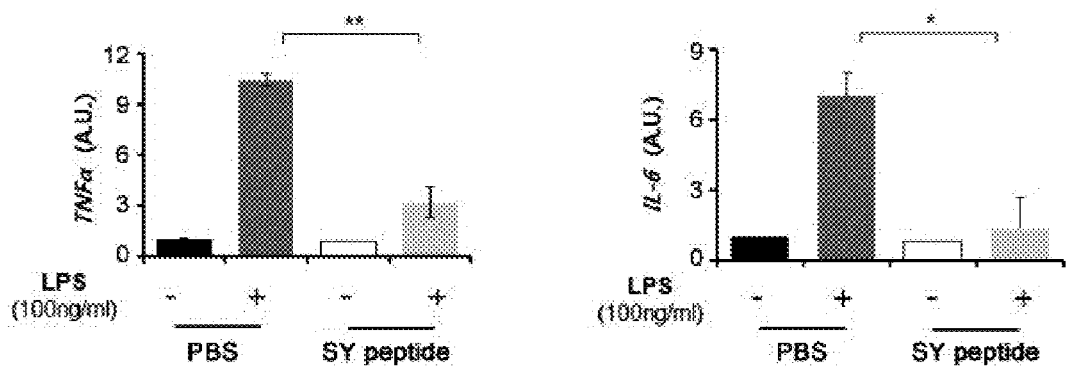

[FIG. 12B]
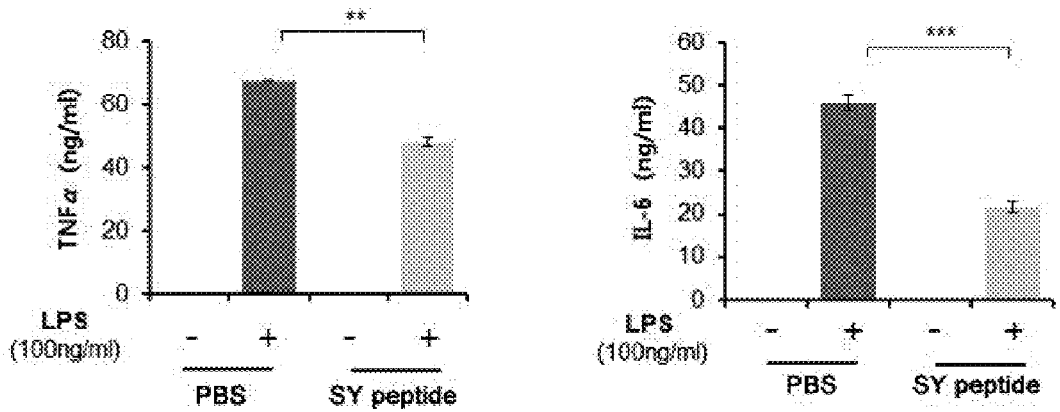
[FIG. 13A]
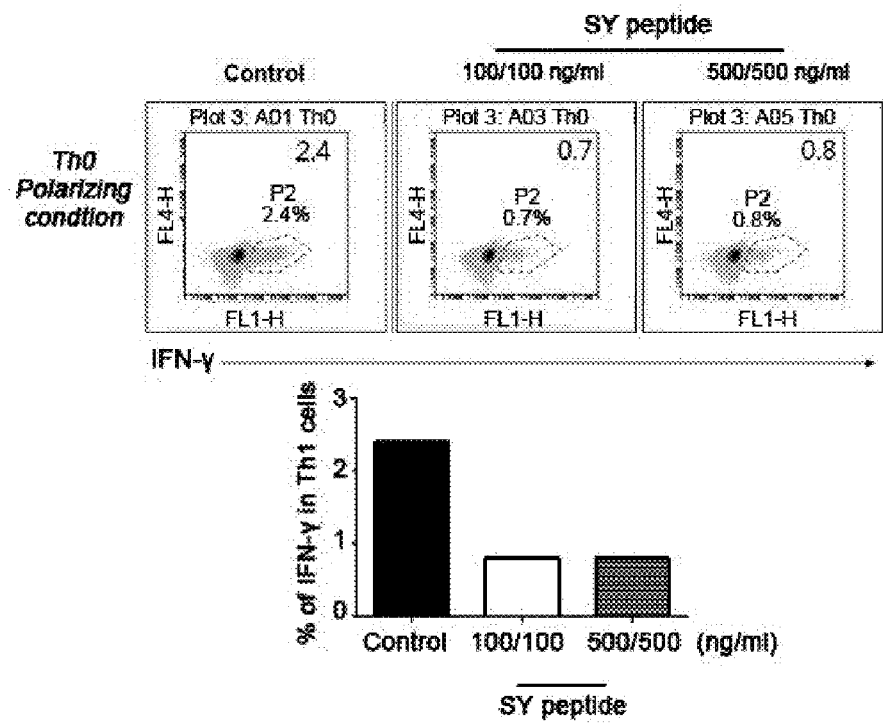

[FIG. 13B]
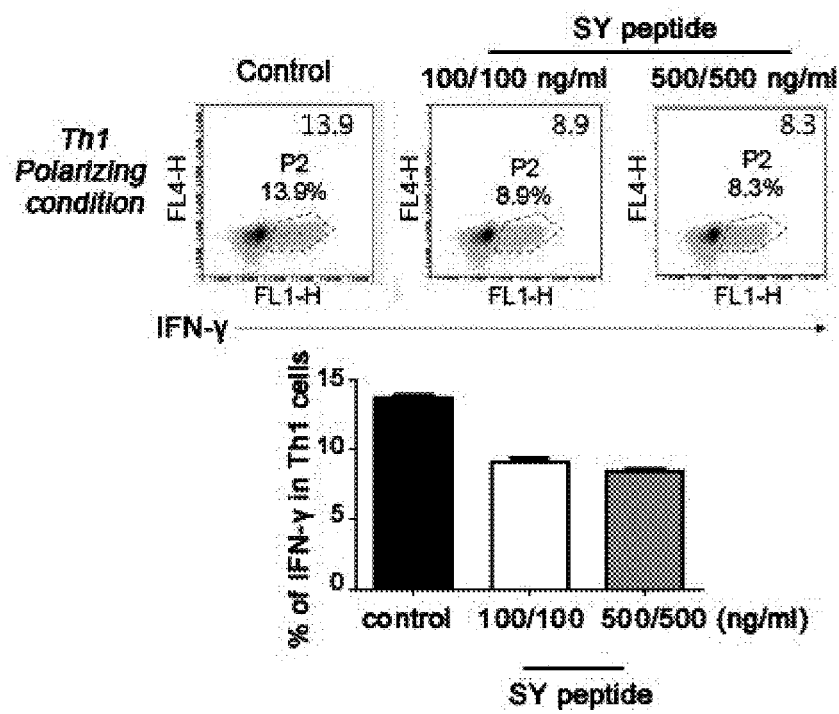
[FIG. 13C]
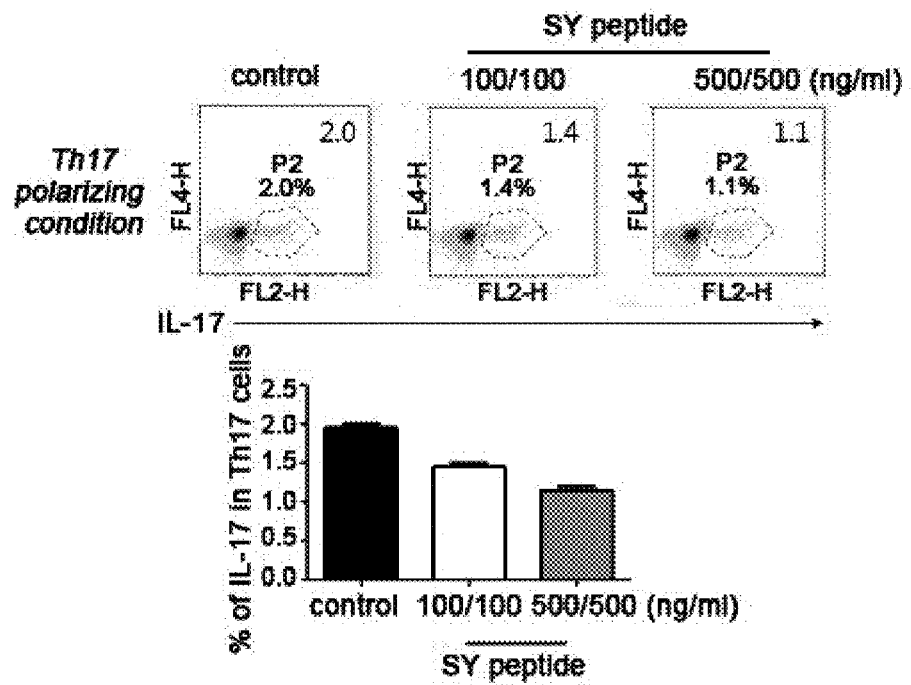

[FIG. 14A]
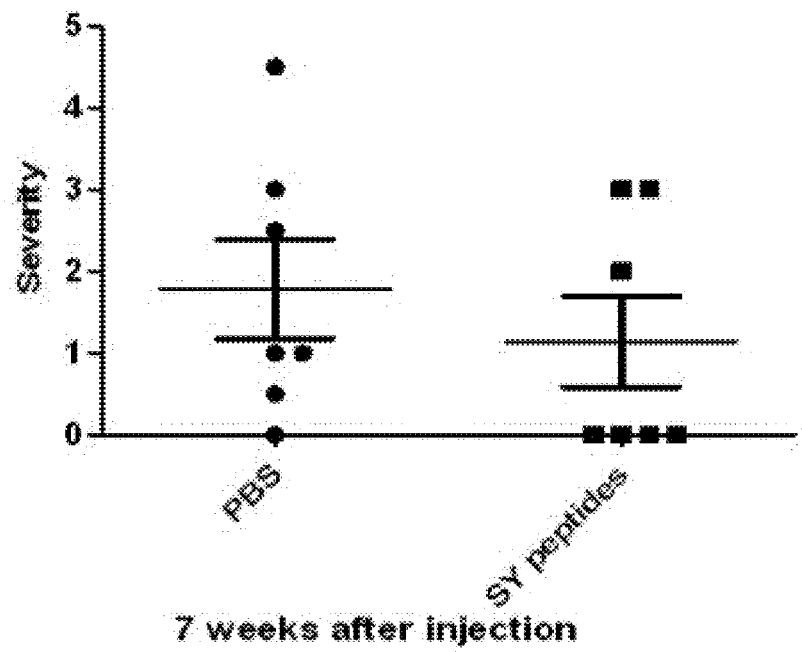
[FIG. 14B]

[FIG. 15A]
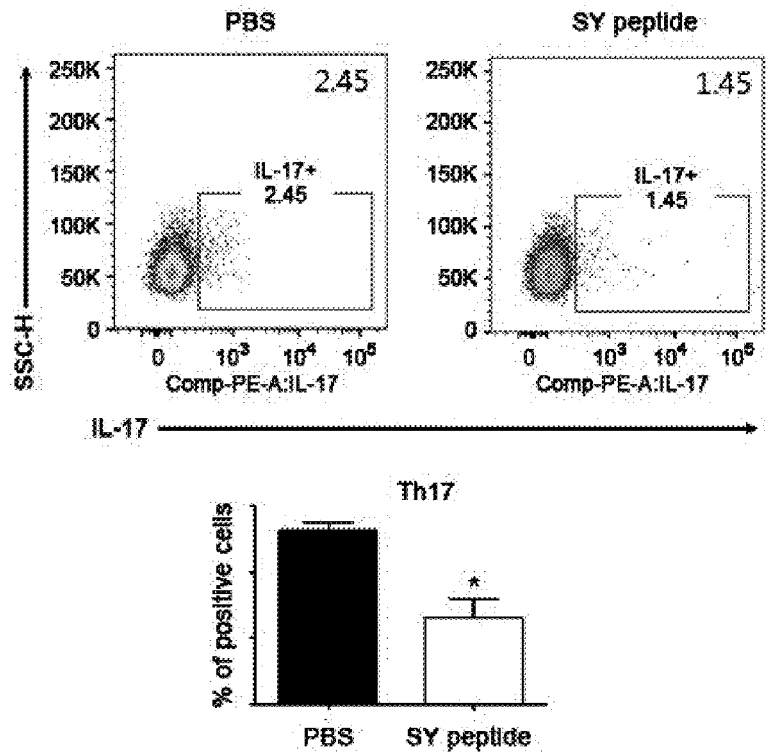
[FIG. 15B]
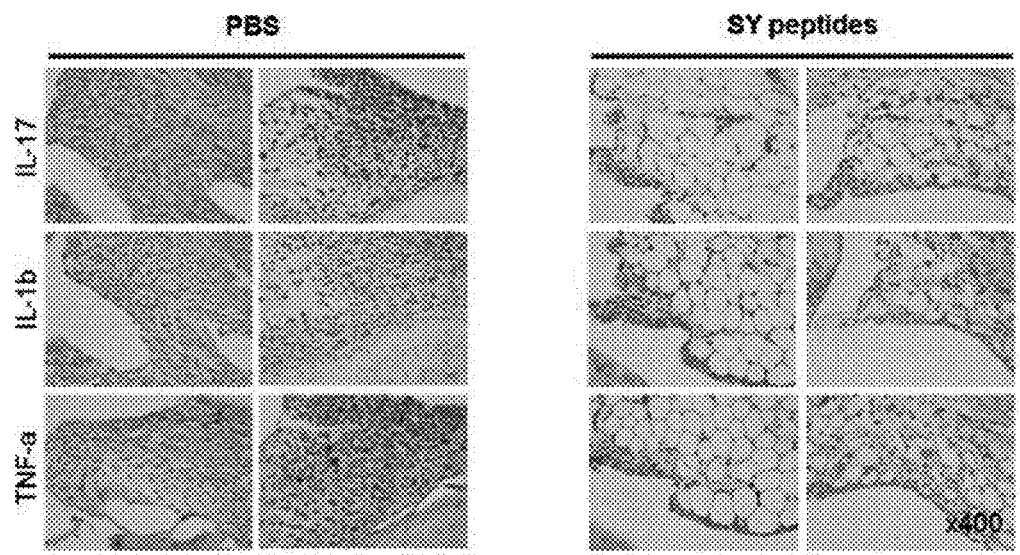

[FIG. 16]
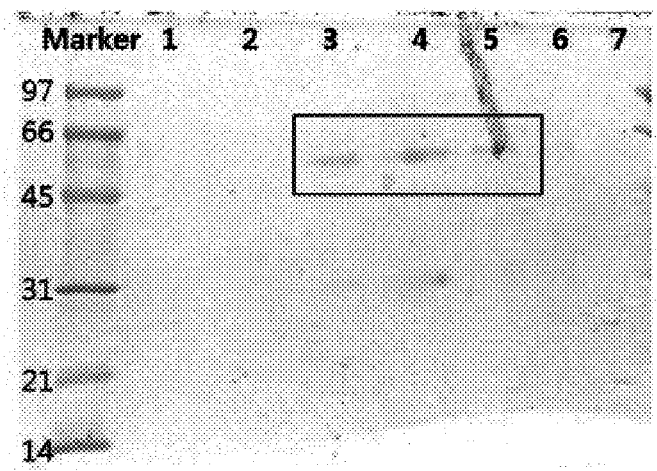
[FIG. 17]
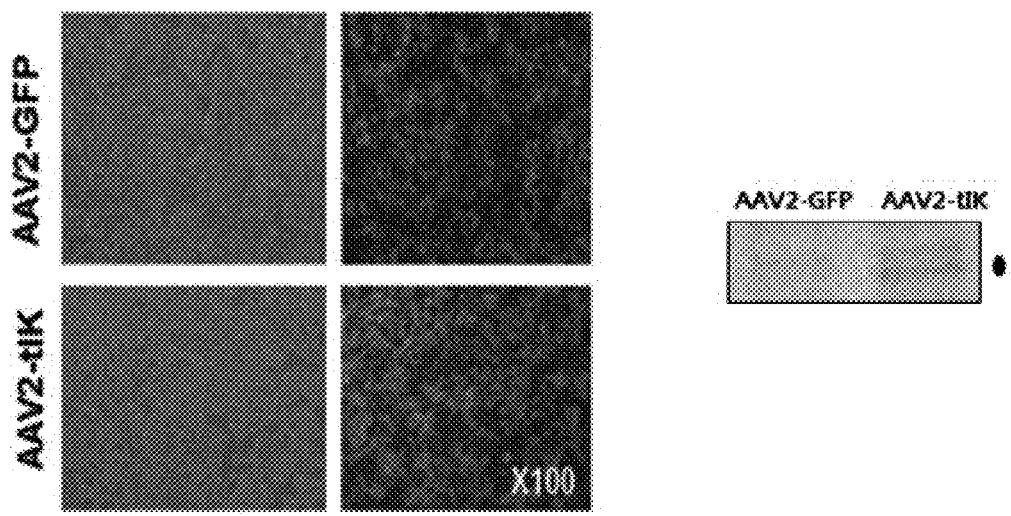

[FIG. 18A]
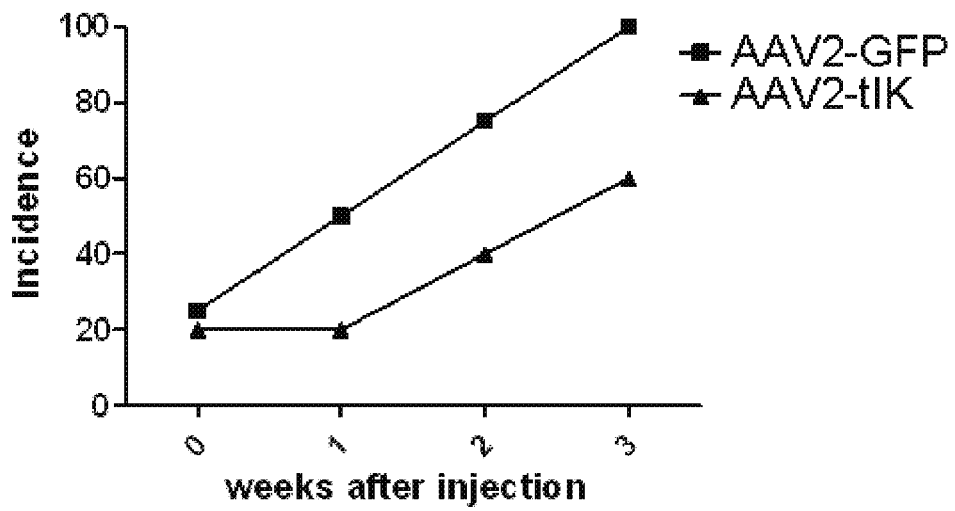
[FIG. 18B]
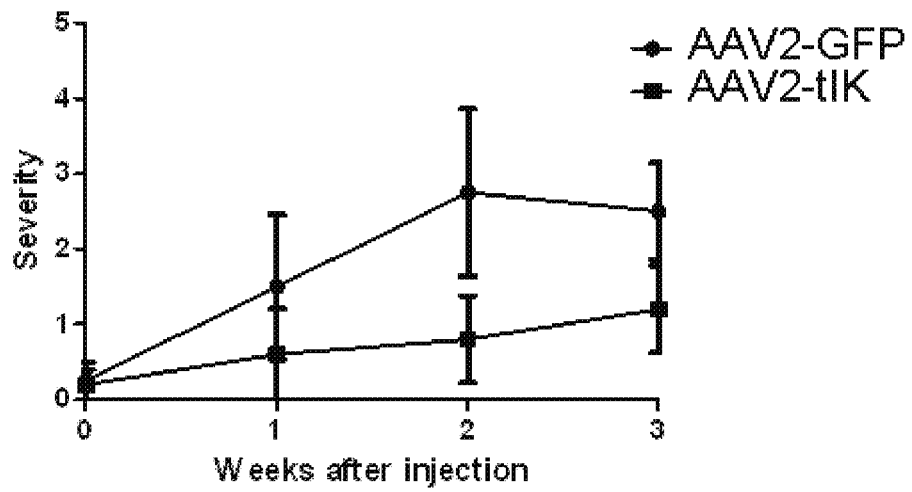
[FIG. 19]
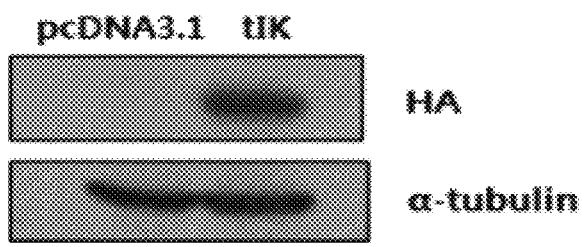

SEQUENCE LISTING

```
<160> NUMBER OF SEQ ID NOS: 57

<210> SEQ ID NO 1
<211> LENGTH: 1674
<212> TYPE: DNA
<213> ORGANISM: Homo sapiens

<400> SEQUENCE: 1
atgccagaac gagatagtga gcccttctct aacccttgg ctccagatgg ccacgatgtg     60
gatgatcctc attccttcca ccaatcaaaa cttaccaatg aagacttcag gaaacttctt    120 atgacccaa gagctgcacc tacttctgcg ccaccttcta agtcacgtca ccatgagatg    180
ccaagggagt acaatgagga tgaagaccca gctgcacgaa ggaggaaaaa gaaaagttat    240
tatgccaagc ttcgccagca agaaattgag agagagagag aactcgcaga gaataccgg     300 gaccgtgcca aggaacggag agatggtgtg aacaaagact atgaggaaac tgagctgata    360
```

```
agtaccacag ccaactacag ggctgtgggc cccactgctg aggcggacaa atcagcagca    420
gagaagagaa gacagttgat tcaggagtcc aaattcttgg gtggtgatat ggaacacacc    480
catttggtga aaggtttgga ttttgcgttg cttcaaaagg tgcgcgctga gattgccagc    540
aaagagaagg aggaagagga actcatggaa aagccccaaa aggaaaccaa gaaagatgag    600
gatcctgaga acaaaattga atttaaaaca cgccttggcc ggaatgtgta tcggatgctt    660
ttcaagagta atcatatga gcgaaatgag ctgttcttac caggacgtat ggcctatgta    720
gtagacctgg atgatgagta cgcagacaca gatatcccca ccactctcat acgcagcaaa    780
gctgattgcc ccactatgga ggcccagact acactgacta caaatgacat tgttattagc    840
aagctcaccc agattttgtc atacctgagg caggggaccc gaaacaagaa gctcaagaag    900
aaggataaag gaaaactgga gagaagaaa cctcctgagg ctgacatgaa cattttttgaa    960 gacattgggg attacgttcc ttctacaacc aagacacctc gggacaagga acgtgagaga   1020
taccgggaac gtgaacgtga tcgggaacgg gacagagaca gggagcgaga cagggagcga   1080
gaccgtgaga gggagagaga gcgagaccgg gaacgggaac gagaggagga aaagaaaagg   1140
cacagctact ttgagaagcc aaaagtggat gatgagccca tggatgttga caaaggacct   1200
ggatctgcaa aagagttgat caagtccatc aatgaaaaat cgctgggtc tgctggctgg   1260 gaaggcactg aatcgttgaa gaagccagaa gataagaagc agctgggcga tttctttggc   1320
atgtccaaca gttacgcaga atgctatcca gccacgatgg atgacatggc tgtagatagt   1380
gatgaagagg tagattatag caaaatggac cagggtaaca agaagggtcc cttaggccgc   1440
tgggacttcg atactcagga ggaatacagc gagtacatga caacaaggga ggctctgccc   1500
aaggctgcat tccagtatgg catcaagatg tctgaaggac ggaaaaccag acgattcaaa   1560
gaaaccaatg ataaggcaga gcttgatcga cagtggaaga aaataagtgc aatcattgag   1620
aagaggaaga ggatggaagc agatggggtc gaagtgaaaa gaccaaagta ctaa         1674
```

<210> SEQ ID NO 2
<211> LENGTH: 557
<212> TYPE: PRT
<213> ORGANISM: Homo sapiens

<400> SEQUENCE: 2

```
Met Pro Glu Arg Asp Ser Glu Pro Phe Ser Asn Pro Leu Ala Pro Asp
1               5                   10                  15

Gly His Asp Val Asp Asp Pro His Ser Phe His Gln Ser Lys Leu Thr
            20                  25                  30

Asn Glu Asp Phe Arg Lys Leu Leu Met Thr Pro Arg Ala Ala Pro Thr
        35                  40                  45

Ser Ala Pro Pro Ser Lys Ser Arg His His Glu Met Pro Arg Glu Tyr
    50                  55                  60

Asn Glu Asp Glu Asp Pro Ala Ala Arg Arg Lys Lys Lys Ser Tyr
65                  70                  75                  80

Tyr Ala Lys Leu Arg Gln Gln Glu Ile Glu Arg Glu Arg Glu Leu Ala
                85                  90                  95

Glu Lys Tyr Arg Asp Arg Ala Lys Glu Arg Arg Asp Gly Val Asn Lys
            100                 105                 110

Asp Tyr Glu Glu Thr Glu Leu Ile Ser Thr Thr Ala Asn Tyr Arg Ala
        115                 120                 125

Val Gly Pro Thr Ala Glu Ala Asp Lys Ser Ala Ala Glu Lys Arg Arg
    130                 135                 140
```

-continued

```
Gln Leu Ile Gln Glu Ser Lys Phe Leu Gly Asp Met Glu His Thr
145                 150                 155                 160

His Leu Val Lys Gly Leu Asp Phe Ala Leu Leu Gln Lys Val Arg Ala
                165                 170                 175

Glu Ile Ala Ser Lys Glu Lys Glu Glu Glu Leu Met Glu Lys Pro
            180                 185                 190

Gln Lys Glu Thr Lys Lys Asp Glu Asp Pro Glu Asn Lys Ile Glu Phe
        195                 200                 205

Lys Thr Arg Leu Gly Arg Asn Val Tyr Arg Met Leu Phe Lys Ser Lys
    210                 215                 220

Ala Tyr Glu Arg Asn Glu Leu Phe Leu Pro Gly Arg Met Ala Tyr Val
225                 230                 235                 240

Val Asp Leu Asp Asp Glu Tyr Ala Asp Thr Asp Ile Pro Thr Thr Leu
                245                 250                 255

Ile Arg Ser Lys Ala Asp Cys Pro Thr Met Glu Ala Gln Thr Thr Leu
            260                 265                 270

Thr Thr Asn Asp Ile Val Ile Ser Lys Leu Thr Gln Ile Leu Ser Tyr
        275                 280                 285

Leu Arg Gln Gly Thr Arg Asn Lys Lys Leu Lys Lys Asp Lys Gly
    290                 295                 300

Lys Leu Glu Glu Lys Lys Pro Pro Glu Ala Asp Met Asn Ile Phe Glu
305                 310                 315                 320

Asp Ile Gly Asp Tyr Val Pro Ser Thr Thr Lys Thr Pro Arg Asp Lys
                325                 330                 335

Glu Arg Glu Arg Tyr Arg Glu Arg Glu Arg Asp Arg Glu Arg Asp Arg
            340                 345                 350

Asp Arg Asp Arg Glu Arg Glu Arg Glu Arg Asp Arg Glu Arg Glu Arg
        355                 360                 365

Glu Arg Asp Arg Glu Arg Glu Glu Lys Lys Arg His Ser Tyr Phe
    370                 375                 380

Glu Lys Pro Lys Val Asp Asp Glu Pro Met Asp Val Asp Lys Gly Pro
385                 390                 395                 400

Gly Ser Thr Lys Glu Leu Ile Lys Ser Ile Asn Glu Lys Phe Ala Gly
                405                 410                 415

Ser Ala Gly Trp Glu Gly Thr Glu Ser Leu Lys Lys Pro Glu Asp Lys
            420                 425                 430

Lys Gln Leu Gly Asp Phe Phe Gly Met Ser Asn Ser Tyr Ala Glu Cys
        435                 440                 445

Tyr Pro Ala Thr Met Asp Met Ala Val Asp Ser Asp Glu Glu Val
    450                 455                 460

Asp Tyr Ser Lys Met Asp Gln Gly Asn Lys Lys Gly Pro Leu Gly Arg
465                 470                 475                 480

Trp Asp Phe Asp Thr Gln Glu Glu Tyr Ser Glu Tyr Met Asn Asn Lys
                485                 490                 495

Glu Ala Leu Pro Lys Ala Ala Phe Gln Tyr Gly Ile Lys Met Ser Glu
            500                 505                 510

Gly Arg Lys Thr Arg Arg Phe Lys Glu Thr Asn Asp Lys Ala Glu Leu
        515                 520                 525

Asp Arg Gln Trp Lys Lys Ile Ser Ala Ile Ile Glu Lys Arg Lys Lys
    530                 535                 540

Met Glu Ala Asp Gly Val Glu Val Lys Arg Pro Lys Tyr
545                 550                 555
```

```
<210> SEQ ID NO 3
<211> LENGTH: 726
<212> TYPE: DNA
<213> ORGANISM: Homo sapiens

<400> SEQUENCE: 3
atgaacattt tgaagacat tgggattac gttccttcta caaccaagac acctcgggac    60
aaggaacgtg agagataccg ggaacgtgaa cgtgatcggg aacgggacag agacagggag   120
cgagacaggg agcgagaccg tgagagggag agagagcgag accggaacg ggaacgagag   180 gaggaaaaga aaaggcacag ctactttgag aagccaaaag tggatgatga gcccatggat   240
gttgacaaag gacctggatc tgcaaaagag ttgatcaagt ccatcaatga aaaattcgct   300
gggtctgctg gctgggaagg cactgaatcg ttgaagaagc agaagataa aagcagctg    360 ggcgattcct ttggcatgtc caacagttac gcagaatgct atccagccac gatggatgac   420
atggctgtag atagtgatga agaggtagat tatagcaaaa tggaccaggg taacaagaag   480
ggtcccttag ccgctggga cttcgatact caggaggaat acagcgagta catgaacaac   540
aaggaggctc tgcccaaggc tgcattccag tatggcatca gatgtctga aggacggaaa   600 accagacgat tcaaagaaac caatgataag gcagagcttg atcgacagtg aagaaaata   660 agtgcaatca ttgagaagag gaagaggatg gaagcagatg gggtcgaagt gaaaagacca   720
aagtac                                                             726

<210> SEQ ID NO 4
<211> LENGTH: 242
<212> TYPE: PRT
<213> ORGANISM: Homo sapiens

<400> SEQUENCE: 4

Met Asn Ile Phe Glu Asp Ile Gly Asp Tyr Val Pro Ser Thr Thr Lys
1               5                   10                  15

Thr Pro Arg Asp Lys Glu Arg Glu Arg Tyr Arg Glu Arg Glu Arg Asp
                20                  25                  30

Arg Glu Arg Asp Arg Asp Arg Glu Arg Asp Arg Glu Arg Asp Arg Glu
            35                  40                  45

Arg Glu Arg Glu Arg Asp Arg Glu Arg Glu Glu Glu Glu Lys Lys
        50                  55                  60

Arg His Ser Tyr Phe Glu Lys Pro Lys Val Asp Asp Glu Pro Met Asp
65                  70                  75                  80

Val Asp Lys Gly Pro Gly Ser Ala Lys Glu Leu Ile Lys Ser Ile Asn
                85                  90                  95

Glu Lys Phe Ala Gly Ser Ala Gly Trp Glu Gly Thr Glu Ser Leu Lys
            100                 105                 110

Lys Pro Glu Asp Lys Gln Leu Gly Asp Phe Phe Gly Met Ser Asn
        115                 120                 125

Ser Tyr Ala Glu Cys Tyr Pro Ala Thr Met Asp Met Ala Val Asp
    130                 135                 140

Ser Asp Glu Glu Val Asp Tyr Ser Lys Met Asp Gln Gly Asn Lys Lys
145                 150                 155                 160

Gly Pro Leu Gly Arg Trp Asp Phe Asp Thr Gln Glu Glu Tyr Ser Glu
                165                 170                 175

Tyr Met Asn Asn Lys Glu Ala Leu Pro Lys Ala Ala Phe Gln Tyr Gly
            180                 185                 190

Ile Lys Met Ser Glu Gly Arg Lys Thr Arg Arg Phe Lys Glu Thr Asn
        195                 200                 205
```

Asp Lys Ala Glu Leu Asp Arg Gln Trp Lys Lys Ile Ser Ala Ile Ile
    210                 215                 220

Glu Lys Arg Lys Arg Met Glu Ala Asp Gly Val Glu Val Lys Arg Pro
225                 230                 235                 240

Lys Tyr

<210> SEQ ID NO 5
<211> LENGTH: 726
<212> TYPE: DNA
<213> ORGANISM: Artificial Sequence
<220> FEATURE:
<223> OTHER INFORMATION: Nucleic acid encodding mutated partial IK
      factor

<400> SEQUENCE: 5
atgaacattt ttgaagacat tggggattac gttccttcta caaccaagac acctcgggac      60
aaggaacgtg agagataccg ggaacgtgaa cgtgatcggg aacgggacag agacagggag     120
cgagacaggg agcgagaccg tgagagggag agagagcgag accgggaacg ggaacgagag     180
gaggaaaaga aaaggcacgc ctactttgag aagccaaaag tggatgatga gcccatggat     240
gttgacaaag gacctggatc tgcaaaagag ttgatcaagt ccatcaatga aaaattcgct     300
gggtctgctg gctgggaagg cactgaatcg ttgaagaagc cagaagataa gaagcagctg     360
ggcgatttct ttggcatgtc caacagttac gcagaatgct atccagccac gatggatgac     420
atggctgtag atagtgatga gaggtagat tatagcaaaa tggaccaggg taacaagaag      480
ggtcccttag ccgctggga cttcgatact caggaggaat acagcgagta catgaacaac     540
aaggaggctc tgcccaaggc tgcattccag tatggcatca agatgtctga aggacggaaa     600
accagacgat tcaaagaaac caatgataag gcagagcttg atcgacagtg aagaaaata     660 agtgcaatca ttgagaagag gaagaggatg gaagcagatg gggtcgaagt gaaaagacca     720
aagtac                                                                726

<210> SEQ ID NO 6
<211> LENGTH: 242
<212> TYPE: PRT
<213> ORGANISM: Artificial Sequence
<220> FEATURE:
<223> OTHER INFORMATION: Mutated partial IK factor

<400> SEQUENCE: 6

Met Asn Ile Phe Glu Asp Ile Gly Asp Tyr Val Pro Ser Thr Thr Lys
1               5                   10                  15

Thr Pro Arg Asp Lys Glu Arg Glu Tyr Arg Glu Arg Glu Arg Asp
            20                  25                  30

Arg Glu Arg Asp Arg Asp Arg Glu Arg Asp Arg Glu Arg Asp Arg Glu
            35                  40                  45

Arg Glu Arg Glu Arg Asp Arg Glu Arg Glu Glu Lys Lys
            50                  55                  60

Arg His Ala Tyr Phe Glu Lys Pro Lys Val Asp Asp Glu Pro Met Asp
65                  70                  75                  80

Val Asp Lys Gly Pro Gly Ser Ala Lys Glu Leu Ile Lys Ser Ile Asn
                85                  90                  95

Glu Lys Phe Ala Gly Ser Ala Gly Trp Glu Gly Thr Glu Ser Leu Lys
            100                 105                 110

Lys Pro Glu Asp Lys Lys Gln Leu Gly Asp Phe Phe Gly Met Ser Asn
            115                 120                 125

Ser Tyr Ala Glu Cys Tyr Pro Ala Thr Met Asp Asp Met Ala Val Asp
    130                 135                 140

Ser Asp Glu Glu Val Asp Tyr Ser Lys Met Asp Gln Gly Asn Lys Lys
145                 150                 155                 160

Gly Pro Leu Gly Arg Trp Asp Phe Asp Thr Gln Glu Glu Tyr Ser Glu
                165                 170                 175

Tyr Met Asn Asn Lys Glu Ala Leu Pro Lys Ala Ala Phe Gln Tyr Gly
            180                 185                 190

Ile Lys Met Ser Glu Gly Arg Lys Thr Arg Arg Phe Lys Glu Thr Asn
        195                 200                 205

Asp Lys Ala Glu Leu Asp Arg Gln Trp Lys Lys Ile Ser Ala Ile Ile
    210                 215                 220

Glu Lys Arg Lys Arg Met Glu Ala Asp Gly Val Glu Val Lys Arg Pro
225                 230                 235                 240

Lys Tyr

<210> SEQ ID NO 7
<211> LENGTH: 726
<212> TYPE: DNA
<213> ORGANISM: Artificial Sequence
<220> FEATURE:
<223> OTHER INFORMATION: Mutated partial IK factor

<400> SEQUENCE: 7

| | | |
|---|---|---|
| atgaacattt tgaagacat tggggattac gttccttcta caaccaagac acctcgggac | 60 |
| aaggaacgtg agagataccg ggaacgtgaa cgtgatcggg aacgggacag agacagggag | 120 |
| cgagacaggg agcgagaccg tgagagggag agagagcgag accgggaacg ggaacgagag | 180 |
| gaggaaaaga aaaggcacag ctactttgag aagccaaaag tggatgatga gcccatggat | 240 |
| gttgacaaag gacctggatc tgcaaaagag ttgatcaagt ccatcaatga aaaattcgct | 300 |
| gggtctgctg ctgggaagg cactgaatcg ttgaagaagc cagaagataa gaagcagctg | 360 |
| ggcgatttct ttggcatgtc caacagttac gcagaatgct atccagccac gatggatgac | 420 |
| atggctgtag atagtgatga agaggtagat tatagcaaaa tggaccaggg taacaagaag | 480 |
| ggtccttag ccgctggga cttcgatact caggaggaat cagcgagta catgaacaac | 540 |
| aaggaggctc tgcccaaggc tgcattccag tatggcatca gatgtctga aggacgaaa | 600 |
| accagacgat tcaaagaaac caatgataag gcagagcttg atcgacagtg gaagaaaata | 660 |
| agtgcaatca ttgagaagag gaagaggatg gaagcagatg gggtcgaagt gaaaagacca | 720 |
| aagtac | 726 |

<210> SEQ ID NO 8
<211> LENGTH: 242
<212> TYPE: PRT
<213> ORGANISM: Artificial Sequence
<220> FEATURE:
<223> OTHER INFORMATION: Mutated partial IK factor

<400> SEQUENCE: 8

Met Asn Ile Phe Glu Asp Ile Gly Asp Tyr Val Pro Ser Thr Thr Lys
1               5                   10                  15

Thr Pro Arg Asp Lys Glu Arg Glu Arg Tyr Arg Glu Arg Glu Arg Asp
            20                  25                  30

Arg Glu Arg Asp Arg Asp Arg Glu Arg Asp Arg Glu Arg Asp Arg Glu
        35                  40                  45

Arg Glu Arg Glu Arg Asp Arg Glu Arg Glu Glu Lys Lys
    50                  55                  60

Arg His Ser Tyr Phe Glu Lys Pro Lys Val Asp Asp Glu Pro Met Asp
65                  70                  75                  80

Val Asp Lys Gly Pro Gly Ser Ala Lys Glu Leu Ile Lys Ser Ile Asn
                85                  90                  95

Glu Lys Phe Ala Gly Ser Ala Gly Trp Glu Gly Thr Glu Ser Leu Lys
            100                 105                 110

Lys Pro Glu Asp Lys Lys Gln Leu Gly Asp Phe Phe Gly Met Ser Asn
            115                 120                 125

Ser Tyr Ala Glu Cys Tyr Pro Ala Thr Met Asp Asp Met Ala Val Asp
    130                 135                 140

Ser Asp Glu Glu Val Asp Tyr Ser Lys Met Asp Gln Gly Asn Lys Lys
145                 150                 155                 160

Gly Pro Leu Gly Arg Trp Asp Phe Asp Thr Gln Glu Glu Phe Ser Glu
                165                 170                 175

Tyr Met Asn Asn Lys Gly Ala Leu Pro Lys Ala Ala Phe Gln Tyr Gly
            180                 185                 190

Ile Lys Met Ser Glu Gly Arg Lys Thr Arg Arg Phe Lys Glu Thr Asn
            195                 200                 205

Asp Lys Ala Glu Leu Asp Arg Gln Trp Lys Lys Ile Ser Ala Ile Ile
    210                 215                 220

Glu Lys Arg Lys Arg Met Glu Ala Asp Gly Val Glu Val Lys Arg Pro
225                 230                 235                 240

Lys Tyr

<210> SEQ ID NO 9
<211> LENGTH: 726
<212> TYPE: DNA
<213> ORGANISM: Artificial Sequence
<220> FEATURE:
<223> OTHER INFORMATION: Mutated partial IK factor

<400> SEQUENCE: 9
atgaacattt tgaagacat tggggattac gttccttcta caaccaagac acctcgggac        60
aaggaacgtg agagataccg ggaacgtgaa cgtgatcggg aacgggacag agacagggag      120
cgagacaggg agcgagaccg tgagagggag agagagcgag accgggaacg ggaacgagag      180
gaggaaaaga aaaggcacag ctactttgag aagccaaaag tggatgatga gcccatggat      240
gttgacaaag gacctggatc tgcaaaagag ttgatcaagt ccatcaatga aaaattcgct      300
gggtctgctg gctgggaagg cactgaatcg ttgaagaagc cagaagataa gaagcagctg      360
ggcgatttct ttggcatgtc caacagttac gcagaatgct atccagccac gatggatgac      420
atggctgtag atagtgatga agaggtagat tatagcaaaa tggaccaggg taacaagaag      480
ggtcccttag ccgctgggaa cttcgatact caggaggaat acagcgagtt catgaacaac      540
aaggaggctc tgcccaaggc tgcattccag tatggcatca gatgtctga aggacggaaa       600 accagacgat tcaaagaaac caatgataag gcagagcttg atcgacagtg gaagaaaata      660
agtgcaatca ttgagaagag gaagaggatg gaagcagatg gggtcgaagt gaaaagacca      720
aagtac                                                                 726

<210> SEQ ID NO 10
<211> LENGTH: 242
<212> TYPE: PRT
<213> ORGANISM: Artificial Sequence
<220> FEATURE:
<223> OTHER INFORMATION: Mutated partial IK factor

<400> SEQUENCE: 10

```
Met Asn Ile Phe Glu Asp Ile Gly Asp Tyr Val Pro Ser Thr Thr Lys
1               5                   10                  15

Thr Pro Arg Asp Lys Glu Arg Glu Tyr Arg Glu Arg Glu Arg Asp
            20                  25                  30

Arg Glu Arg Asp Arg Asp Arg Glu Arg Asp Arg Glu Arg Asp Arg Glu
            35                  40                  45

Arg Glu Arg Glu Arg Asp Arg Glu Arg Glu Glu Glu Lys Lys
        50                  55                  60

Arg His Ser Tyr Phe Glu Lys Pro Lys Val Asp Asp Glu Pro Met Asp
65              70                  75                  80

Val Asp Lys Gly Pro Gly Ser Ala Lys Glu Leu Ile Lys Ser Ile Asn
                85                  90                  95

Glu Lys Phe Ala Gly Ser Ala Gly Trp Glu Gly Thr Glu Ser Leu Lys
            100                 105                 110

Lys Pro Glu Asp Lys Lys Gln Leu Gly Asp Phe Phe Gly Met Ser Asn
        115                 120                 125

Ser Tyr Ala Glu Cys Tyr Pro Ala Thr Met Asp Asp Met Ala Val Asp
130                 135                 140

Ser Asp Glu Glu Val Asp Tyr Ser Lys Met Asp Gln Gly Asn Lys Lys
145                 150                 155                 160

Gly Pro Leu Gly Arg Trp Asp Phe Asp Thr Gln Glu Glu Tyr Ser Glu
                165                 170                 175

Phe Met Asn Asn Lys Glu Ala Leu Pro Lys Ala Ala Phe Gln Tyr Gly
            180                 185                 190

Ile Lys Met Ser Glu Gly Arg Lys Thr Arg Arg Phe Lys Glu Thr Asn
        195                 200                 205

Asp Lys Ala Glu Leu Asp Arg Gln Trp Lys Lys Ile Ser Ala Ile Ile
210                 215                 220

Glu Lys Arg Lys Arg Met Glu Ala Asp Gly Val Glu Val Lys Arg Pro
225                 230                 235                 240

Lys Tyr
```

<210> SEQ ID NO 11
<211> LENGTH: 726
<212> TYPE: DNA
<213> ORGANISM: Artificial Sequence
<220> FEATURE:
<223> OTHER INFORMATION: Mutated partial IK factor

<400> SEQUENCE: 11

| | | | | | | |
|---|---|---|---|---|---|---|
| atgaacattt | ttgaagacat | tggggattac | gttccttcta | caaccaagac | acctcgggac | 60 |
| aaggaacgtg | agagataccg | ggaacgtgaa | cgtgatcggg | aacgggacag | agacagggag | 120 |
| cgagacaggg | agcgagaccg | tgagagggag | agagagcgag | accgggaacg | ggaacgagag | 180 |
| gaggaaaaga | aaaggcacag | ctactttgag | aagccaaaag | tggatgatga | gcccatggat | 240 |
| gttgacaaag | gacctggatc | tgcaaaagag | ttgatcaagt | ccatcaatga | aaaattcgct | 300 |
| gggtctgctg | gctgggaagg | cactgaatcg | ttgaagaagc | cagaagataa | gaagcagctg | 360 |
| ggcgatttct | ttggcatgtc | caacagttac | gcagaatgct | atccagccac | gatggatgac | 420 |
| atggctgtag | atagtgatga | agaggtagat | tatagcaaaa | tggaccaggg | taacaagaag | 480 |
| ggtcccttag | gccgctggga | cttcgatact | caggaggaat | tcagcgagtt | catgaacaac | 540 |

```
aaggaggctc tgcccaaggc tgcattccag tatggcatca agatgtctga aggacggaaa      600
accagacgat tcaaagaaac caatgataag gcagagcttg atcgacagtg aagaaaata      660 agtgcaatca ttgagaagag gaagaggatg gaagcagatg gggtcgaagt gaaaagacca     720
aagtac                                                                726
```

```
<210> SEQ ID NO 12
<211> LENGTH: 242
<212> TYPE: PRT
<213> ORGANISM: Artificial Sequence
<220> FEATURE:
<223> OTHER INFORMATION: Mutated partial IK factor

<400> SEQUENCE: 12
```

```
Met Asn Ile Phe Glu Asp Ile Gly Asp Tyr Val Pro Ser Thr Thr Lys
1               5                   10                  15

Thr Pro Arg Asp Lys Glu Arg Glu Tyr Arg Glu Arg Glu Arg Asp
            20                  25                  30

Arg Glu Arg Asp Arg Asp Arg Glu Arg Asp Arg Glu Arg Asp Arg Glu
        35                  40                  45

Arg Glu Arg Glu Arg Asp Arg Glu Arg Glu Glu Lys Lys
    50                  55                  60

Arg His Ser Tyr Phe Glu Lys Pro Lys Val Asp Asp Glu Pro Met Asp
65                  70                  75                  80

Val Asp Lys Gly Pro Gly Ser Ala Lys Glu Leu Ile Lys Ser Ile Asn
                85                  90                  95

Glu Lys Phe Ala Gly Ser Ala Gly Trp Glu Gly Thr Glu Ser Leu Lys
            100                 105                 110

Lys Pro Glu Asp Lys Lys Gln Leu Gly Asp Phe Phe Gly Met Ser Asn
        115                 120                 125

Ser Tyr Ala Glu Cys Tyr Pro Ala Thr Met Asp Asp Met Ala Val Asp
    130                 135                 140

Ser Asp Glu Glu Val Asp Tyr Ser Lys Met Asp Gln Gly Asn Lys Lys
145                 150                 155                 160

Gly Pro Leu Gly Arg Trp Asp Phe Asp Thr Gln Glu Glu Phe Ser Glu
                165                 170                 175

Phe Met Asn Asn Lys Glu Ala Leu Pro Lys Ala Ala Phe Gln Tyr Gly
            180                 185                 190

Ile Lys Met Ser Glu Gly Arg Lys Thr Arg Arg Phe Lys Glu Thr Asn
        195                 200                 205

Asp Lys Ala Glu Leu Asp Arg Gln Trp Lys Lys Ile Ser Ala Ile Ile
    210                 215                 220

Glu Lys Arg Lys Arg Met Glu Ala Asp Gly Val Glu Val Lys Arg Pro
225                 230                 235                 240

Lys Tyr
```

```
<210> SEQ ID NO 13
<211> LENGTH: 726
<212> TYPE: DNA
<213> ORGANISM: Artificial Sequence
<220> FEATURE:
<223> OTHER INFORMATION: Mutated partial IK factor

<400> SEQUENCE: 13
atgaacattt ttgaagacat tggggattac gttccttcta caaccaagac acctcgggac     60
aaggaacgtg agagataccg ggaacgtgaa cgtgatcggg aacgggacag agacagggag    120
```

```
cgagacaggg agcgagaccg tgagagggag agagagcgag accgggaacg ggaacgagag      180
gaggaaaaga aaaggcacgc ctactttgag aagccaaaag tggatgatga gcccatggat      240
gttgacaaag gacctggatc tgcaaaagag ttgatcaagt ccatcaatga aaaattcgct      300
gggtctgctg gctgggaagg cactgaatcg ttgaagaagc agaagataa gaagcagctg      360 ggcgatttct ttggcatgtc caacagttac gcagaatgct atccagccac gatggatgac      420
atggctgtag atagtgatga agaggtagat tatagcaaaa tggaccaggg taacaagaag      480
ggtcccttag ccgctgggac cttcgatact caggaggaat cagcgagtt catgaacaac      540 aaggaggctc tgcccaaggc tgcattccag tatggcatca gatgtctga aggacggaaa      600 accagacgat tcaaagaaac caatgataag gcagagcttg atcgacagtg gaagaaaata      660
agtgcaatca ttgagaagag gaagaggatg gaagcagatg gggtcgaagt gaaaagacca      720
aagtac                                                                726
```

<210> SEQ ID NO 14
<211> LENGTH: 242
<212> TYPE: PRT
<213> ORGANISM: Artificial Sequence
<220> FEATURE:
<223> OTHER INFORMATION: Mutated partial IK factor

<400> SEQUENCE: 14

```
Met Asn Ile Phe Glu Asp Ile Gly Asp Tyr Val Pro Ser Thr Thr Lys
1               5                   10                  15

Thr Pro Arg Asp Lys Glu Arg Glu Arg Tyr Arg Glu Arg Glu Arg Asp
            20                  25                  30

Arg Glu Arg Asp Arg Asp Arg Glu Arg Asp Arg Glu Arg Asp Arg Glu
        35                  40                  45

Arg Glu Arg Glu Arg Asp Arg Glu Arg Glu Glu Glu Lys Lys
    50                  55                  60

Arg His Ala Tyr Phe Glu Lys Pro Lys Val Asp Asp Glu Pro Met Asp
65                  70                  75                  80

Val Asp Lys Gly Pro Gly Ser Ala Lys Glu Leu Ile Lys Ser Ile Asn
                85                  90                  95

Glu Lys Phe Ala Gly Ser Ala Gly Trp Glu Gly Thr Glu Ser Leu Lys
            100                 105                 110

Lys Pro Glu Asp Lys Lys Gln Leu Gly Asp Phe Phe Gly Met Ser Asn
        115                 120                 125

Ser Tyr Ala Glu Cys Tyr Pro Ala Thr Met Asp Met Ala Val Asp
    130                 135                 140

Ser Asp Glu Glu Val Asp Tyr Ser Lys Met Asp Gln Gly Asn Lys Lys
145                 150                 155                 160

Gly Pro Leu Gly Arg Trp Asp Phe Asp Thr Gln Glu Glu Phe Ser Glu
                165                 170                 175

Phe Met Asn Asn Lys Glu Ala Leu Pro Lys Ala Ala Phe Gln Tyr Gly
            180                 185                 190

Ile Lys Met Ser Glu Gly Arg Lys Thr Arg Arg Phe Lys Glu Thr Asn
        195                 200                 205

Asp Lys Ala Glu Leu Asp Arg Gln Trp Lys Lys Ile Ser Ala Ile Ile
    210                 215                 220

Glu Lys Arg Lys Arg Met Glu Ala Asp Gly Val Glu Val Lys Arg Pro
225                 230                 235                 240

Lys Tyr
```

<210> SEQ ID NO 15
<211> LENGTH: 56
<212> TYPE: DNA
<213> ORGANISM: Artificial Sequence
<220> FEATURE:
<223> OTHER INFORMATION: Primer for tIK factor

<400> SEQUENCE: 15
ggtggaattc atgtatcctt atgatgttcc tgattatgct atgatgaaca tttttg      56

<210> SEQ ID NO 16
<211> LENGTH: 33
<212> TYPE: DNA
<213> ORGANISM: Artificial Sequence
<220> FEATURE:
<223> OTHER INFORMATION: primer for tIK factor

<400> SEQUENCE: 16
ctagactcga ggtactttgg tcttttcact tcg      33

<210> SEQ ID NO 17
<211> LENGTH: 30
<212> TYPE: DNA
<213> ORGANISM: Artificial Sequence
<220> FEATURE:
<223> OTHER INFORMATION: Primer for mutated IK factor

<400> SEQUENCE: 17
ggtggaattc atgtatcctt atgatgttcc      30

<210> SEQ ID NO 18
<211> LENGTH: 30
<212> TYPE: DNA
<213> ORGANISM: Artificial Sequence
<220> FEATURE:
<223> OTHER INFORMATION: primer for mutated IK factor

<400> SEQUENCE: 18
ggtgaagctt atgtatcctt atgatgttcc      30

<210> SEQ ID NO 19
<211> LENGTH: 33
<212> TYPE: DNA
<213> ORGANISM: Artificial Sequence
<220> FEATURE:
<223> OTHER INFORMATION: Primer for mutated IK factor

<400> SEQUENCE: 19
ggcttctcaa agtaggcgtg ccttttcttt tcc      33

<210> SEQ ID NO 20
<211> LENGTH: 33
<212> TYPE: DNA
<213> ORGANISM: Artificial Sequence
<220> FEATURE:
<223> OTHER INFORMATION: Primer for mutated IK factor

<400> SEQUENCE: 20
ggaaaagaaa aggcacgcct actttgagaa gcc      33

<210> SEQ ID NO 21
<211> LENGTH: 25
<212> TYPE: DNA
<213> ORGANISM: Artificial Sequence
<220> FEATURE:
<223> OTHER INFORMATION: Primer for mutated IK factor

<400> SEQUENCE: 21
ctcgctgaat tcctcctgag tatcg                                  25

<210> SEQ ID NO 22
<211> LENGTH: 25
<212> TYPE: DNA
<213> ORGANISM: Artificial Sequence
<220> FEATURE:
<223> OTHER INFORMATION: Primer for mutated IK factor

<400> SEQUENCE: 22
cgatactcag gaggaattca gcgag                                  25

<210> SEQ ID NO 23
<211> LENGTH: 25
<212> TYPE: DNA
<213> ORGANISM: Artificial Sequence
<220> FEATURE:
<223> OTHER INFORMATION: Primer for mutated IK factor

<400> SEQUENCE: 23
cctccttgtt gttcatgaac tcgct                                  25

<210> SEQ ID NO 24
<211> LENGTH: 29
<212> TYPE: DNA
<213> ORGANISM: Artificial Sequence
<220> FEATURE:
<223> OTHER INFORMATION: Primer for mutated IK factor

<400> SEQUENCE: 24
ggaatacagc gagttcatga acaacaagg                              29

<210> SEQ ID NO 25
<211> LENGTH: 22
<212> TYPE: DNA
<213> ORGANISM: Artificial Sequence
<220> FEATURE:
<223> OTHER INFORMATION: Primer for mutated IK factor

<400> SEQUENCE: 25
gttcatgaac tcgctgaatt cc                                     22

<210> SEQ ID NO 26
<211> LENGTH: 27
<212> TYPE: DNA
<213> ORGANISM: Artificial Sequence
<220> FEATURE:
<223> OTHER INFORMATION: Primer for mutated IK factor

<400> SEQUENCE: 26
caggaggaat tcagcgagtt catgaac                                27

<210> SEQ ID NO 27
<211> LENGTH: 20
<212> TYPE: DNA
<213> ORGANISM: Artificial Sequence
<220> FEATURE:

```
<223> OTHER INFORMATION: Primer for CDCA3

<400> SEQUENCE: 27
tggtattgca cggacaccta                                               20

<210> SEQ ID NO 28
<211> LENGTH: 20
<212> TYPE: DNA
<213> ORGANISM: Artificial Sequence
<220> FEATURE:
<223> OTHER INFORMATION: Primer for CDCA3

<400> SEQUENCE: 28
gttccaaggt ggcatctgtt                                               20

<210> SEQ ID NO 29
<211> LENGTH: 20
<212> TYPE: DNA
<213> ORGANISM: Artificial Sequence
<220> FEATURE:
<223> OTHER INFORMATION: Primer for CNOT1

<400> SEQUENCE: 29
cgagccaagt gctatcacaa                                               20

<210> SEQ ID NO 30
<211> LENGTH: 20
<212> TYPE: DNA
<213> ORGANISM: Artificial Sequence
<220> FEATURE:
<223> OTHER INFORMATION: Primer for CNOT1

<400> SEQUENCE: 30
tgctcaggtg cattgagttc                                               20

<210> SEQ ID NO 31
<211> LENGTH: 20
<212> TYPE: DNA
<213> ORGANISM: Artificial Sequence
<220> FEATURE:
<223> OTHER INFORMATION: Primer for MAPK1

<400> SEQUENCE: 31
ccagaccatg atcacacagg                                               20

<210> SEQ ID NO 32
<211> LENGTH: 20
<212> TYPE: DNA
<213> ORGANISM: Artificial Sequence
<220> FEATURE:
<223> OTHER INFORMATION: Primer for MAPK1

<400> SEQUENCE: 32
ctggaaagat gggcctgtta                                               20

<210> SEQ ID NO 33
<211> LENGTH: 30
<212> TYPE: DNA
<213> ORGANISM: Artificial Sequence
<220> FEATURE:
<223> OTHER INFORMATION: Primer for tIK-TG

<400> SEQUENCE: 33
ccctattgac gtcaatgacg gtaaatgcgg                                    30
```

```
<210> SEQ ID NO 34
<211> LENGTH: 30
<212> TYPE: DNA
<213> ORGANISM: Artificial Sequence
<220> FEATURE:
<223> OTHER INFORMATION: Primer for tIK-TG

<400> SEQUENCE: 34
ccgtccttca gacatcttga tgccatactg                                    30

<210> SEQ ID NO 35
<211> LENGTH: 21
<212> TYPE: DNA
<213> ORGANISM: Artificial Sequence
<220> FEATURE:
<223> OTHER INFORMATION: Primer for RaKO

<400> SEQUENCE: 35
tcagggttga cagcgacagc a                                             21

<210> SEQ ID NO 36
<211> LENGTH: 24
<212> TYPE: DNA
<213> ORGANISM: Artificial Sequence
<220> FEATURE:
<223> OTHER INFORMATION: Primer for RaKO mouse

<400> SEQUENCE: 36
gactgccttg ggaaaagcgc ctcc                                          24

<210> SEQ ID NO 37
<211> LENGTH: 20
<212> TYPE: DNA
<213> ORGANISM: Artificial Sequence
<220> FEATURE:
<223> OTHER INFORMATION: Primer for RaKO mouse

<400> SEQUENCE: 37
gggtccccag cagatttcca                                               20

<210> SEQ ID NO 38
<211> LENGTH: 21
<212> TYPE: DNA
<213> ORGANISM: Artificial Sequence
<220> FEATURE:
<223> OTHER INFORMATION: Primer for IL-1b

<400> SEQUENCE: 38
tgtaatgaaa gacggcacac c                                             21

<210> SEQ ID NO 39
<211> LENGTH: 21
<212> TYPE: DNA
<213> ORGANISM: Artificial Sequence
<220> FEATURE:
<223> OTHER INFORMATION: Primer for IL-1b

<400> SEQUENCE: 39
tcttctttgg gtattgcttg g                                             21

<210> SEQ ID NO 40
<211> LENGTH: 22
<212> TYPE: DNA
<213> ORGANISM: Artificial Sequence
<220> FEATURE:
<223> OTHER INFORMATION: Primer for IL-6
```

```
<400> SEQUENCE: 40
gagaaaagag ttgtgcaatg gc                                              22

<210> SEQ ID NO 41
<211> LENGTH: 21
<212> TYPE: DNA
<213> ORGANISM: Artificial Sequence
<220> FEATURE:
<223> OTHER INFORMATION: Primer for IL-6

<400> SEQUENCE: 41
ccagtttggt agcatccatc a                                               21

<210> SEQ ID NO 42
<211> LENGTH: 20
<212> TYPE: DNA
<213> ORGANISM: Artificial Sequence
<220> FEATURE:
<223> OTHER INFORMATION: Primer for IL-17A

<400> SEQUENCE: 42
tccagaaggc cctcagacta                                                 20

<210> SEQ ID NO 43
<211> LENGTH: 20
<212> TYPE: DNA
<213> ORGANISM: Artificial Sequence
<220> FEATURE:
<223> OTHER INFORMATION: Primer for IL-17A

<400> SEQUENCE: 43
agcatcttct cgaccctgaa                                                 20

<210> SEQ ID NO 44
<211> LENGTH: 18
<212> TYPE: DNA
<213> ORGANISM: Artificial Sequence
<220> FEATURE:
<223> OTHER INFORMATION: Primer for MCP-1

<400> SEQUENCE: 44
catccacgtg ttggctca                                                   18

<210> SEQ ID NO 45
<211> LENGTH: 23
<212> TYPE: DNA
<213> ORGANISM: Artificial Sequence
<220> FEATURE:
<223> OTHER INFORMATION: Primer for MCP-1

<400> SEQUENCE: 45
gatcatcttg ctggtgaatg agt                                             23

<210> SEQ ID NO 46
<211> LENGTH: 42
<212> TYPE: DNA
<213> ORGANISM: Artificial Sequence
<220> FEATURE:
<223> OTHER INFORMATION: nucleid acids encoding mutant partial IK
      peptide

<400> SEQUENCE: 46
gaaaagaaaa ggcacagcta ctttgagaag ccaaaagtgg at                        42

<210> SEQ ID NO 47
```

```
<211> LENGTH: 14
<212> TYPE: PRT
<213> ORGANISM: Artificial Sequence
<220> FEATURE:
<223> OTHER INFORMATION: Mutant partial IK peptide

<400> SEQUENCE: 47

Glu Lys Lys Arg His Ser Tyr Phe Glu Lys Pro Lys Val Asp
1               5                   10

<210> SEQ ID NO 48
<211> LENGTH: 39
<212> TYPE: DNA
<213> ORGANISM: Artificial Sequence
<220> FEATURE:
<223> OTHER INFORMATION: Nucleic aicds encoding mutant partial IK
      peptide

<400> SEQUENCE: 48
gatactcagg aggaatacag cgagtacatg aacaacaag                              39

<210> SEQ ID NO 49
<211> LENGTH: 13
<212> TYPE: PRT
<213> ORGANISM: Artificial Sequence
<220> FEATURE:
<223> OTHER INFORMATION: Mutant partial IK peptide

<400> SEQUENCE: 49

Asp Thr Gln Glu Glu Tyr Ser Glu Tyr Met Asn Asn Lys
1               5                   10

<210> SEQ ID NO 50
<211> LENGTH: 15
<212> TYPE: DNA
<213> ORGANISM: Artificial Sequence
<220> FEATURE:
<223> OTHER INFORMATION: FC tagging

<400> SEQUENCE: 50
ctggttccgc gtggt                                                        15

<210> SEQ ID NO 51
<211> LENGTH: 702
<212> TYPE: DNA
<213> ORGANISM: Artificial Sequence
<220> FEATURE:
<223> OTHER INFORMATION: Fc tagging

<400> SEQUENCE: 51
tccgagccca aatcttgtga caaaactcac acatgcccac cgtgcccagc acctgaactc        60
ctggggggac cgtcagtctt cctcttcccc ccaaaaccca aggacaccct catgatctcc       120
cggacccctg aggtcacatg cgtggtggtg gacgtgagcc acgaagaccc tgaggtcaag       180
ttcaactggt acgtggacgg cgtggaggtg cataatgcca agacaaagcc gcggaggag        240 cagtacaaca gcacgtaccg tgtggtcagc gtcctcaccg tcctgcacca ggactggctg       300
aatggcaagg agtacaagtg caaggtctcc aacaaagccc tcccagcccc catcgagaaa      360
accatctcca aagccaaagg gcagcccga gaaccacagg tgtacaccct gcccccatcc        420
cgggatgagc tgaccaagaa ccaggtcagc ctgacctgcc tggtcaaagg cttctatccc       480
agcgacatcg ccgtggagtg ggagagcaat gggcagccgg agaacaacta caagaccacg       540
cctcccgtgc tggactccga cggctccttc ttcctctaca gcaagctcac cgtggacaag       600
```
agcaggtggc agcaggggaa cgtcttctca tgctccgtga tgcatgaggc tctgcacaac    660
cactacacgc agaagagcct ctccctgtct ccgggtaaat ga    702

<210> SEQ ID NO 52
<211> LENGTH: 33
<212> TYPE: DNA
<213> ORGANISM: Artificial Sequence
<220> FEATURE:
<223> OTHER INFORMATION: Primer for tIK-FA-PAc

<400> SEQUENCE: 52
gaggcggatc ccaacatttt tgaagacatt ggg    33

<210> SEQ ID NO 53
<211> LENGTH: 36
<212> TYPE: DNA
<213> ORGANISM: Artificial Sequence
<220> FEATURE:
<223> OTHER INFORMATION: Primer for tIK-FA-PAc

<400> SEQUENCE: 53
gctgggcggc cgcgtacttt ggtcttttca cttcga    36

<210> SEQ ID NO 54
<211> LENGTH: 27
<212> TYPE: DNA
<213> ORGANISM: Artificial Sequence
<220> FEATURE:
<223> OTHER INFORMATION: HA tagging sequence

<400> SEQUENCE: 54
tatccttatg atgttcctga ttatgct    27

<210> SEQ ID NO 55
<211> LENGTH: 30
<212> TYPE: DNA
<213> ORGANISM: Artificial Sequence
<220> FEATURE:
<223> OTHER INFORMATION: Primer for AAV and CHO

<400> SEQUENCE: 55
ggtggaattc atgtatcctt atgatgttcc    30

<210> SEQ ID NO 56
<211> LENGTH: 29
<212> TYPE: DNA
<213> ORGANISM: Artificial Sequence
<220> FEATURE:
<223> OTHER INFORMATION: Primer for AAV

<400> SEQUENCE: 56
ctagaaagct tgtactttgg tcttttcac    29

<210> SEQ ID NO 57
<211> LENGTH: 33
<212> TYPE: DNA
<213> ORGANISM: Artificial Sequence
<220> FEATURE:
<223> OTHER INFORMATION: Primer for CHO

<400> SEQUENCE: 57
ctagactcga ggtactttgg tcttttcact tcg    33

METHOD FOR TREATING ARTHRITIS USING IK FACTOR OR NUCLEIC ACID ENCODING IK FACTOR

CROSS-REFERENCE TO RELATED APPLICATIONS

This application is a US National Phase filing of PCT/KR2014/003282, filed on Apr. 16, 2014, which claims benefit of 10-2013-0041771 KR filed on Apr. 16, 2013 and 10-2014-0038809 KR, filed on Apr. 1, 2014. The disclosure of which is expressly incorporated entirely by reference.

ACKNOWLEDGEMENTS

This invention was funded by the Ministry of Trade, Industry and Energy (MOTIE) of the Republic of Korea under Grant No. 10052915.

FIELD OF THE INVENTION

The present invention relates to a pharmaceutical use of a peptide derived from a living body and a nucleic acid encoding the peptide, more particularly to a pharmaceutical use of IK factor or fragments of IK factor and/or a nucleic acid encoding IK factor or the fragments of IK factor.

BACKGROUND ART

Arthritis is a disorder accompanied by joint stiffness and continuous periarticular pains caused by one or more joint inflammations. Arthritis can be classified into an acute arthritis and a chronic arthritis. The chronic arthritis such as gouty arthritis, polyarthritis, rheumatoid arthritis and osteoarthritis deformans caused by aging of bones or joints results in continuous periarticular pains.

Rheumatoid arthritis among the chronic arthritis is a chronic inflammatory disorder of unknown cause characterized by polyarthritis. The exact cause of the rheumatoid arthritis has not been known up to date. But, it has been generally considered that a hereditary tendency, bacterial or viral infections and the likes induce the rheumatoid arthritis to develop and inferred that hormones are concerned in developing the rheumatoid arthritis. The rheumatoid arthritis has harmful influences on not only joints but also other organs of the body. Accordingly, patients who have induced rheumatoid arthritis cannot walk and use their own hands or feet, and frequently feel tired or unpleasant. Furthermore, rheumatoid arthritis cause weight loss, lack of sleep and the likes, and continuous rheumatoid arthritis results in limitation of physical activity of the patients caused by muscular weakening, and thereby, considerably influencing on private and social activities of the patients. Also, when the physical activity of the patients is limited caused by rheumatoid arthritis, it is highly likely that the patients become obese and suffer from heart disease resulted from high cholesterol level and get the blues.

Rheumatoid arthritis has been occurred 0.2 cases for every 1,000 people for men and 0.4 cases per 1,000 persons for women per year, and prevalence of rheumatoid arthritis is 0.4-1.4%, which shows relatively even distribution in worldwide. As the aging population has increased gradually, it is expected that the market of therapeutic agents for rheumatoid arthritis grow sharply.

Currently, non-steroidal anti-inflammatory drugs (NSAID); steroids; non-biological disease-modifying anti-rheumatoid drugs (DMARD) such as anti-malarial drugs, hydroxychloroquinone (HCQ), sulfasalazine, methotrexate (MTX), leflunomide; and biological anti-rheumatoid drugs such as tumor necrosis factor (TNF) inhibitors or IL-6 inhibitors have been used as therapeutic agents for rheumatoid arthritis.

As the biological anti-rheumatoid drugs, tumor necrosis factor (TNF) inhibitors such as etanercept, adalimumab, infliximab, golimumab and certolizumab; monoclonal antibody Rituximab as a B-cell inhibitor; Abatacept blocking immune responses between antigen-presenting cells and T-cell; Tofacitinib blocking selectively JAK (Janus activated kinase) as a small molecule inhibitor and the likes have been developed.

But, most of those therapeutic agents for rheumatoid arthritis induce severe side effects. For example, non-steroidal anti-inflammatory drugs have caused gastrointestinal side effects, and some non-steroidal anti-inflammatory drugs including selective COX-2 inhibitors may induce severe side effects in cardiovascular system. Besides, it has been known that non-steroidal anti-inflammatory drugs induce side effects such as decline in renal function, interstitial nephritis, an acute renal failure and the likes. When administering steroids for a long term, they cause atrophy of hypothalamus-pituitary gland-adrenal gland so that adrenal insufficiency may be occurred, and they induce other side effects such as glaucoma, cataract, osteonecrosis, osteoporosis, hypertension, hypokalemia, and the likes. Particularly, because the non-steroidal anti-inflammatory drugs and steroids do not suppress of the progression of arthritis in reality, but only alleviates inflammation, they show little effects with regard to preventing joint damages.

Meanwhile, currently developed anti-rheumatoid drugs can suppress of the progression of early rheumatoid arthritis, but they cannot cure completely rheumatoid arthritis. Also, it has been reported that anti-rheumatoid drugs can induce some side effects. For example, some non-biological anti-rheumatoid drugs can induce side effects such as visual disturbance, retinopathy, skin rash, hepatic dysfunction, nausea and the likes. Also, tumor necrosis factor inhibitors of biological anti-rheumatoid drugs have problems such as blood abnormality, heart failure, hepatic dysfunction and opportunistic infection and IL-6 inhibitors can cause side effects such as hepatic dysfunction, leucopenia and the likes. It has been reported that other biological anti-rheumatoid drugs can induce infection problems as well as side effects such as a risk of tumorigenesis, gastrointestinal perforation and hyperlipidemia.

Particularly, most of the biological anti-rheumatoid drugs have a fatal defect that they can be administered only through subcutaneous injection or intravascular injection, and induce response decline to the drugs owing to immunogenicity by the human body by lapse of time. Also, since the currently developed biological anti-rheumatoid drugs suppress general immune system, they are exposed to the vulnerability of opportunistic infections and cancer suppression. Furthermore, those biological anti-rheumatoid drugs are very expensive, which causes financial burdens of patients considerably. Particularly, not a few patients with rheumatoid arthritis do no react to monoclonal antibodies which have been used as a representative biological anti-rheumatoid drug.

DETAILED DESCRIPTION OF THE INVENTION

Technical Problem

The present invention is proposed for solving the problem of the prior art, and an object of the present invention is to provide a pharmaceutical composition for treating or preventing arthritis that assures safety since no side effects and toxicity to a living body in spite of long-term administering.

Another object of the present invention is to provide a pharmaceutical composition for treating or preventing arthritis that shows no efficiency avoidances, and facilitate cheap manufacture in large quantity so as to lower patients' burden.

Technical Solution

The present invention provides a pharmaceutical composition for treating or preventing arthritis comprises a pharmaceutically effective amount of IK factor or fragments of IK factor.

In an exemplary embodiment, the fragments of IK factor comprises a peptide having an amino acid sequence of SEQ ID NO: 4 or a partial peptide of SEQ ID NO: 4.

For example, the fragments of IK factor may comprise a peptide having 10 or more amino acids that comprises at least one amino acid residue selected from Serine 382, Tyrosine 489 and Tyrosine 492 of SEQ ID NO: 2 and amino acids adjacent to the selected amino acid residue.

For example, the at least one amino acid residue consisting of Serine 382, Tyrosine 489 and Tyrosine 492 of SEQ ID NO: 2 consisting of the fragments of IK factor is phosphorylated.

In an alternative embodiment, the fragments of IK factor are fragments of a peptide having amino acids of SEQ ID NO: 2, wherein the fragment of the peptide has 10 or more amino acids that comprises at least one amino acid residue selected from Serine 382 and Tyrosine 489 of SEQ ID NO: 2 and amino acids adjacent to the selected amino acid residue.

In a concrete embodiment, the fragments of IK factor comprise a peptide having 10 or more amino acids that comprise two or more adjacent amino acids bonded to each of N-terminal and C-terminal of the selected amino acid residue.

In an exemplary embodiment, the fragments of IK factor comprise a peptide having amino acids selected from the group consisting of at least one of SEQ ID NO: 4, SEQ ID NO: 47 and SEQ ID NO: 49.

The pharmaceutical composition containing IK factor or the fragments of IK factor may be used in treating rheumatoid arthritis.

In an exemplary embodiment, IK factor or the fragments of IK factor may be contained in an amount of 1.0 ng/mL to 10 µg/mL in the pharmaceutical composition.

Besides, the present invention provides a pharmaceutical composition for treating or preventing arthritis comprises a pharmaceutically effective amount of a gene delivery vehicle that comprises a nucleic acid molecule encoding IK factor or fragments of IK factor.

For example, the nucleic acid molecule encoding the fragments of IK factor comprises a nucleic acid having a base sequence of SEQ ID NO: 3 or a partial nucleic acid of SEQ ID NO: 3.

In an exemplary embodiment, the nucleic acid molecule encoding the fragments of IK factor may comprise a nucleic acid having 30 or more nucleotides that comprises at least one nucleotide residue set selected from nucleotide residues 1144-1166, nucleotide residues 1465-1467 and nucleotide residues 1474-1476 of a base sequence of SEQ ID NO: 1 and nucleotides adjacent to the selected nucleotide residue set.

In one exemplary embodiment, the nucleic acid molecule encoding the fragments of IK factor may comprise a nucleic acid having 30 or more nucleotides that comprises at least one nucleotide residue set selected from nucleotide residues 1144-1166 and nucleotide residues 1465-1467 of SEQ ID NO: 1 and nucleotides adjacent to the selected nucleotide residue set.

In a concrete embodiment, the nucleic acid molecule encoding the fragments of IK factor may comprise a nucleic acid having 30 or more nucleotides that comprises at least six adjacent nucleotides bonded to each of 5'-end and 3'-end of the selected nucleic acid residue set.

In an exemplary embodiment, the nucleic acid molecule encoding the fragments of IK factor comprises a nucleotide sequence encoding a peptide having an amino acid sequence selected from the group consisting of at least one of SEQ ID NO: 4, SEQ ID NO: 47 and SEQ ID NO: 49.

For example, the nucleic acid molecule encoding the fragments of IK factor may comprise a nucleotide sequence selected from the group consisting of at least one of SEQ ID NO: 3, SEQ ID NO: 46 and SEQ ID NO: 48.

The nucleic acid molecule encoding IK factor or the fragments of IK factor may be used in treating rheumatoid arthritis.

In an exemplary embodiment, the nucleic acid molecule encoding IK factor or the fragments of IK factor may be contained in an amount of 1.0 ng/mL to 10 µg/mL in the pharmaceutical composition.

For example, the gene delivery vehicle may have a naked nucleic acid molecule, a plasmid, a viral vector, or a liposome or a niosome containing the viral vector.

In this case, the viral vector may be selected from the group consisting of Adenovirus, Adeno associated virus, Retrovirus, Lentivirus, Baculovirus, herpes simplex virus and vaccinia virus.

Also, the present invention relates to IK factor or fragments of IK factor, a nucleic acid encoding IK factor or the fragments of IK factor and/or a vector or a gene delivery vehicle having the nucleic acid for treating arthritis.

Furthermore, the present invention relates to a method of treating arthritis comprises administering a therapeutically effective amount or a pharmaceutically effective amount of IK factor or the fragments of IK factor, a nucleic acid encoding IK factor or the fragments of IK factor, and/or a vector or a gene delivery vehicle having the nucleic acid to a subject.

Technical Effect of the Invention

According to the present invention, IK factor or the fragments of IK factor and/or a nucleic acid encoding IK factor or the fragments of IK factor are involved in reaction mechanism in an upstream level with relation to arthritis, for example rheumatoid arthritis, and suppress the progression of rheumatoid arthritis.

IK factor or the fragments of IK factor and/or a nucleic acid encoding thereof used as an active ingredient in the composition are immune-regulatory molecules in a human body that regulates generally activities of immunocytes having effects on arthritis so that they can be administered safely into the human body.

Particularly, because IK factor and/or the fragments thereof is an intrinsic molecule generated in the human body, and therefore, they shows little immunogenicity and are not involved with whole population of the immunocytes, it is expected that no side effects are occurred in spite of administering them for a long time.

Besides, it is possible to manufacture the pharmaceutical composition cheaply compared to the existing therapeutic agents for rheumatoid arthritis, for example, monoclonal antibodies. Furthermore, it is expected that the pharmaceutical composition of the invention can solve the problem of efficiency avoidance that is induced by the existing therapeutic drugs for rheumatoid arthritis.

BRIEF DESCRIPTION OF THE DRAWINGS

FIG. 1 is a schematic diagram shows a location of a full-length cDNA encoding IK factor and a truncated IK nucleic acid fragment (tIK fragment) which only has nucleotides at C-terminal of the full-length cDNA and excises nucleotides at N-terminal form the full-length cDNA. In FIG. 1, "HA" indicates haemagglutinin tag;

Upper portion of FIG. 2 is a schematic diagram shows a location of nucleotides consisting of truncated IK nucleic acid fragment (tIK fragment) that some nucleotides are excised from the full-length IK factor based upon nucleotides encoding full-length IK factor according to an exemplary embodiment of the present invention. Lower portion of FIG. 2 is a schematic diagram shows locations of amino acids and kinds of amino acids at activated sites which are expected to be involved in physical functions of IK factor based upon an exemplary amino acid sequence of full-length IK factor with regard to manufacturing variant IK factor. In FIG. 2, "HA" indicates haemagglutinin tag;

FIG. 3 are graphs each of which shows an experimental result of measuring an expression suppression level of CNOT1, CDCA3 and MAPK1 each of which is an upstream regulatory factor suppressing CIITA as a MHC Class II transactivator by the expression of truncated IK nucleic acid fragment (tIK) and mutant nucleic acids fragments (S382A, Y489F, Y492F, Y489492F, S382AY489492F) of which some nucleotides of tIK nucleic acids are replaced with other nucleotides. In FIG. 3, "*" indicates P<0.05 compared to a negative control and "#" indicates P<0.05 in case of mutant nucleic acid fragments are expressed compared to an expression of wild-type tIK;

FIG. 4A is a graph shows an experimental result of measuring arthritis index by lapse of time between IL-1 Receptor antagonist knock-out (IL1RaKO) mice as a negative control that was processed to induce arthritis spontaneously, and tIK-IL1RaKO mice that are prepared by cross-breeding the IL1RaKO mouse with a transgenic mouse that expresses truncated IK factor according to the present invention. In FIG. 4A, "*" indicates P<0.05 compared to a negative control, "" indicated P<0.01 compared to a negative control and "*" indicates P<0.001 compared to a negative control;

FIG. 4B is a graph shows an experimental result of measuring arthritis incidence rate by lapse of time between IL1RaKO mice and tIK-IL1RaKO mice;

FIG. 5 is photographs show joints of IL1RaKO mice that were processed to induce arthritis spontaneously, and tIK-IL1RaKO mice that were prepared according to the present invention;

FIG. 6A shows experimental results using H&E staining for the joint tissues extracted from IL1RaKO mice that were processed to induce arthritis spontaneously, and tIK-IL1RaKO mice that were prepared according to the present invention. Left portion of FIG. 6A is a microscopy for the joint tissues of the mice. Right portion of FIG. 6A is a graph shows an analysis result for the inflammation level of the joint tissues. In FIG. 6A, "*" indicates P<0.05 compared to the negative control;

FIG. 6B shows experimental results using safari 0 staining for the joint tissues extracted from IL1RaKO mice that were processed to induce arthritis spontaneously, and tIK-IL1RaKO mice that were prepared according to the present invention. Left portion of FIG. 6B is a microscopy for the joint tissues of the mice. Right portion of FIG. 6B is a graph shows an analysis result for cartridge erosion level in the joint tissues. In FIG. 6A, "*" indicates P<0.05 compared to the negative control;

FIG. 7 is photographs show bone damage levels in the joint tissues extracted from IL1RaKO mice that were processed to induce arthritis spontaneously, and tIK-IL1RaKO mice prepared according to the present invention;

FIG. 8A is graphs each of which shows an experimental result for the expression level of inflammatory cytokine in the joint tissues extracted from IL1 RaKO mice that were processed to induce arthritis spontaneously, and tIK-IL1RaKO mice that were prepared according to the present invention. In FIG. 8A, "*" indicates P<0.05 compared to the negative control and "**" indicates P<0.01 compared to the negative control;

FIG. 8B is photographs each of which shows an expression level of inflammatory cytokine in the joint tissues extracted from IL1RaKO mice that were processed to induce arthritis spontaneously, and tIK-IL1RaKO mice that were prepared according to the present invention;

FIG. 9 is graphs each of which shows an experimental result for the expression level of inflammatory cytokine in the serum extracted from IL1RaKO mice that were processed to induce arthritis spontaneously, and tIK-IL1RaKO mice that were prepared according to the present invention. In FIG. 9, "**" indicates P<0.01 compared to the negative control;

FIG. 10A is plots and a graph each of which shows an experimental result of measuring an amount of Th1 cells as an exemplary pathogenic T-cell in order to examine the differentiation of the pathogenic T-cell in the splenocyte extracted from IL1RaKO mice that were processed to induce arthritis spontaneously, and tIK-IL1RaKO mice that were prepared according to the present invention;

FIG. 10B is plots and a graph each of which shows an experimental result of measuring an amount of Th17 cells as an exemplary pathogenic T-cell in order to examine the differentiation of the pathogenic T-cell in the splenocyte extracted from IL1RaKO mice that were processed to induce arthritis spontaneously, and tIK-IL1RaKO mice that were prepared according to the present invention;

FIG. 11 is graphs each of which shows an experimental result of measuring an amount of macrophage activation factor in the splenocyte extracted from IL1RaKO mice that were processed to induce arthritis spontaneously, and tIK-IL1RaKO mice that were prepared according to the present invention. In FIG. 11, "*" indicated P<0.05 compared to the negative control;

FIG. 12A is graphs each of which shows an experimental result of measuring expression level of inflammatory cytokine in the macrophage which is transfected by peptides comprising amino acids involved in the activation of IK factor according to the present invention. In FIG. 12A, "*" indicates P<0.05 and "**" indicates P<0.01 compared to the negative control;

FIG. 12B is graphs each of which shows an experimental result of measuring expression level of inflammatory cytokine in the cell culture medium containing macrophage which is transfected by peptides comprising amino acids involved in the activation of IK factor according to the present invention. In FIG. 12B, "" indicates P<0.01 and "*" indicates P<0.001 compared to the negative control;

FIG. 13A is plots and a graph each of which shows an experimental result of analyzing differentiation level of Th0 cells in the splenocyte extracted from wild-type mice transfected by peptides comprising amino acids involved in the activation of IK factor according to the present invention;

FIG. 13B is plots and a graph each of which shows an experimental result of analyzing differentiation level of Th1 cells in the splenocyte extracted from wild-type mice transfected by peptides comprising amino acids involved in the activation of tIK factor according to the present invention;

FIG. 13C is plots and a graph each of which shows an experimental result of analyzing differentiation level of Th17 cells in the splenocyte extracted from wild-type mice transfected by a peptide comprising amino acids involved in the activation of tIK factor according to the present invention;

FIG. 14A is a graph shows an experimental result of measuring arthritis index by laps of time of IL1RaKO mice, which are spontaneously induced arthritis mouse model, that was transfected by a peptide comprising amino acids involved in the activation of tIK factor according to the present invention; and FIG. 14B is a graph shows an experimental result of measuring incidence rate of arthritis by lapse of time for the IL1RaKO mice.

FIG. 15A is plots and a graph each of which shows an experimental result of analyzing differentiation level of Th17 cells in the splenocyte extracted from IL1RaKO mice, which are spontaneously induced arthritis mouse model, that was transfected by a peptide comprising amino acids involved in the activation of tIK factor according to the present invention. In FIG. 15A, "*" indicates P<0.05 compared to the negative control;

FIG. 15B is photographs each of which shows an experimental result of showing expression level of inflammatory cytokine in the joint tissue extracted from the negative control mice, which are spontaneously induced arthritis mouse model, that was transfected by a peptide derived from IK factor and then stained according to the present invention;

FIG. 16 is a photograph shows an experimental result of SDS-PAGE assay in order to certify that IK factor was expressed in the insect cell that was transfected by a truncated IK nucleic acid fragment (tIK fragment) containing Fc tag sequence using Baculovirus expression system;

FIG. 17 is Western-blotting assay results each of which shows IK factor was expressed in the Adeno-associated Virus (tIK-AAV) into which a truncated IK gene fragment (gene fragment encoding tIK fragment) containing Ha tag sequence at the 5'-end were inserted;

FIG. 18A is a graph shows an experimental result of measuring arthritis index by lapse of time of IL1RaKO mice, which are spontaneously induced arthritis mouse model, that was transfected by Adeno-associated virus into which a truncated IK gene fragment (gene fragment encoding tIK fragment) was inserted; and FIG. 18B is a graph shows an experimental result of measuring incidence rate of arthritis by lapse of time of the IL1RaKO mice; and FIG. 19 is a Western-blotting assay result that shows IK factor was expressed in the CHO cell into which a plasmid having a truncated IK gene fragment (tIK fragment) containing Ha tag sequence at the 5'-end were inserted.

MODE FOR INVENTION

The inventors examined a new function of IK factor that is a sort of cytokine expressed in living organisms and found that IK factor or fragments thereof or gene delivery vehicles having nucleic acids encoding IK factor or the fragments suppress the progression of arthritis, for example, rheumatoid arthritis and completed the present invention. Hereinafter, the present invention will be described referring to the accompanying drawings.

Definition

As used herein, the term "amino acid" is used in the broadest sense and is intended to include naturally occurring L-amino acids or residues thereof. Conventionally used one-character or three-character abbreviation for the naturally occurring amino acid is used herein (See documents [Lehninger, Biochemistry, 2d ed., pp. 71-92, Worth Publishers: New York, 1975]). Amino acid includes not only D-amino acid but also chemically-modified amino acids, for example, amino acid analogs, naturally occurring amino acids that is typically incorporated to proteins, for example, norleucine, and chemically-synthesized compounds with amino acid-like characteristics such as properties known to a relevant art. For example, phenylalanine or proline analogs or mimetics that allows conformational limitations of peptide compounds identically to natural phenylalanine (Phe) or proline (Pro) is included in the definition of amino acid. Such analogs and mimetics are referred as "functional equivalences" of amino acids as used herein. Other examples of amino acids are illustrated in documents (See [Roberts and Vellaccio, The peptides: Analysis, Synthesis, Biology, Eds. Gross and Meiehofer, Vol. 5, p. 341, Academic Press, Inc.: N.Y. 1983]).

For example, synthetic peptides synthesized by standard solid-phase synthesis technique are not limited to amino acids encoded by genes, and therefore, allows a more widely various substitutions for the given amino acids. Amino acids that are not encoded by the genetic code are referred as "amino acid analog" as used herein, and for example, are described in WO 90/01940. For example, amino acid analogs include 2-amino adipic acid (Aad) to Glu and Asp; 2-amino pimelic acid (Apm) to Glu and Asp; 2-amino butyric acid (Abu) to Met, Leu and other aliphatic amino acids; 2-amino heptanoic acid (Ahe) to Met, Leu and other aliphatic amino acids; 2-amino iso-butyric acid (Aib) to Gly; cyclohexyl alanine (Cha) to Val, Leu and Ile; homo arginine (Har) to Arg and Lys; 2,3-diamino propionic acid (Dap) to Arg and His; N-ethyl glycine (EtGly) to Gly, Pro and Ala; N-ethyl asparagine (EtAsn) to Asn and Gln; hydroxyl lysine (Hyl) to Lys; allo hydroxyl lysine (AHyl) to Lys; 3-(and 4-) hydroxyl proline (3Hyp, 4Hyp) to Pro, Ser and Thr; allo-isoleucine (AIle) to Ile, Leu and Val; 4-amidino phenyl alanine to Arg; N-methyl glycine (MeGly, sarcosine) to Gly, Pro and Ala; N-methyl isoleucine (MeIle) to Ile; norvaline (Nva) to Met and other aliphatic amino acids; ornithine (Orn) to Lys, Arg and His; citrulline (Cit) and methionine sulfoxide (MSO) to Thr, Asn and Gln; and N-methyl phenyl alanine (MePhe), trimethyl phenyl alanine, halo-(F—, Cl—, Br— or I—) phenyl alanine or trifluoryl phenyl alanine to Phe.

As used herein, the term 'peptide' includes any of proteins, fragments of the proteins and peptides that are isolated from naturally-occurring environment or synthesized by recombinant technique or chemical synthesis. For example, the peptides of the present invention may comprise at least 5, preferably 10 amino acids.

In a particular embodiment, compounds variants, for example peptide variants with one or more amino acid substitutions are provided. As used herein, the term "peptide variants" is intended to mean that peptides of which amino acid sequence has one or more amino acid substitutions, deletions, additions and/or insertions, and which exhibits virtually the identical biological functions as the original peptide. The peptide variants should have the identity of 70% or more, preferably 90% of more, more preferably 95% or more as the original peptide. As such substituents, amino acid substituents as known "conservative" may be included. Also, variants may include nonconservative changes. In one exemplary embodiment, the sequence of the variant polypeptides become different from original sequence by substitutions, deletions, additions or insertions of 5 or less amino acids. Besides, variants may be changed by deletions or additions of amino acids that have minimal effects upon immunogenicity, a secondary structure, and hydropathic nature of a peptide.

As used herein, the term "conservative" substitution means that there are little changes in the secondary structure and hydropathic nature of polypeptides in case amino acids of the polypeptides changed to other amino acids, unless mentioned otherwise. Such amino acid variations with regard to the conservative substitutions may be obtained based upon relative similarity of side chain substituents of amino acids, for example, polarity, charge, solubility, hydrophobicity, hydrophilicity, and/or amphipathic nature.

For example, amino acids may be classified as 1) hydrophobic (methionine, alanine, valine, leucine, isoleucine), 2) neutral hydrophilic (cysteine, serine, threonine, asparagine, glutamine), 3) acidic (aspartic acid, glutamic acid), 4) basic (histidine, lysine, arginine), 5) residues having influence on the chain directions (glycine, proline), and 6) aromatic (tryptophane, tyrosine, phenylalanine) based upon the common side chains properties. Conservative variation will accompany an exchange of one member in each of the classes for another member in the same class.

It is possible to know that any of arginine, lysine and histidine is positively charged residue; alanine, glycine and serine has similar sizes; phenylalanine, tryptophane and tyrosine has similar shapes by analysis for the sizes, shapes and kinds of the side chain substitutions of amino acids. Accordingly, based upon those considerations, arginine, lysine and histidine; alanine, glycine and serine; and phenylalanine, tryptophane and tyrosine can be biologically functional equivalents.

Hydropathic index may be considered in introducing variations. Each amino acid is given hydropathic index based upon its own hydrophobicity and charge: Isoleucine (+4.5); Valine (+4.2); Leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

Hydropathic index of amino acids is very important in according interactive biological function of peptides. It has been known that similar biological activities may be maintained in only substituting amino acids having similar hydropathic indices. In case of introducing variations considering the hydropathic index, reciprocal substitutions among amino acids having hydropathic index value differences within preferably ±2, more preferably ±1, further more preferably ±0.5 are done.

Also, it is well known that reciprocal substitutions among amino acids having similar hydrophilicity induce proteins having equivalently biological activities. As disclosed in U.S. Pat. No. 4,554,101, following hydrophilicity value are accorded to each amino acid residue: Arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophane (−3.4). In case of introducing variations considering the hydrophilicity value, reciprocal substitutions among amino acids having hydrophilicity value differences within preferably ±2, more preferably ±1, further more preferably ±0.5 are done.

Amino acid exchanges in proteins that do not generally modify the molecular activities are known in the art (See, H. Neurath, R. L. Hill, The proteins, Academic Press, New York, 1979). The most commonly occurred exchanges are inter-exchange of amino acid residues between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

The term "polynucleotide" or "nucleic acid" are used inter-changeably herein, refers to polymers of nucleotides of any length, and includes comprehensibly DNA (i.e. cDNA) and RAN molecules. "Nucleotide", which is a subunit of nucleic acid molecules, may be deoxyribonucleotide, ribonucleotide, modified deoxyribonucleotide or ribonucleotide, and/or analogs thereof, or any substrates that can be incorporated into polymers by DNA or RNA polymerase or synthetic reactions. Polynucleotide may comprise modified nucleotides, analogues modified polysaccharides or nucleotides, for example methylated nucleotides and analogues thereof (See, Scheit, Nucleotide Analogs, John Wiley, New York (1980); Uhlman and Peyman, Chemical Reviews, 90:543-584 (1990)).

Some variations in nucleotides do not result in variations in proteins. Such nucleic acids include nucleic acid molecules having codons encoding functionally equivalent or identical amino acids or encoding biologically equivalent amino acids. On the other hand, other variations in nucleotides may induce changes in proteins. In spite of variations causing changes of amino acids of proteins, it is possible to obtain variant proteins that show substantially the same activities as the proteins of the present invention.

A person having ordinary skill in the art will appreciate easily that peptides and nucleic acids according to the present invention are not limited to the amino acid sequences or nucleotide (base) sequences described in Sequence Listing, within the scope that they have characteristics of IK factor or fragments thereof and/or nucleic acids encoding IK factor or fragment thereof of the present invention, for example, they have an effect of treating arthritis. For example, biologically functional equivalents, which can be included in the scope of the present invention, may be peptides having amino acid sequence variations that exhibit equivalent biological activities as the peptides of the present invention.

Generally, the peptides (including fusion proteins) and polynucleotides described herein are isolated. "Isolated" peptides or polynucleotides are separated from the original environment. For example, naturally occurring proteins are isolated by removing whole or part of co-existent material in a natural state. Such polypeptides should have purity of 90% or more, preferably 95% or more, more preferably 99% or more. Polynucleotides are isolated by cloning in the vectors.

As used herein, the term "vector" means a construct that can be transfected or delivered into host cells, and preferably prepared in order to enable one or more target genes or sequences to be expressed. For example, the vector includes viral vectors, DNA or RNA expression vectors, plasmid, cosmid, or phage vectors, DNA or RAN expression vectors linked to CCA (cationic condensing agents), DNA or RNA expression vectors packaged with liposomes, specific eukaryotic cells such as producer cells and the likes.

As used herein, the term "expression control sequence" means a nucleic acid sequence which regulates a transcription of nucleic acid molecules. The expression control sequence includes promoters such as a constitutive promoter or an inducible promoter, enhancers and the likes. The expression control sequence is linked to nucleic acid sequence to be transcribed.

As used herein, the term "operatively linked" means a functional linkage between nucleic acid control sequences (for example, promoters, signal sequences, or array at transcription regulatory factor linkage sites) and other nucleic acid sequences, and thereby, the control sequences regulates transcriptions and/or translations of the other nucleic acid sequences.

As used herein, the term "pharmaceutically effective amount" or "therapeutically effective amount" means an amount of sufficiently accomplishing efficacy or activation of an active ingredient, a peptide or fragments thereof and/or nucleic acids encoding the peptide or fragments thereof. For example, the pharmaceutical composition containing peptides or gene delivery vehicles including nucleic acids encoding the peptides may be applied to treat and/or prevent gouty arthritis, polyarthritis, arthritis deformans as well as rheumatoid arthritis.

Peptides, Nucleic Acids and Vectors

IK factor is a cytokine that suppresses the expression of Major histocompatibility complex II (MHC class II) on the surface of antigen presenting cell (APC) that presents antigens with CD4 T cells. It was reported that IK factor activates cAMP and suppresses expressions of IFN-γ (interferon-gamma) that is induced by viral infections and of MHC class II which is induced by IFN-γ.

As exemplarily shown in FIG. 1, a full-length nucleic acid molecule encoding IK factor has Nuclear Localization Signal Sequence (NLS) and trimeric coiled-coil motif at N'-terminal (5'-end) region. Besides, the full-length nucleic acid molecule encoding IK factor RED domain, which has repeated sequences of Arg (R)-Asp (D) and Arg (R)-Glu (E) found mainly in nuclear proteins, and three NLSs at C-terminal (3'-end) region. Exemplarily, the full-length nucleic acid molecule encoding IK factor is a polynucleotide consisting of 1,674 nucleotides of SEQ ID NO: 1. IK factor is expressed except the last transcription termination codons of SEQ ID NO: 1 and may be consisted of 557 amino acids of SEQ ID NO: 2. But, a person having ordinary skill in the art will appreciate that IK factor and IK nucleic acids encoding IK factor according the present invention are not limited to the sequences described in Sequence Listing.

A joint is a composite tissue that synovial membranes, cartilages, bones and synovial fluids are linked each other systematically and have reciprocal influences on each other through cytokines. It was reported that phenomena such as chronic inflammation, tissue necrosis, cellular infiltration, neovascularization, joint destructions and the likes within joints are major etiology of rheumatoid arthritis. Synovial membrane tissues, which are referred as pannus and known as essentially pathological findings in rheumatoid arthritis, infiltrates around the joints and thereby, inducing bone resorption. It was reported that antigen presenting cells and T cells with a high density are found in pannus and interactions among such cells cause initiation and expansion of immune responses induced by T cells. Actually, much antigen presenting cells expressing MHC class II are found in pannus of patients with rheumatoid arthritis and HLA-DR positive cells and T cells are located at the same site. Accordingly, inhibiting interactions between antigen presenting cells expressing MHC class II and T cells may be effective for treating efficiently rheumatoid arthritis.

Particularly, there are IL-17+T cells and functionally activated IL-17 in the pathogenic lesion, synovial membrane in case of developing rheumatoid arthritis. IL-17 is highly detected in serum of patients with rheumatoid arthritis, and IL-17A induces expressions of IL-1β and IL-6 within synovial membranes of patients with rheumatoid arthritis. With regard to arthritis, IL-17 suppresses substrate production within chondrocytes and osteoblasts and causes joint damages, and thereby, making a lack of tissue regenerations. Also, IL-17A activates expression and functions of matrix metalloproteinase (MMPs) and causes irrevocable cartilage erosions within the mouse model together with tumor necrosis factor (TNF). Local interaction between Th17 cells and synovial membrane cells in inflammatory responses facilitates secretion of MMP and expressions of IL-1β and IL-6 in the synovial membranes. With regard to osteoclasia, IL-17 causes receptor activator of NF-κB ligand (RANKL) on the osteoblasts to express so that it makes an amplification of RANK signaling in the osteoclasts. Particularly, it was known that Th17 cells that makes an expression of RANKL plays an important role in differentiation process of osteoclasts.

According to the present invention, nucleic acid molecules encoding IK factor or fragments of IK factor can suppress and prevent arthritis progression. Especially, such nucleic acids suppress secretion of rheumatoid-arthritis related cytokines and block differentiation of rheumatoid-arthritis related immune cells.

Besides, in an exemplary embodiment of the present invention, nucleic acid fragments (tIK nucleic acid fragment) encoding fragments of IK factor, for example, encoding truncated fragments having only C-terminal fragments without excised N-terminal fragments (referred as "tIK" factor or "tIK" herein) may be expressed within appropriate expression systems. Those nucleic acids are expressed to peptides which suppress expression of MHC class II associated with an inflammatory immune response which is one of major indications of arthritis. More concretely, tIK nucleic acid fragments, which are truncated nucleic acid fragments compared to the full-length IK nucleic acid, and/or mutant tIK nucleic acid fragments, which are variants that some nucleotides are substituted for original nucleotides of tIK nucleic acids, increases expressions of CDCA3 (Cell division cycle-associated protein 3), CNOT1 (CCR4-NOT transcription complex subunit 1) and MAPK1 (Mitogen-activated protein kinase 1) each of which is an upstream regulatory factor suppressing the expression of CIITA (class II, major histocompatibility complex, transactivator) which is involved in the expression of MHC class II (See FIG. 3). Also, since the mutant tIK having some substituted nucleic acids may inactivate such effects, we certified that some sites in IK factor are physical activation site involved in the expressions of the upstream regulatory factors for MHC class II.

According to an exemplary embodiment of the present invention, the transgenic mice, which are induced to express fragments of IK factor such as fragments without excised N-terminal ("tIK-IL1RaKO" mice) show less arthritis inducement level compared to spontaneously-induced arthritis mouse model ("IL1RaKO" mice) (See, FIGS. 4A, 4B and 5). Besides, the inflammation inducement or cartilage erosion level in joint tissues extracted from tIK-IL1RaKO mice is less than that in joint tissues extracted from IL1RaKO mice (See FIGS. 6A, 6B). Furthermore, tIK-IL1RaKO mice show less bone damages than IL1RaKO mice (See FIG. 7).

Particularly, tIK-IL1RaKO mice exhibit reduced secretion of cytokines that is involved in arthritis progression in joint tissue and serum compared to IL1RaKO mice. More concretely, there are reduced expression of cytokines which induce inflammation in the joints (See FIGS. 8A and 8B) as well as in the serum (See FIG. 9) extracted from the tIK-IL1RaKO mice, which are transgenic mice so as to induce truncated IK factor (tIK factor), compared to spontaneously-induced arthritis mice (IL-1 antagonist-receptor knock-out mouse, IL1RaKO mice).

In an exemplary example of the present invention, the nucleic acid molecules encoding fragments of IK factor are expressed through an appropriate expression system, and suppresses expressions of interleukin-1 beta (IL-1β), interleukin-6 (IL-6), interleukin-17 and monocyte chemotactic protein-1 (MCP-1), also known as CCL2 (Chemokine (C—C motif) ligand 2), each of which are involved in inflammatory immune response. Such results means that injecting nucleic acid molecules encoding IK factor or fragments of IK factor using appropriate vectors or gene delivery vehicles into a human body can suppress the progressions of arthritis and may influences upon systemic immune responses especially. In addition, tIK-IL1RaKO mice, which are induced to express IK factor, show suppressive T cell differentiation (See FIGS. 10A and 10B), and influences on activation factors of macrophage (See FIG. 11), compared to spontaneously-induced arthritis mouse model (IL1RaKO mice).

Furthermore, in an exemplary embodiment of the present invention, relatively small sized fragments of IK factor containing active sites, for example peptides consisting of about 10 amino acids having an amino acid at the active sites and adjacent amino acids can suppress the progression of arthritis. Such peptides suppress the expressions of inflammatory cytokines in macrophages such as tumor necrosis factor alpha (TNF-α), IL-6 and IL-17 (See FIGS. 12A, 12B and 15B) and also suppress pathogenic cells involved in arthritis such as Th1 cell and Th17 cell (See FIGS. 13A to 13C). Further, such peptides suppress the progression of arthritis in spontaneously-induced arthritis mouse model IL1RaKR mice (See FIGS. 14A and 14B), and suppress the differentiation of Th17 cell in the spontaneously-induced arthritis mice (See FIG. 15A).

In an exemplary embodiment, the nucleic acid molecules encoding IK factor or fragments of IK factor may be transfected into a living body using appropriated expression systems or gene delivery vehicles so as to suppress the progression of arthritis or treat induced arthritis (See FIGS. 19A and 19B).

As described above, IL-17 which is secreted depending upon the differentiation of Th17 cell plays an important role with regard to rheumatoid arthritis. Sine IK factor or fragment of IK factor and/or nucleic acids encoding IK factor or fragments of IK factor suppress the differentiation of Th17 cell, which receives attentions as a basic cause of rheumatoid arthritis, it is possible to treat rheumatoid arthritis more effectively compared to the conventionally used arthritis drugs using peptides and/or nucleic acid molecules of the present invention.

In addition, because most of the biologics as represented by monoclonal antibodies may induce immune responses in case they are injected into human bodies and prepared through complex manufacturing processes, they are sold at a high price. In contrast, IK factor of which efficiencies are certified in the present invention is an intrinsic cytokine in a human body so that there is little chance of immune response induced by IK factor, and therefore, IK factor is very safe. Also, it is possible to prepare IK factor at a relatively lower price.

Accordingly, the present invention relates to IK factor or fragments of IK factor for treating arthritis. As an active ingredient for treating arthritis, fragments of IK factor having truncated some amino acids of full-length IK factor are preferable, and fragments of IK factor without excised N-terminal amino acids of full-length IK factor are more preferable.

Exemplarily, the full-length IK factor may be a peptide having an amino acid sequence of SEQ ID NO: 2. As an example of the fragments of IK factor, a peptide such as a truncated IK factor (tIK factor) which has a amino acid sequence of SEQ ID NO: 4 which does not have excised 315 amino acids consisting of N-terminus from the full-length IK factor and has only 242 amino acids consisting of C-terminus of the full-length IK factor of SEQ ID NO: 2 or partial peptides of SEQ ID NO: 4. As an example of the fragments of IK factor, the peptide fragments without excised amino acids at N-terminal region among the amino acids consisting of the full-length IK factor is preferable because the fragments is relatively small so that they are easy to prepare. Also, the peptide fragments without excised amino acids at N-terminal may be more advantageous to exhibit biological functions in in vivo and/or ex vivo compared to the full-length IK factor.

According to exemplary examples of the present invention, the $382^{nd}$ amino acid Serine of SEQ ID NO: 2 ($67^{th}$ amino acid of SEQ ID NO: 4) Serine (S382), the $489^{th}$ amino acid of SEQ ID NO: 2 ($174^{th}$ amino acid of SEQ ID NO: 4) Tyrosine (Y489) and/or the $492^{nd}$ amino acid of SEQ ID NO: 2 ($177^{th}$ amino acid of SEQ ID NO: 4) Tyrosine (Y492) are concerned with the biological functions of IK factor and/or fragments of IK factor. Particularly, it is expected that the $382^{nd}$ amino acid Serine of SEQ ID NO: 2 (S382) and/or the $489^{th}$ amino acid Tyrosine of SEQ ID NO: 2 (Y489) are active sites of IK factor and/or the fragments of IK factor.

Accordingly, in addition to the fragment of IK factor having an amino acid sequence of SEQ ID NO: 4, it is possible to use other fragments of IK factor comprising the amino acids at the active sites with relatively short length as fragments of IK factor. Exemplarily, the fragments of IK factor according to the present invention may comprise peptides that include 10 or more, for example 100 or more, or 200 or more, amino acids which has at least one amino acid residue selected from the group consisting of the $382^{nd}$ amino acid Serine (S382), the $489^{th}$ amino acid Tyrosine (Y489) and the $492^{nd}$ amino acid Tyrosine (Y492) of SEQ ID NO: 2, and amino acids adjacent to the selected amino acid residue. In an exemplary embodiments, the fragments of IK factor comprises peptides that includes 10 to 100, preferably 10 to 50, more preferably 10 to 30 amino acids which has at least one amino acid residue selected from the $382^{nd}$ amino acid Serine (S382), the $489^{th}$ amino acid Tyrosine (Y489) and the $492^{nd}$ amino acid Tyrosine (Y492) of SEQ ID NO: 2, and amino acids adjacent to the selected amino acid residue. At least one amino acid of such selected amino acid residues may be a modified amino acid such as a phosphorylated amino acid.

Exemplarily, the fragments of IK factor according to the present invention are a peptide having an amino acid sequence of SEQ ID NO: 2 or partial peptides of SEQ ID NO: 2. In an exemplary embodiment, the fragments of IK factor are peptides that include 10 or more, for example 10 to 100, preferably 10 to 50, more preferably 10 to 30 amino acids which has at least one amino acid residue selected from the $382^{nd}$ amino acid Serine (S382) and the $489^{th}$ amino acid Tyrosine (Y489) of SEQ ID NO: 2, and amino acids adjacent to the selected amino acid residue.

Exemplarity, the active amino acids such as the $382^{nd}$ amino acid Serine (S382), the $489^{th}$ amino acid Tyrosine (Y489) and the $492^{nd}$ amino acid Tyrosine (Y492) are not located at N-terminal or C-terminal of the peptides that may be used as the fragments of IK factor. Peptides having 2 or more adjacent amino acids bonded respectively to each of the N-terminal and C-terminal of the selected active amino acid residue may be used in order to align the active amino acid, the selected amino acid residue in the center of the peptides. Exemplarily, 2 to 8 or more, preferably 3 to 7 or more adjacent amino acids may be bonded respectively to each of the N-terminal and C-terminal of the active amino acid. For example, 2 to 100 such as 3 to 70, preferably 3 to 30, more preferably 3 to 20 adjacent amino acids may be bonded respectively to each terminal of the active amino acid.

In one exemplary embodiment, the fragments of IK factor also comprise a peptide of SEQ ID NO: 47 that consists of amino acids from the $377^{th}$ amino acid Glutamic acid to the $391^{st}$ amino acid Aspartic acid of SEQ ID NO: 2, and/or a peptide of SEQ ID NO: 49 that consists of amino acids from the $484^{th}$ amino acid Aspartic acid to the $496^{th}$ amino acid Lysine of SEQ ID NO: 2.

According to an exemplary example, the full-length IK factor consists of 557 amino acids of SEQ ID NO: 2 and the fragment of IK factor of SEQ ID NO: 4, which does not include the excised N-terminal region compared to the full-length IK factor, consists of 242 amino acids. Considering those points, the fragments of IK factor according to the present invention may be consisted of maximally 300-500 amino acids of SEQ ID NO: 2. But, the fragments of IK which can be used in the present invention is not limited to such fragments.

Also, for example, except the active amino acids such as 5382, Y489 and Y492 in the IK factor and/or fragments of the IK factor, the rest other amino acids may be substituted for other amino acids by a conservative substitution, and some amino acids may be deleted, added and/or inserted if necessary.

IK factor or the peptides as fragments of IK factor may be isolated by manufacturing through recombinant means or chemical synthesis. Exemplarily, the peptides which are expressed by nucleic acid sequences referred herein may be manufactured easily by known processes using any of known may expression vectors. The expression can be accomplished in appropriated host cells that are transformed by expression vectors comprising DNA sequences encoding the peptides. The appropriated host cells include prokarytoes, yeast cells and eukaryotes. It is preferable to use *E. coli*, yeast or mammalian cell lines (such as Cos or CHO cell) as a host cell. A supernatant containing a recombinant protein which is obtained by water soluble host/vector system and secreted into culture solution is concentrated using a commercially available filter for the purification of proteins. In the next step, the concentrated solution obtained by the above-mentioned procedure is purified using appropriate purification matrix such as affinity matrix or ion exchange matrix. Lastly, pure protein can be obtained by performing a single step or multiple steps of reverse phase HPLC assay.

The fragments or variants with 100 or less, generally 50 or more amino acids can be manufactured by chemical synthesis. For example, such polypeptides can be synthesized commercially available solid-phase techniques, i.e., Merrifield solid-phase synthesis method which adds subsequently amino acids to a growing amino acid chain (See, Merrifield, 1963, J. Am. Chem. Soc. 85:2146-2149). The apparatus for automatic synthesizing polypeptides may be available from supplying companies and can be operated pursuant to the supplier's manual.

For example, the peptides according to the present invention expressed in bacteria may be secreted to a periplasm of the host and be recovered therefrom. Typically, recovering proteins comprises homogenizing the bacteria by means of osmotic shock, ultra-sonication or dissolution. If the cells are destroyed, it is possible to remove them by centrifugating or filtering cell debris or the whole cells. The proteins may be further isolated by, for example, an affinity resin chromatography assay. Alternatively, proteins may be transferred to a culture medium from where they may be isolated. The produced proteins by separating cells from the culture media, filtering and concentrating the culture supernatant may be further isolated. The expressed polypeptides may be further isolated and characterized by conventionally known processes, for example, fractional distillation on a immuno-affinity or ion-exchange column; ethanol precipitation, reverse-phase chromatography; silica or cation exchange resins for example chromatography on DEAE; chromatofocusing; SDS-PAGE; ammonium phosphate precipitation; gel filtration chromatography, for example using sephadex G75; ligand affinity or western-blotting assay using hydrophobic affinity resins or appropriate antigens immobilized on a matrix.

Besides, the produced peptides may be purified in order to obtain a substantially homogenizing agent for further assay and uses. Standard protein purification methods which have been known to the art may be used. Following procedures are examples of an appropriate purification: fractional distillation on immunoaffinity or cation-exchange resins, for example, chromatography on DEAE, chromatofocusing, SDA-PAGE, ammonium phosphate precipitation, and gel filtration chromatography, for example using sephadex G75.

Also, the present invention relates to a nucleic acid molecule or a polynucleotide encoding IK factor or fragments of IK for treating arthritis. Similarly to the peptides, IK nucleic acid fragments, which some nucleotides encoding the full-length IK factor are excised, are preferable, and IK nucleic acid fragments, which nucleotides encoding 5'-end the full-length IK factor are excised, are more preferable as the IK nucleic acid fragments.

Exemplarily, the nucleic acid molecule encoding the full-length IK factor may be a nucleic acid having a nucleotide sequence of SEQ ID NO: 1. Exemplarily, the nucleic acid molecule encoding the fragment of IK factor may be a nucleic acid encoding the truncated IK factor (tIK nucleic acid fragment) having a nucleotide sequence of SEQ ID NO: 3, which 945 nucleotides at 5'-end of SEQ ID NO: 1 are out of excised, or nucleic acids consisting a part of the nucleotides of SEQ ID NO: 3.

Each of the $382^{nd}$ amino acid Serine (S382), the $489^{th}$ amino acid Tyrosine (Y489) and the $492^{nd}$ amino acid Tyrosine (Y492) of SEQ ID NO: 2 may be expressed respectively the $1444$-$1146^{th}$ nucleotide residues set of SEQ ID NO: 1 (the $199$-$201^{st}$ nucleotide residues set of SEQ ID NO: 3), the $1465$-$1467^{th}$ nucleotide residues set of SEQ ID NO: 1 (the $520$-$522^{nd}$ nucleotide residues set of SEQ ID NO: 3) and the $1474$-$1476^{th}$ nucleotide residues set of SEQ ID NO: 1 (the $529$-$531^{st}$ nucleotide residues set of SEQ ID NO: 3).

Accordingly, in addition to the IK nucleic acid fragment having a nucleotide sequence of SEQ ID NO: 3, other IK nucleic acid fragments comprising nucleotides with relatively short length as the IK nucleic acid fragments. Exemplarily, the IK nucleic acid fragments according to the present invention may comprise 30 or more, for example 300 or more, or 600 or more nucleic acids that has at least one nucleotide residues set selected from the group consisting of the 1144-1146$^{th}$ nucleotide residues set of SEQ ID NO: 1 (199-201$^{st}$ nucleotide residues set of SEQ ID NO: 3), the 1465-1467$^{th}$ nucleotide residues set of SEQ ID NO: 1 (the 520-522$^{nd}$ nucleotide residues set of SEQ ID NO: 3) and the 1474-1476$^{th}$ nucleotide residues set of SEQ ID NO: 1 (the 529-531$^{st}$ nucleotide residues set of SEQ ID NO: 3), and nucleotides adjacent to the selected nucleotide residues set. In an exemplary embodiment, the nucleic acids encoding fragment of IK factor comprise 30 to 300, preferably 30 to 150, more preferably 30 to 90 nucleotides which has at least one nucleotide residues set selected from the group consisting of the 1144-1146$^{th}$ nucleotide residues set of SEQ ID NO: 1, the 1464-1467$^{th}$ nucleotide residues set of SEQ ID NO: 1 and the 1474-1476$^{th}$ nucleotide residues set of SEQ ID NO: 1, and nucleotides adjacent to the selected nucleotide residues set.

Exemplarily, the IK nucleic acid fragments is a nucleic acid molecule having a nucleotide sequence of SEQ ID NO: 1 or partial fragments of the nucleic acid molecule. In an exemplary embodiment, the nucleic acid molecule encoding the partial fragments of IK factor is nucleic acids which has 30 to 300, preferably 30 to 300, more preferably 30 to 90 nucleotides that comprises at least one nucleotide residues set selected from the group consisting of the 1144-1146$^{th}$ nucleotide residues set of SEQ ID NO: 1 and the 1465-1467$^{th}$ nucleotide residues set of SEQ ID NO: 1, and nucleotides adjacent to the selected nucleotide residues set.

6 or more nucleotides may be bonded respectively to each of 5'-end and 3'-end of the selected nucleotide residues set in order to align the selected nucleotide residues set in the center of the nucleic acids. Exemplarily, 6 to 24 or more, preferably 9 to 21 or more adjacent nucleotides may be bonded respectively each of 5'-end and 3'-end of the selected nucleotide residues set. For example, 6 to 300 such as 9 to 210, preferably 9 to 90, more preferably 9 to 60 adjacent nucleotides may be bonded respectively to each of 5'-end and 3'-end of the selected nucleotide residues set.

In one exemplary embodiment, the nucleic acid molecules encoding the fragments of IK factor may a nucleic acid having a nucleotide sequence of SEQ ID NO: 46 and/or a nucleic acid having a nucleotide sequence of SEQ ID NO: 48. Exemplarily, the nucleic acid molecule encoding the fragments of IK factor may comprise, but are not limited to, maximally about 900-1,500 nucleotides in the nucleotides of SEQ ID NO: 1. Each of the 1144-1146$^{th}$ nucleotide residues set of SEQ ID NO: 1 encoding the 382$^{nd}$ amino acid Serine (S382) of SEQ ID NO: 2, the 1465-1467$^{th}$ nucleotide residues and/or the 1474-1476$^{th}$ nucleotide residues set of SEQ ID NO: 1 each of which encoding the 489$^{th}$ amino acid Tyrosine (Y489) and the 492$^{nd}$ amino acid Tyrosine (Y492) of SEQ ID NO: 2 may have other nucleotide sequences encoding serine or tyrosine.

The nucleic acid molecules encoding IK factor or the fragments of IK factor may be included into appropriate vectors. The vectors include expression control sequences linked to the polynucleotide of the present invention. In an exemplary embodiment of the present invention, the vectors may comprise one or more polynucleotides encoding interesting target molecules. The polynucleotide of the present invention may combine other polynucleotides so as to encode fusion proteins.

Exemplarily, the polynucleotides of the present invention are constructed in order to transfect into mammalian cells and expressed within the cells. Such a construction is particularly useful for the purposes of treatment. There are many processes to express the polynucleotides in the host cells and it is possible to adopt any appropriate processes. For example, one polynucleotide may be inserted into viral vectors such as adenovirus, adeno-associated virus, retrovirus, vaccinia virus, Lentivirus, baculovirus or other pox viruses (e.g. avian pox virus), and the likes. It has already been well-known that techniques of inserting DNA into such vectors. It is possible to insert additionally targeting moieties such as genes with regard to selectable markers for making easy certification or selection for the transduced cells and/or genes encoding ligands acting as a receptor to a particular target cell in the retrovirus vector. Targeting may be performed by known processes using specific antigens.

It is possible to use plural vectors that are commercially available and known to in the art for the purposes of the present invention. Selecting appropriate vectors will be mainly dependent upon the sizes of the nucleic acids to be inserted into the vectors and specific host cells transformed with the vectors. Each vector contains various components, depending upon its functions (amplification and/or expression of foreign polynucleotides) and compatibilities to the specific host cells having thereof. Vector components generally comprises, but are not limited to, replication origins (especially if the vector is inserted into prokaryotes), selection marker genes, promoters, ribosome binding sites (RBS), signal sequences, foreign nucleic acids insert, and a transcription termination sequence.

For example, the vector of the present invention may comprise expression control sequences, which may have an effect on the expression of the proteins, such as a initiation codon, a termination codon, a poly-adenylation signal, enhancers, signal sequences for membrane-targeting or section, and the likes. The poly-adenylation sequence increases the safety of the transcripts and facilitates cytoplasm transports. Enhancer sequences are nucleic acid sequences which are located at various sites with regard to the promoters and increase transcription activity compared to a transcription activity by the promoters without the enhancer sequences. Signal sequences comprise, but are not limited to, PhoA signal sequence, OmpA signal sequence, and the likes in case the host cell is bacteria in *Escherichia* spp., α-amylase signal sequence, subtilisin sequence and the likes in case the host cell is bacteria in *Bacillus* spp., MF-α signal sequence, SUC2 signal sequence and the likes in case the hose cell is yeast, and insulin signal sequence, α-interferon signal sequence, antibody molecule signal sequence and the likes in case the host cell is mammals.

A category of vector is a 'plasmid' which refers to a circular, double-stranded DNA loop into which additional DNA fragments may be ligated. Another category of vector is a phage vector. Further another category of vector is viral vectors which additional DNA fragments may be ligated into the viral genome. Specific vectors can replicate autonomously into the host cells having the transfected the vectors (for example, viral vectors and episome mammalian vectors having bacterial replication origins). Other vectors (for example, non-episome mammalian vectors) may be integrated into the genome of a host cell as they transfect to the host cell, and thereby, being replicated together with the genome of the host cell. Besides, specific vectors may direct the expression of genes operatively linked to the vectors. Such vectors are referred herein as a "recombinant expression vector (or, shortly, "recombinant vector"). Generally, the expression vectors, which may be useful for recombinant DNA technologies, exist as a shape of plasmid.

It is possible to construct vector systems of the present invention through various processes known to in the art, and such processes are discloses in Sambrook et al, Molecular Cloning, A Laboratory manual, Cold Spring Harbor Laboratory Press (2001), which is incorporated herein by reference. For example, the vectors, which may be used in the present invention, may be manufactured by manipulating the usually used vectors in the art, plasmid (e.g., pSC101, ColE1, pBR322, pUC8/9, phC79, pUC19, pET and the likes), phage (e.g., λgt4λB, λ-Charon, λΔzl, κGEM™-11, M13 and the likes), virus (e.g., SV40 and the likes).

In a concrete embodiment of the present invention, nucleic acid molecules are inserted into host cells using virus expression systems (e.g., vaccinia or other pox viruses, retroviruses, lentivirus, baculovirus, adenovirus, or adeno-associated virus). Exemplarily, virus vector comprises, but are not limited to, retrovirus vectors derived from HIV, SIV, murine retroviruses, gibbon ape leukemia virus, AAV (adeno-associated viruses), adenoviruses and the likes (Miller et al., 1990, Mol. Cell Biol. 10: 4239; J. Kolberg 1992, NIH Res. 4: 43; Cornetta et al., 1991, Hum. Gene Ther. 2: 215). Retrovirus vectors derived from murine leukemia virus (MuLV), gibbon ape leukemia virus (GaLV), ecotropic retroviruses, SIV (simian immunodeficiency virus), HIV (human immunodeficiency virus) and the likes have been widely used (Buchscher et al., 1992, J. Virol. 66(5): 2731-2739; Johann et al., 1992, J. Virol. 66(5): 1635-1640; Sommerfelt et al., 1990, Virol. 176: 58-59; Wilson et al., 1989, J. Virol. 53: 2374-2378; Miller et al., 1991, J. Virol. 65: 2220-2224; Rosenberg and Fauci 1993 in Fundamental Immunology, Third Edition, W. E. Paul (ed.) Raven Press, Ltd., New York and the references therein; Miller et al., 1990, Mol. Cell Biol. 10: 4239; R. Kolberg, 1992, J. NIH Res. 4: 43; Cornetta et al., 1991, Hum. Gene Ther. 2: 215).

Constitutively or inducible promoters can be used in the present invention as pacific occasions that can be certified by a person having ordinary skill in the art arise. Plural promoters that recognized by various possible host cells have been widely known in the art. Selected promoters may be linked operatively to the cistron DNA encoding the polypeptides described herein by removing the removing the promoters from suppliers DNA through restriction enzyme digestions and then inserting the isolated promoter sequences into the selection vectors. It is possible to direct amplification and/or expression of the target genes using both natural promoter sequences and a plurality of foreign promoters. But, foreign promoters are generally more preferable to the natural targeting polypeptide promoters because the foreign promoters allows much transcription and high yield of the expressed target genes compared to the natural targeting polypeptide promoters.

Meanwhile, when the vector of the present invention is an expression vector and a host cell is a eukaryote, promoters derived from the genome of the mammalian cells (e.g., metallothionein promoter) or promoters derived from mammalian viruses (e.g. adenovirus late promoter, vaccinia virus 7.5K promoter, SV40 promoter, cytomegalovirus promoter and tK promoter of HSV) may be used, and they generally have poly-adenylation signal as a transcription termination signal.

Besides, when the recombinant vector of the present invention is a replicable repression vector, it may comprise a replication origin, which is a specific nucleic acid sequence for initiating replication. In addition, the recombinant vectors may comprise sequences encoding selectable markers. The selectable markers are intended to screen transformed cells by the vectors and markers giving selectable phenotypes such as drug resistances, nutritional requirements, cytotoxic agent resistances, or expressions of surface proteins may be used. The vectors of the present invention may comprise antibiotics resistant genes which have been conventionally used in the art, for example, ampicillin, gentamicin, carbenicillin, chloramphenicol, streptomycin, kanamycin, geneticin, neomycin, and tetracycline resistant genes as selectable markers. It is possible to screen the transformed cells because only cells expressing the selectable markers can survive in an environment of treating elective agents. Representative example of the selectable markers may comprise an auxotrophic marker, ura4, leu1, his3 and the likes, but the selectable markers can be used in the present invention is not limited to such an example.

Various in vitro amplification techniques that amplify sequences sub-cloned to expression vectors have been known. There are PCR (polymerase chain reaction), LCR (ligase chain reaction), Qβ-replicase amplification and techniques using other RNA polymerases in such techniques (Sambrook et al., 1989, Molecular Cloning-A Laboratory Manual ($2^{nd}$ Ed.) 1-3; U.S. Pat. No. 4,683,202; PCR protocols: A guide to Methods and Applications, Innis et al. eds. Academic Press Inc., San Diego, Calif. 1990. Improved methods of cloning in vitro amplified nucleic acids are described in U.S. Pat. No. 5,426,039).

The vector of the present invention may be fused with other sequences in order to facilitate the purification of the peptide therefrom. Fused sequences comprises glutathione S-transferase (Pharmacia, USA), maltose binding protein (NEB, USA), FLAG (IBI, USA), 6× His (hexahistidine, Quiagen, USA) and the likes, and 6× His is most preferable. Owing to the additional sequences for purification, the proteins expressed in the host cell are purified with promptness and ease through affinity chromatography assay. If necessary, a sequence encoding Fc fragments may be fused with the vector in order to facilitate extracellular secretion of those peptides.

In accordance with an exemplary embodiment of the present invention, the peptides expressed by the vectors which comprises nucleotide sequences encoding IK factor or partial fragments of IK factor are purified by affinity chromatography. For example, it is possible to purify the desired peptides with promptness and ease by using glutathione as a substrate of glutathione-S-transferase when glutathione-S-transferase is fused with the vector, and by using Ni-NTA His-binding resin column (Novagen, USA) when the vector comprises 6× his.

It is possible to any host cells known in the art as long as the host cells make the vectors stably and continuously clone and express. For example, host cells may comprise *E. coli* JM109, *E. coli* BL21 (DE3), *E. coli* RR1, *E. coli* LE392, *E. coli* B, *E. coli* X 1776, *E. coli* W3110, *Bacillus* strains such as *Bacillus subtilis, Bacillus thuringiensis*, and enterobacteriaceae strains such as *Salmonella typhimurium, Serratia marcescens* and various *Pseudomonas* species.

Besides, yeast (*Saccharromyce cerevisiae*), insect cells (e.g., SF9 cell), human cells (e.g., CHO (Chinese hamster ovary) cell, W138, BHK, COS-7, 293, HepG2, 3T3, RIN and MDCK cell lines) may be used as host cells in case of transforming eukaryotes with the vectors of the present invention.

The vectors of the present invention may be used in modifying genetically the host cells in in vivo or ex vivo or in vitro. With regard to methods of modifying genetically cells, various methods comprising cell transfection or transduction with viral vectors, calcium phosphate precipitation, methods of fusing recipient cells with bacterial protoplast containing DNA, method of treating recipient cells with liposome or microspheres containing DNA, DEAE dextran, receptor mediated endocytosis, electroporation, micro-injection, and gene bombardment are well known in the art.

Pharmaceutical Composition and Administration

In accordance with another embodiment of the present invention, the present invention relates to a pharmaceutical composition for treating arthritis, comprises a therapeutically effective amount of the above-described IK factor and fragments of IK factor; and, if necessary, a pharmaceutically acceptable carrier. In this case, IK factor and peptides, fragments of IK factor may be administered directly to a subject.

In accordance with further another embodiment of the present invention, the present invention relates to pharmaceutical composition for treating arthritis, comprises a gene delivery vehicle having a nucleic acid molecule encoding IK factor or fragments thereof; and, if necessary, a pharmaceutically acceptable carrier. Using the gene delivery vehicle is intended for so called a gene therapy.

Accordingly, the present invention relates to a pharmaceutical composition containing as an active ingredient a peptide, IK factor or fragments thereof, and/or a gene delivery vehicle comprising a nucleic acid molecule encoding IK factor or fragments thereof, or a method for treating arthritis comprising administering such an active ingredient to a subject. In this case, the active ingredient may be contained in an amount of 1.0 ng/mL~10 µg/mL in the pharmaceutical composition.

In one embodiment, the present invention provides a pharmaceutical composition or a medicine containing the compounds of the present invention, a therapeutically inactive carrier, a diluent or an excipient as well as a method of using the compounds of the present invention for manufacturing the composition or medicine. In one example, the compounds may be formulated together with a physiologically acceptable carrier, i.e., a non-toxic carrier to a subject in a dose and concentration used in a shape of a galenical administration at an ambient temperature and appropriate pH, by admixing them with a desired purity. While pH of the formulation is depending upon specific uses and concentrations of the compounds, preferably in the range of about 3 to about 8. In one example, the compounds are formulated in acetate buffer solution at pH 5. In another embodiment, the compounds are sterilized. The compounds may be stored as solid or amorphous composition, freeze-dried formulation and solution.

The composition is formulated, medicated and administered in a manner that is consistent with an excellent medical practice. With regard to it, considering factors includes a specific disorder to treat, a specific patient to treat, a clinical condition of each patient, a cause of the disorder, a transferring site of an agonist, an administration route, an administration schedule, and other factors known to medical practitioners.

If necessary, it is possible to prepare sustained release dosage forms. An appropriated example of the sustained release dosage form comprises semi-permeable matrix of solid hydrophobic polymers containing the compounds, and the matrix is a shaped article, for example a film or a microcapsule. For example, the sustained release matrix comprises polyesters, hydrogels (e.g., poly(2-hydroxyethyl-methacrylate) or poly(vinylalcohlo)), polylactides, copolymers of L-glutamic acid and gamma-ethyl-L-glutamate, non-degradable ethylene-vinyl-acetate, degradable copolymers of lactic acid-glycolic acid, and poly-D-(-)-3-hydroxybutyric acid.

In one example, the pharmaceutically effective amount of the compounds, which is administered parenterally per dose, will be about 0.01-100 mg/kg, alternatively about 0.1-20 mg/kg daily based upon patients' weight, typical initial dose of the used compounds will be 0.3 to 15 mg/kg/day. In another embodiment, oral unit dosage forms, for example, table or capsule contains preferably about 5-100 mg of the compounds of the present invention.

The compounds used as an active ingredient of the composition may be administered by any appropriate means, for example, oral, local (including buccal and subglossal), rectal, vaginal, percutaneous, parenteral, subcutaneous, intraperitoneal, intrapulmonary, intradermal, intradural, epidural and intranasal means, and, if necessary, means for local treatment and intralesional administering. Parenteral injection comprises intramuscular, intravenous, intra-arterial, intraperitoneal, or subcutaneous administration.

The active ingredient compounds of the present invention may be administered with any convenient dosage forms, for example, tablet, powder, capsule, solution, dispersion, suspension, syrup, aerosol, suppository, gel, emulsion, patch and the likes. Such a composition may comprise typical components to a pharmaceutical formulation, for example, diluents, carriers, pH adjusters, sweetening agents, bulking agents, and additional activators.

Typical formulations are manufactured by mixing the compounds of the present invention with a carrier or an excipient. Appropriate carriers and excipients are well-known to a person having ordinary skill in the art and described in detail in the documents [Ansel, Howard C., et al., Ansel's Pharmaceutical Dosage Forms and Drug Delivery Systems. Philadelphia: Lippincott, Williams & Wiklins, 2004; Gennaro, Alfonso R., et al., Remington: The Science and Practice of Pharmacy. Philadelphia: Lippincott, Williams & Wilkins, 2000; and Rowe, Raymond C. Handbook of Pharmaceutical Excipients. Chicago: Pharmaceutical Press, 2005].

For example, the pharmaceutically acceptable carrier contained in the pharmaceutical composition of the present invention comprises, but are not limited to, conventionally used carriers in formulation such as lactose, dextrose, sucrose, sorbitol, mannitol, starch, gum Arabia, calcium phosphate, alginate, water, syrup, methyl cellulose, methyl hydroxy benzoate, propyl hydroxy benzoate, talc, magnesium stearate, and mineral oil.

The formulation may comprise one or more buffering agents, stabilizers, surfactants, wetting agents, lubricants, emulsifiers, suspending agents, conservatives, anti-oxidants, opacifying agents, processing aids, coloring agents, sweetening agents, odoriferous substances, diluents, and other known additives which provides medication (i.e. the compounds of the present invention or its pharmaceutical composition) with a nice appearance or gives help to manufacture of the pharmaceutical product (i.e. medication).

The pharmaceutical composition of the present invention may be manufactured in the shape of unit dosage form by formulating the compounds using the pharmaceutically acceptable carrier and/or excipients or incorporating the compounds into multiple dosages vessel according to techniques which can be accomplished easily by a person having ordinary skill in the art. The formulation of the composition may be a solution, a suspension or an emulsion in oil or aqueous media, or an extract, a powder, or a granule, a tablet or a capsule, and may further comprise dispersions or stabilizers.

The produced composition is dried, granulated, mixed with magnesium stearate, and compressed as a tablet form using conventional apparatuses. For example, aerosol formulation may be prepared by dissolving 5-400 mg of the compounds of the present invention in appropriate buffer solutions such as phosphates buffers, and if necessary, adding isotonic agents, for example salts such as sodium chloride to the solution. It is possible to remove impurities and contaminants by filtering the solution, for example, using 0.2 micrometer micro-filter.

Accordingly, one embodiment of the present invention comprises a pharmaceutical composition comprising the compounds or stereoisomers thereof or pharmaceutically acceptable salts thereof. Additional embodiment of the present invention comprises a pharmaceutical composition comprising the compounds or stereoisomers thereof or pharmaceutically acceptable salts thereof, and a pharmaceutically acceptable carrier or recipient.

The above-described gene medicine comprises a gene delivery vehicle including a nucleic acid molecule of interest. The gene delivery vehicle is manufacture in order to transport and express the nucleic acid molecule of interest. The detailed description for the nucleic acid molecule as a transportation object will be omitted in order to avoid over-writings with the above-mentioned description.

In order to manufacture the gene delivery vehicle, it is preferable that the nucleic acid molecule of interest exists within appropriate expression constructs. Within the expression constructs, it is preferable that the nucleic acid molecule of interest is linked operatively to a promoter. As used herein, the term "operatively linked" means a functional relationship between nucleic acid expression control sequences (e.g., promoter, signal sequence, or array at transcription control element binding sties) and other nucleic acid sequences, the control sequence regulates the transcription and/or translation of the other nucleic acid sequences through operatively links. In the present invention, the promoters, which are linked to the nucleic acid molecule of interest, are operated preferably in animal cells, more preferably mammalian cells in order to control transcription of the nucleic acid molecule of interest. The promoters comprises, but are not limited to, promoters derived from mammalian viruses or from the genomes of the mammalian cells, for example, CMV (cytomegalo virus) promoter, adenovirus late promoter, vaccinia virus 7.5K promoter, SV40 promoter, HSV tK promoter, RSV promoter, EFL alpha promoter, metallothionein promoter, beta-actin promoter, promoter for human IL-2 gene, promoter for human IFN genes, promoter for human IL-4 gene, promoter for human lymphotoxin gene, promoter for human GM-CSF gene, cancer cell specific promoters (e.g., TERT promoter, PSA promoter, PSMA promoter, CEA promoter, E2F promoter and AFP promoter), and tissue specific promoters (e.g., albumin promoter). Preferably, the expression construct used in the present invention comprises poly-adenylation signal sequence (e.g. bovine growth hormone terminator and SV40 derived poly-adenylation sequence).

Gene delivery vehicles may be manufactured in various shapes, for example, 1) naked (recombinant) DNA molecules, 2) plasmids, 3) viral vectors and 4) liposome or niosome nesting the naked (recombinant) DNA molecules or the plasmids. When DNA is in a naked state, DNA is coated with biodegradable beads in order to transfer DNA further efficiently into cells (Ulmer et al., 1993, Science 259: 1745-1749; Cohen, 1993, Science 259: 1691-1692).

The nucleic acid molecule of interest may be applied to any of gene delivery systems used in conventionally gene therapy, preferably applied to plasmid, adenovirus (Lockett L J. et al., Clin. Cancer Res. 3: 2075-2080, 1997), adeno-associated virus (AAV; Lashford L S. et al., Gene Therapy Technologies, Applications and Regulations Ed. A. Merger, 1999), retrovirus (Gunzburg W H, et al., Retroviral vectors. Gene Therapy Technologies, Applications and Regulations Ed. A. Merger, 1999), Lentivirus (Wang G. et al., J. Clin. Invest. 104(11): R55-62, 1999), herpes simplex virus (Chamber R., et al., Proc. Natl. Acad. Sci. USA 92: 1411-1415, 1995), vaccinia virus (Puhlmann M. et al., Human Gene Therapy, 10: 649-647, 1999), baculovirus (King L A. And Possee R D., The Baculovirus Expression System, Springer, 1992), liposome (Methods in Molecular Biology, Vol. 199, S. C. Basu and M. Basu (Eds.), Human Press, 2002) or niosome.

Transducing the above-described gene delivery vehicle into cells may be performed through various processes known in the art. In case the gene delivery vehicle is prepared based upon viral vectors in the present invention, it is possible to adopt processes using viral infections known in the art so as to transduce the gene delivery vehicle. The infection of the host cells using viral vectors are described in the above-described documents.

In case the gene delivery vehicle is naked recombinant DNA or plasmids in the present invention, it is possible to transfer genes by a micro injection (Capecchi, M. R., Cell. 22: 479, 1980; and Harland & Weintraub, J. Cell Biol. 101: 1094-1099; 1985); calcium phosphate precipitation (Graham, F. L. et al., Virology, 52: 456, 1973; Chen & Okayama, Mol. Cell Biol., 7: 2745-2752, 1987); electroporation (Neumann, E. et al., EMBO J., 1: 841, 1982; and Tur-Kaspa et al., Mol. Cell Biol., 6: 716-718, 1986); liposome-mediated transfection (Wong, T. K. et al., Gene, 10: 87, 1980; Nicolau & Sene, Biochim. Biophys. Acta, 721: 185-190, 1982; and Nicolau et al., Methods Enzymol., 149: 157-176, 1987); DAEA-dextran treating method (Gopal, Mol. Cell Biol., 5: 1188-1190, 1985); and gene bombardment (Yang et al., Proc. Natl. Acad. Sci., 87: 9568-9572, 1990).

Hereinafter, while the present invention will be described in more detail through various examples, the present invention is not limited to inventions described in the following examples.

Example 1: Expression Measurement of Upstream Regulatory Factors for CIITA by IK Factor Fragments 1) Screening Active Sites of IK Factor We screened active sites of IK factor using computer program. We screened the active sites by inputting and setting an amino acid sequence of a truncated fragment IK factor (tIK) of SEQ ID NO: 3 at in silico program 'scanlite' which is provided at a website scansite.mit.edu/motif-scan_seq.phtml. All motif analysis data are based upon SWISS-PORT database. The screening result for the active sites of IK factor is shown in Table 1 below. In table 1, 'score' is a numerical value of actual interaction of the sites of IK factor with kinase, and 'percentile' is a numerical value showing what percentage the kinase motif associated with tIK among kinase motifs in SWISS-PROT database in top high rank is. Both 5382 site and Y482 site are motif candidates presented in the all screening conditions, high/ medium/low stringency conditions, and Y489 site is a motif candidate present in the screening conditions, medium/low/stringency conditions.

TABLE 1

Screening of Active Site of IK Factor

| Score | per-centile | Motif | Motif group | site | Sequence |
|---|---|---|---|---|---|
| 0.482 | 0.416% | Aurora A (AuroA) | Baso_ST_kin[a] | S382 | EKKPHSYF EKPKV |
| 0.392 | 0.273% | PKC Epsion (PKC-epsion) | Baso_ST_kin[a] | S382 | EKKPHSYF EKPKV |
| 0.323 | 0.177% | (PKA_kin)[b] | Baso_ST_kin[a] | S382 | EKKPHSYF EKPKV |
| 0.408 | 0.163% | Grb2 SH2 (Grb2_SH2) | SH2[c] | Y492 | TQEEYSEY MNNKEAL |
| 0.574 | 0.378% | InsR_Kin[d] | Y_Kin[e] | Y489 | DFDTQEEY SEYMNNK |
| 0.484 | 0.638 | Src_Kin[f] | Y_Kin[e] | Y489 | DFDTQEEY SEYMNNK |

[a]Basophilic serine/threonine kinase;
[b]Protein Kinase A;
[c]Src homology 2 group;
[d]Insulin Receptor Kinase;
[e]Tyrosine kinase group;
[f]Src Kinase.

2) Design of Nucleic Acid Fragments Excised Some Nucleotides

As shown schematically in FIG. 2, we designed tIK nucleic acid fragments and variant tIK nucleic acid fragments that have mutants substituted other amino acids for the amino acid of the active sites based upon the screening result in 1). A gene fragment of SEQ ID NO: 3 as a tIK nucleic acid fragment was used, and point mutation nucleic acid fragments that is substituted structurally similar amino acids for the amino acids (S382, Y489, and Y492), which are expected to play an important role in the functions of IK as kinase motifs, were prepared.

A mutant gene fragment (S382A), which has substituted nucleotides 'GCC' encoding alanine for the nucleotide residues encoding the 382$^{nd}$ amino acid residue Serine of SEQ ID NO: 2 (the 1144-1146$^{th}$ nucleotide residues of SEQ ID NO: 1), was prepared. Also, both a mutant gene fragment (Y489F), which has substituted nucleotides 'TTC' encoding phenylalanine for the nucleotide residues encoding the 489$^{th}$ amino acid residue Tyrosine of SEQ ID NO: 2 (the 1465-1467$^{th}$ nucleotide residues of SEQ ID NO: 1), and a mutant gene fragment (Y492F), which has substituted nucleotides 'TTC' encoding phenylalanine for the nucleotide residues encoding the 492$^{nd}$ amino acid residue Tyrosine of SEQ ID NO: 2 (the 1474-1476$^{th}$ nucleotide residues of SEQ ID NO: 1), were prepared.

Simultaneously, a dual mutant gene fragment (Y489492F), which has substituted nucleotides encoding phenylalanine for the nucleotide residues encoding 489$^{th}$ and the 492$^{nd}$ amino acid residues Tyrosine of SEQ ID NO: 2, and a triple mutant gene fragment (S382AY489492F), which has respectively substituted nucleotides encoding alanine for the nucleotide residues encoding the 382$^{nd}$ amino acid Serine of SEQ ID NO: 2 and nucleotides encoding phenylalanine for the nucleotide residues encoding the 489$^{th}$ and the 492$^{nd}$ amino acid residues Tyrosine of SEQ ID NO: 2, were also prepared. A HA-tag sequence (haemagglutinin sequence; SEQ ID NO: 54) was added at 5'-end of each gene fragment for detecting, isolating and purifying the expressed proteins. Nucleotide sequences for the tIK nucleic acid fragment and the mutant nucleic acid fragments are shown in Table 2 below.

TABLE 2

IK nucleic acid fragment and mutant nucleic acid fragments

| Fragment | Nucleotide sequence | Amino acid sequence | Note |
|---|---|---|---|
| tIK | SEQ ID NO: 3 | SEQ ID NO: 4 | |
| S382A | SEQ ID NO: 5 | SEQ ID NO: 6 | Ser → Ala |
| Y489F | SEQ ID NO: 7 | SEQ ID NO: 8 | Tyr → Phe |
| Y492F | SEQ ID NO: 9 | SEQ ID NO: 10 | Tyr → Phe |
| Y489492F | SEQ ID NO: 11 | SEQ ID NO: 12 | Tyr → Phe |
| S382AY489492F | SEQ ID NO: 13 | SEQ ID NO: 14 | Ser → Ala; Tyr → Phe |

The tIK fragment and the mutant nucleic acid fragments were prepared by inserting inserts, which were amplified using fusion PCR method, into pcDNA 3.1 vectors. With regard to a S382 mutant, both a forward primer complementary to HA tag to a 5'-region of a tIK nucleic acid and a reverse primer having a nucleotide sequence encoding alanine in order to substitute the 382th Serine for alanine were prepared and used in PCR. The first gene fragment consisting of the HA tag sequence to a nucleotide encoding the 382$^{nd}$ alanine (Ala) was amplified using such primer sets and tIK gene as a template. And then, a forward primer including a nucleotide encoding alanine in order to replace the 382$^{nd}$ serine with alanine, and a reverse primer complementary to the 3'-end region of tIK gene were prepared so that the second gene fragment consisting of the nucleotides encoding the 382$^{nd}$ alanine to 3'-end of tIK nucleic acids. 1 µL of each of two gene fragments obtained by PCR was added to 500 µL micro tube, 1 µL of each of another forward primer complementary nucleic acids from HA tag sequence to 5'-end region of tIK gene and another reverse primer complementary to 3'-end of tIK gene was added to the micro tube, and then polymerase buffer, dNTPs, polymerase, and distilled water was added to perform fusion PCR. The ends of the amplified fragments obtained by fusion PCR was cut by restriction enzymes and the amplified fragments were inserted into pcDNA 3.1 for the transformation, and plasmids including the inserts with the substituted amino acids were screened, and finally certified whether the plasmids has the substituted amino acid through sequencing. Other mutants were prepared using the same processes as described above. Table 3 shows the primer sets which were used for the amplification of the tIK nucleic acid fragment and the mutant nucleic acid fragments according to the present example.

TABLE 3

Primer Sets Used in Amplification of tIK nucleic acid fragment and mutant nucleic acid fragments

| Plasmid (HA tagged) | 1$^{st}$ fragment primer | 2$^{nd}$ fragment primer |
|---|---|---|
| tIK | Forward: SEQ ID NO: 15[a] Reverse: SEQ ID NO: 16[b] | |

TABLE 3-continued

Primer Sets Used in Amplification of tIK nucleic acid fragment and mutant nucleic acid fragments

| Plasmid (HA tagged) | 1st fragment primer | 2nd fragment primer |
|---|---|---|
| S382A | Forward: SEQ ID NO: 17[a] Reverse: SEQ ID NO: 19 | Forward: SEQ ID NO: 20 Reverse: SEQ ID NO: 16 |
| Y489F | Forward: SEQ ID NO: 18[c] Reverse: SEQ ID NO: 21 | Forward: SEQ ID NO: 22 Reverse: SEQ ID NO: 16 |
| Y492F | Forward: SEQ ID NO: 17 Reverse: SEQ ID NO: 23 | Forward: SEQ ID NO: 24 Reverse: SEQ ID NO: 16 |
| Y489492F | Forward: SEQ ID NO: 18[c] Reverse: SEQ ID NO: 25 | Forward: SEQ ID NO: 26 Reverse: SEQ ID NO: 16 |
| S382AY489492F | S67A fragment and Y174_177F fragment were used as a template. Obtained insert having triple mutations using SEQ ID NO: 18[c] as a forward primer and SEQ ID NO: 16 as a reverse primer. | |

[a]including EcoRI recognition site;
[b]including XhoI recognition site;
[c]including HindIII recognition site.

We certified the tIK and mutant nucleic acids by analyzing mRNA expression levels of upstream regulatory elements each of which control an expression of class II coactivator, CIITA that facilitates the expression of MHC class II. We selected CNOT1 (CCR4-NOT transcription complex subunit 1), CDCA3 (Cell division cycle-associated protein 3) and MAPK1 (Mitogen-activated protein kinase 1) as an upstream regulatory factor regulating the expression of CIITA. It was certified that the expression level of the factors (CNOT1, CDCA3, and MAPK1) which suppress the expression of CIITA was increased in case of transfecting plasmids having inserted tIK gene into human Raji B cells without intrinsic tIK factor, compared to a negative control group transfecting a control vector into the cells. It was considered that the tIK nucleic acid fragment increases the expression of factors suppressing CIITA, and thereby, having an effect upon the inhibition of the MHC class II expression. And then, we certified if there exist the same phenomena in the tIK mutant nucleic acid fragments, which has substituted amino acids for the amino acid of kinase motifs, based upon such analyses.

Concretely, plasmids each of which have an inserted tIK mutant fragment, S382A, Y489F, Y489492F, and S382AY489492F, respectively, were transfected into Raji B cells using electroporation, and then RAN was isolated in order to prepare cDNA. A plasmid inserting a tIK nucleic acid fragment was also used, and cDNA obtained by transfecting pcDNA 3.1 plasmid without inserted any of the nucleic acid fragments into the cells were used as a negative control. Quantitative real-time PCR was performed using the prepared cDNA, and the measured values (Ct values) were calculated as relative values based upon the result in the negative control group transfected with pcDNA 3.1 plasmid, using $2^{(-\Delta\Delta Ct)}$ method. We used cDNA of the factors (CDCA3, CNOT1, and MAPK1) regulating the expression of CIITA as templates, and the Primers sets used in certifying the expression of such factors are shown in Table 4.

TABLE 4

| CIITA regulator factor | Forward primer | Reverse primer |
|---|---|---|
| CDCA3 | SEQ ID NO: 27 | SEQ ID NO: 28 |
| CNOT1 | SEQ ID NO: 29 | SEQ ID NO: 30 |
| MAPK1 | SEQ ID NO: 31 | SEQ ID NO: 32 |

FIG. 3 shows experimental results of measuring expression levels of the factors regulating CIITA expression. We found that expression levels of all the CDCA-suppressing factors, CDCA3, CNOT1 and MAPK1 were increased in the tIK transfected group, compared to the result in the group of transfecting a negative control vector pcDNA 3.1. The expression levels of CIITA-suppressing factors were relatively reduced in mutants such as Y492F, Y489492F, S382AY489492F, each of which substituted other amino acids for the active amino acids, compared to the positive control group, tIK insert group. Particularly, 5382 and Y489 mutants reduced considerably the expression levels of CIITA-expression suppressive genes, which had been increased by the expression of tIK gene. Accordingly, we certified that the $382^{nd}$ and the $492^{nd}$ amino acids in the full-length IK factor particularly act as active sites for the physiological functions of IK factor.

Example 2: Construction of Animal Model Using IL-1 Receptor Antagonist Knock-Out Mice and IK Transgenic Mice A novel animal model (tIK-IL1RaKO mice), which induces autoimmune arthritis, was manufactured by crossbreeding an animal model, IL-1 receptor antagonist knock-out mouse (IL1RaKO mice, derived from Balb/c), which exhibits high immunological sensitivity and occurs autonomous arthritis in order to increase sensitivity to arthritis-inducing molecules, and tIK-transgenic mice (tIK, derived from Balb/c), which can express a nucleic acid molecule which has a nucleotide sequence of SEQ ID NO: 3 and encodes the truncated IK factor (tIK fragment). In order to manufacture transgenic mice expressing truncated IK factor (tIK), tIK-pcDNA 3.1 clones into which a nucleic acid molecule of SEQ ID NO: 3 is inserted were micro-injected into fertilized ova extracted from Balb/c female mouse. The ova were transplanted into the uterus of Balb/c female mouse at false pregnancy state so as to implant the ova, and offsprings were obtained 3 weeks later. In order to obtain the mouse gene through cross-breeding, the offsprings' tail were cut by 0.3 mm, tail lysis buffer (pH 8.0, Tris buffer 50 mM, EDTA 50 mM, 0.5% SDS in distilled water, 20 mg/mL proteinase K) was added and incubated in 55° C. constant-temperature water bath for 18 hours so as to obtain tail lysate.

The tail lysate was transferred to vacutainer, phenol/chloroform/isoamylalcohol (25:24:1) was added into the vacutainer, the vacutainer was inverted 50 times, and then the vacutainer was centrifuged (2,000 rpm, 5 minutes, room temperature) so as to remove the rest debris except genomic DNA. Chloroform was added to the centrifuged vacutainer, and then the vacutainer was inverted again, and then centrifuged (2,000 rpm, 5 minutes, room temperature) to separate only a genomic DNA layer. Transparent supernatant obtained by the isolation was transferred to another micro tube, 100% ethanol was added to the micro tube, and the micro tube was inverted to obtain genomic DNA of white skein shapes. The obtained genomic DNA was picked up using a pipette tip, washed in 75% ethanol, air-dried for 10 minutes, and then dissolved in distilled water. The first amplicon was amplified by PCR using the genomic DNA, extracted from the transgenic mice into which tIK nucleic acid fragments are inserted, as a template and primer sets for tIK genotyping (Forward Primer: SEQ ID NO: 33; Reverse Primer: SEQ ID NO: 34). The second amplicon was amplified by PCR using primer sets for IL1RaKO genotyping (Forward Primer: SEQ ID NO: 35; Reverse Primers: SEQ ID NOs: 36/37). Two amplicons were obtained through electrophoresis assay in 1% agarose gel to certify the amplification levels. In case both amplicons were detected in the electrophoresis results, it was certified that the genomic DNA was extracted from tIK-IL1RaKO double positive transgenic mice obtained through the cross-breeding.

Example 3: Efficiency Assay of IK Using Autoimmune Arthritis Animal Model

We monitored the inducing levels of arthritis in tIK-IL1RaKO mice, new autoimmune arthritis animal model obtained by cross-breeding in Example 2, and IL1RaKO mice. In order to compare the arthritis-inducing levels in a natural state, 10 4-week-old tIK-IL1RaKO mice and 10 4-week-old IL1RaKO mice were fed in cages in the same conditions. During the feeding time, we scored the arthritis levels by observing arthredema levels in ankle sites of the mice in every week. Detailed scoring method is as follows: Arthritis assessment tests were recorded based upon mean arthritis index by Rosoliniec et al. And monitoring was proceeded continuously three times in a week. We scored paws for arthritis levels on a scale of 0 to 4 and summed the paw scores to yield individual mouse scores. The joint arthritis scores were evaluated blindly as follows: grade 0, no swelling; grade 1, slight swelling and erythema; grade 2, pronounced swelling; grade 3, joint rigidity; grade 4, maximal swelling. Each limb was graded as a score of 0-4, with a maximum possible score of 16 for each mouse. Also, arthritis-occurring levels were monitored so as to show incidence rate by the feeding period. FIG. 4A is a graph showing a result of measuring arthritis index, and FIG. 4B is a graph showing a result of measuring arthritis incidence rate. Also, FIG. 5 is photographs showing joints observed in each mouse group. As shown in those figures, we found that the tIK-IL1RaKO mice group exhibited significantly less arthritis index than the IL1RaKO mice group, and low arthritis incidence rate of less than 60%. Also, we found that the tIK-IL1RaKO mice group showed alleviated arthritis level in ankle joints compared to the IL1RaKO mice group.

Example 4: Certification of Pathogenic States of Joints in Mice

In order to certify the pathogenic states of the arthritis induced mice, an autopsy for the mice of each group (tIK-1RaKO group; and IL1RaKO group) was done after 16-week monitoring for the spontaneously induced arthritis groups so as to obtain joint tissues. The joint tissue was fixed in 10% neutral formalin, dipped in decalcification solution for 7 hours. The decalcificated joint was washed in water for 16 hours, dehydrated, de-alcoholized, and infiltrated to prepare a paraffin block. The paraffin block was cut using a section apparatus so as to obtain 7 mm section, and the section was attached to a slide for staining using hematoxylin & eosin (H&E staining) Staining process is as follows: deparaffinization was performed from the paraffin section, an enhydrous procedure was performed, and then nucleus of the cells was stained with hematoxylin. After washing it, cytoplasm was stained with eosin. Such stained cells were again dehydrated, de-alcoholized, and included, so as to certify the structural state of tarsal bone around the ankle and infiltrations by various immune cells. The results are shown in FIG. 6A. it was shown that the joint tissues extracted from tIK-IL1 RaKO mice has less structural changes and occurs less infiltrations compared to the joint tissues extracted from IL1RaKO mice. We certified that synovial inflammations are less occurred in the tIK-IL1RaKO mice by those results.

Also, we certified the cartilage erosions extracted from the mice group using safranin O staining Safranin O staining was performed subsequently by deparaffinization of the tissue section, enhydrous process, hematoxylin staining, safranin O staining, fast green staining, dehydration, de-alchoholization, inclusion. The results are shown in FIG. 6B. It is possible to certify the infiltration level in cartilage through color changes in the stained site. We certified that the most of the joint tissues extracted from IL1RaKO mice were damaged while cartilages in the joint tissues extracted from tIK-IL1 RaKO mice were maintained in undamaged state.

Example 5: Analysis of Bone Damages Level by Arthritis

In order to analyze comparatively the bone damages owing to inflammation in the spontaneously induced arthritis mice between the IL1RaKO mice group and the tIK-IL1RaKO mice group, an autopsy for the mice of each group was done after 16-week monitoring for the spontaneously induced arthritis groups so as to obtain joint tissues. The tissue was fixed in 10% neutral formalin for 18 hours for the micro CT imaging, which was performed using ex vivo micro CT scanner (Skyscan 1172). The sectional images of the tissues were photographed using X-ray source of 50 kV voltages and 200 µA currents and 15 µm resolution, and 0.5 mm filter. We observed that there are much bone damages and structural modifications in the tissue extracted from IL1 RaKO mice, while the tissue extracted from the tIK-IL1 RaKO mice maintains an original structure having little bone damages (FIG. 7). We certified that the expression of IK factor plays a role in suppressing the bone destruction by arthritis by the results.

Example 6: Certification of Inflammatory Cytokine Expression in Joint (1) Certification of mRNA Expression In order to certify expression levels of inflammatory cytokines at the joint in spontaneously induced arthritis mice, an autopsy for the mice of each group was done after 16-week monitoring for the spontaneously induced arthritis groups so as to obtain joint tissues. Joints were grinded in $LN_2$ and added in 400 µl of Trizol reagent to proceed with RNA isolation. Chloroform was added to the tissue and performed vortex strongly, and then the solution was incubated at room temperature for 5 minutes. After centrifuging (12,500 rpm, 15 min. 4° C.) the solution, supernatant was transferred to another micro tube. After adding isopropanol and glycoblue to the supernatant, the supernatant was incubated for 5 minutes. After another centrifugation (12,500 rpm, 10 min., 4° C.), the supernatant was filtered out. Pellet out of the supernatant was washed in 70% ethanol, was centrifugated (9,500 rpm, 5 min., 4° C.), and then air dried and dissolved in DEPC-water. Separated DNA was prepared as cDNA using QuantiTech Reverse Transcription kit (Quiagen). Quantitative real-time PCR was performed using the prepared cDNA (cDNA 1 μL, each of primer set 1 μL, 2XSYBR green mix 12.5 μL, Distilled water 9.5 μL, 40 cycles).

The measured result value (Ct value) per group was calculated as a relative value based upon the result in the wild type mouse group using $2^{(-\Delta\Delta Ct)}$ method. We measured the expressions of the inflammatory cytokines (IL-1β, IL-16, and IL-17A) each of which is known to increase in the case of arthritis development, using the cDNA as a template. Primers for used in amplifying the inflammatory cytokines (IL1β, IL-16, and IL-17A) using the cDNA as a template are shown in Table 2, and measuring results are shown in FIG. 8A.

TABLE 5

| Inflammatory cytokine | Forward primer | Reverse primer |
| --- | --- | --- |
| IL-1β | SEQ ID NO: 38 | SEQ ID NO: 39 |
| IL-6 | SEQ ID NO: 40 | SEQ ID NO: 41 |
| IL-17A | SEQ ID NO: 42 | SEQ ID NO: 43 |

We observed that the inflammatory cytokines (IL-1β, IL-6) that are involved in inducing joint inflammation were much expressed in the joint of the IL1RaKO mice than the joint of the tIK-IL1RaKO mice. Also, IL-17, which is a major factor suppressing substrate expressions within cartilage cells and osteoblasts, inducing joint damages, and making tissue regeneration deficient, were expressed remarkably lower in the joint of the tIK-IL1RaKO mice. We certified that the nucleic acid fragments derived from IK gene may regulate expressions of inflammatory cytokines expressed in inducing arthritis, and therefore, may lower arthritis values.

(2) Certification of Cytokine Expressions Using Tissue Staining

In order to certify pathogenic states of the joints in spontaneously induced arthritis mice, an autopsy for the mice of each group (tIK-IL1RaKO mice group; and IL1RaKO mice group) was done after 16-week monitoring for the spontaneously induced arthritis groups so as to obtain joint tissues. The joint was fixed in 10% neutral formalin, dipped in decalcification solution for 7 hours. The decalcificated joint was washed in water for 16 hours, dehydrated, de-alcoholized, and infiltrated to prepare a paraffin block. The paraffin block was cut using a section apparatus so as to obtain 7 mm section, and the section was attached to a slide for performing staining inflammatory cytokines (IL-17, IL-1β, and TNF-α). Deparaffinization was performed from the paraffin section, and enhydrous procedure was performed. After attaching a primary antibody for IL-1, IL-1β, and TNF-α for 16 hours, secondary antibody with labeled biotin was attached. After incubating in ABC reagent and developing colors was performed using peroxidase substrate solution, and washed in water. And then, we certified expressions of the inflammatory cytokines around the joint synovial sites and observed with a microscope. The result are shown in FIG. 8B. We observed that there is less infiltration by immune cells, especially immune cells induced owing to IL-17, within the synovial sites in the joint tissues extracted from the tIK-IL1RaKO mice, compared to the joint tissues extracted from the IL1RaKO mice. We certified that synovial inflammation was occurred little in tIK-IL1RaKO group by the result.

Example 7: Certification of Expression Inflammatory Cytokines in Serum

In order to certify expression levels of inflammatory cytokines within a blood in the spontaneously induced arthritis mice, an autopsy for the mice of each group was done after 16-week monitoring for the spontaneously induced arthritis groups so as to obtain a blood through heart blood collection. The obtained blood was centrifugated (4,000 rpm, 15 min., 4° C.) so as to separate a serum, and we certified expression levels of inflammatory cytokines in serum through ELISA assay using it.

Describing MCP-1 ELISA kit (R&D system) as an example, standard, which was provide with the kit, was added in serial to a plate where anti-MCP-1 primary antibody was pre-coated, and then, serum stock solution was added to a well and incubated for 2 hours. After completing the incubation, all samples added into the well was removed, and the serum was washed with 0.5% PBST (Phosphate Buffered Saline Tween-20) four times. Conjugate solution, which can bind to MCP-1 bonded to the anti-MCP-1 antibody in well, added to the well and incubated at room temperature for 2 hours. After incubation, substrate solution was added and monitored if the substrate solution was reacted with the conjugate to develop colors. when the coloring levels of serum samples for measuring were within the standard color developing ranges, stop solution (2N $H_2SO_4$) was added, and then, we measured the obserbance at 459 nm wave-length using ELISA reader. It was possible to MCP-1 concentrations indicated by the obserbance of the sample based upon the absorbance of the standard concentration. Using the same process, we measured the concentrations of other cytokines except of MCP-1. In order to amplify a MCP-1 cytokine gene, a forward primer of SEQ ID NO: 44 and a reverse primer of SEQ ID NO: 45 were used, and other cytokine genes were amplified using the same primer sets described in example 6.

Assay results are shown in FIG. 9. Similarly to the results of the inflammatory cytokine expression levels in the joint in example 6, we certified that all of MCP-1, a kind of Chemokine, IL-6, which is known to be involved in differentiation of pathogenic T cells, and IL-17, a major factor of arthritis development, was expressed in significantly lower in the serum of the tIK-IL1RaKO mice compared to the serum of the IL1RaKO mice. It was expected that tIK may have influences on systemic immune responses so as to contribute to lowering arthritis values.

Example 8: Measurement of Expression of Pathogenic T-helper Cells

It has been well-known that T cells of immune cells are major cells inducing disturbances of immune system. Activated T cells are differentiated into effector T cells such as Th1, Th2, Th17, and regulatory T cells. The developments and the progresses of disorders depend upon which differentiation paths are facilitated. Each of Th1 cell and Th17 cell secretes, respectively, IFN-γ and IL-17, and has been known to form main pathologies in inflammatory disorders such as diabetics, rheumatoid arthritis, and Crohn's disease.

In this case, we certified whether or not expressions of the pathogenic T cells are involved when arthritis is suppressed by the nucleic acid fragments derived from IK factor. An autopsy for the mice of each group was done after 16-week monitoring for the spontaneously induced arthritis groups so as to obtain a spleen. 100 μm of strainer was added to 100 mm Petri dish containing serum free RPMI media, and the spleen was placed onto the strainer. The spleen was tore into pieces using a syringe needle so that immune cells of the spleen passes into the dish containing media through the strainer. After grinding all spleen, immune cells spreading on the media was collected into a tube, and centrifugated (1,500 rpm, 5 min, 4° C.) so as to obtain only pellet. Red blood cell lysis buffer was added to the pellet and incubated at 4° C. for 5 minutes. Again, the solution was centrifugated (1,500 rpm, 5 min, 4° C.) so as to remove red blood cells, and finally to obtain splenocyte. After suspending the splenocyte in RMPI media containing FBS, 1×10$^6$ cells were chosen, and then, staining process were proceeded in order to analyze an amount of pathogenic T cells by flow cytometry. PMA (100 ng/mL) and ionomycin (200 ng/mL) was added to splenocyte obtained by per group, and was incubated for 4 hours, and then, golgi stop agent for staining intracellular IL-7 were added. The stimulated cell by PMA and ionomycin was washed in cold PBS, an antibody (PE-Cy5 conjugated) to a cell surface molecule of Th17 cells, CD4, was added to react at 4° C. for 30 minutes, and then the mixture washed in cold PBS. After increasing cellular permeability for transferring antibody into the cells and staining intracellular IL-17, another antibody (PE conjugated) to IL-17 was added to react at room temperature for 30 minutes. After completing all reactions, the mixture was washed using fixative solution, and finally the stained cells were fixed in 1% paraformaldehyde so as to use the cell in flow cytometry assay.

Th1 cells secreting IFN-γ were detected in 6.09% in the IL1RaKO mice but they were detected relatively lower amount of 3.24% in the tIK-IL1RaKO mice (See, FIG. 10A). Similarly, Th11 cells secreting IL-17 were detected in 1.78% in the IL1RaKO mice but they were detected 1.2% in the tIK-IL1RaKO mice, which means that pathogenic Th17 cells were expressed in a reduced amount of 1.5 times in the tIK-IL1RaKO mice compared to the IL1RaKO mice (See, FIG. 10B).

Such assay results accord with the expression analysis results for the inflammatory cytokines, which are known to be involved in differentiation of Th17 cells, certified in joints and sera extracted from the mice in examples 6 and 7. Accordingly, we certified that the nucleic acid fragments derived from IK factor can suppress the expressions of Th17 cells and Th1 cells, which are mainly concerned with inflammatory responses in case of developing arthritis, so that the fragments can inhibit the inflammatory responses owning to arthritis.

Example 9: Macrophage Activating Factor Expression Assay

Macrophages activated by rheumatoid arthritis secrete various inflammatory cytokines and interacts with various immune cells so as to initiate and maintain immune responses in joints. Macrophage induces an activation of T cell by presenting antigen with the T cell as well as an activation of osteoclasts by secreting various cytokines Because macrophage plays an important role in maintaining inflammatory responses caused by arthritis, we certified if macrophage is concerned with arthritis suppression by IK factor in this example.

An autopsy for the mice of each group (IL1RaKO mice and tIK-IL1RaKO mice) was done after 16-week monitoring so as to obtain a spleen as in example 8. The obtained splenocyte were stained using macrophage factor CD11b antibody (APC conjugated), pathogenic macrophage factor F4/80 antibody (PE-cy7 conjugated) and macrophage activating factor CD86 antibody (FITC conjugated). The stained cells were fixed in 1% paraformaldehyde solution so as to use the cell in flow cytometry assay. As shown in FIG. 11, the expressions of macrophage activating factors were reduced in the splenocyte extracted from the tIK-IL1RaKO mice compared to the splenocyte extracted from the IL1RaKO mice. Accordingly, we certified that expression of IK factor has an influence on the macrophage activation suppression as well as Th17 cell.

Example 10: Synthesis of Active Peptides and Certification of Macrophage Activation Suppression We prepared short-length active peptides, which can be expressed and purified with ease compared to tIK factor, as partial fragments of IK factor so as to certify whether the peptides exhibit physical functions in case of applying them to the arthritis animal models. We synthesized the peptides including two amino acids (S382 and Y489 of SEQ ID: NO 2) which were expected to play an important role in function of IK factor in example 1. A peptide (SEQ ID NO: 47, S peptide) consisting of 14 amino acids comprising S382 and another peptide (SEQ ID NO: 48, Y peptide) consisting of 13 amino acids comprising Y489 were synthesized. In this case, each of S382 and Y489 were phosphorylated. Each active peptide was synthesized using Fmoc solid phase synthetic method. During the synthetic process, we removed residual agents were removed by repeating coupling-washing-deprotection-washing steps and used COMDEL device as a multi-channel automated synthesizer. Each active peptide was synthesized in the direction from C-terminal to N-terminal by the synthetic process. After completing all reactions, the synthetic peptides were separated from resins using reagent K. Separated peptides were precipitated by adding cold diethyl ether, washed again using diethyl ether, and then dried in vacuum state. We measured molecular weights of the synthetic peptides using mass spectrometer, and performed purification in case only the measured molecular weights are identical as expected molecular weights. The purification was performed as follows: Reverse-HPLC; C18 column, 220 nm wavelength.

We certified the macrophage activation levels by placing the S peptide and Y peptide in conditions stimulated with lipopolysaccharide (LPS). After co-transfecting simultaneously 500 ng/mL of each of S peptide and Y peptide into J774a.1 macrophage cell-lines, the cell-lines were treated with LPS (O111:B4) for 24 hours in order to certify the expression of inflammatory cytokines. It was shown that mRNA expressions of the inflammatory cytokines (TNF-α, IL-6) in macrophage, which was treated LPS for 24 hours, was reduced in the active peptides treating group (See FIG. 12A). In the measurements for the culture media, the inflammatory cytokines were expressed lower in the tIK active peptide treating group (See, FIG. 12B). Accordingly, we certified that the active peptides suppress the expressions of inflammatory cytokines associated with arthritis.

Example 11: Certification of Pathogenic T Helper Cell Differentiation by Active Peptides In order to certify whether or not the IK factor active peptides have an influence on the differentiation of pathogenic T cells, splenocytes were extracted from wild type mouse as in Example 8. Only naïve CD4 T cells were selectively separated from the splenocytes, and then were pre-treated with S peptide and Y peptide (100 ng/mL or 500 ng/mL) for 1 hour. Culture media comprising various cytokines, which can be differentiated into pathogenic T cells, and neutral antibodies were added, and the same concentration of S peptide and Y peptide (100 ng/mL or 500 ng/mL) was added again when condition culture media was added. Culture media containing anti-CD3, anti-CD28 and IL-2 were added to the splenocytes for inducing differentiating to Th0 cells. Culture media containing anti-CD3, anti-CD28, IL-2, IL-12, and anti-IL14 were added to the splenocytes for inducing differentiating to Th1 cells. Also, culture media containing anti-CD3, anti-CD28, IL-6, TGF-β, anti-IL-4, and anti-IFN-γ were added to the splenocytes for inducing differentiating to Th17 cells. After culturing 2 days, culture media containing various cytokines and neutral antibodies were added to the cells at the same conditions for differentiating to pathogenic T helper cells. After 2 days, the pathogenic T helper cells were stained for flow cytometer assay.

First, phrobol 12-myristate-13-acetate (PMA, 50 ng/mL) and ionomycin (200 ng/mL) was added to the cultured cells. After incubating at 37° C. for 4 hours, golgi stop (monensin) for staining intracellular IL-17 was added. After incubation, the cells were washed cold PBS. After increasing cellular permeability for transferring antibody into the cells for staining intracellular cytokines (IL-17 and INF-γ), antibodies to IL-17 and IFN-γ was added and reacted for 30 minutes on ice. After completing the reaction, the cells were washed in fixative solution, and finally the stained cells were fixed in 1% paraformaldehyde solution for using flow cytometer assay. As shown in FIGS. 13A and 13B, we found that the differentiation to IFN-γ-expressing CD4+ helper cells were inclined to reduce in a Th0 cell differentiation condition and a Th1 cell differentiation conditions in the active peptide treating mince. Also, as shown in FIG. 13C, we found that treating active peptides suppressed the differentiation to IL-17-expressing CD4+ T cells. Such results means that short peptides with active site amino acids of IK factor can suppress the differentiations to pathogenic T helper cells such as Th1 cells or Th17 cells in inflammatory disorders.

Example 12: Arthritis Suppression Through Injection of Active Peptides

We injected active peptides into the spontaneously induced arthritis model (IL1RaKO mice) in order to assess if the active peptides of IK factor, S peptide and Y peptides, suppress arthritis. 7 IL1RaKO mice were used in each group. As active peptides, total 10 mg/kg of peptides (S peptide: 5 mg/kg; Y peptide: 5 mg/kg) were injected by intraperitoneal injection. As a negative control, same volume of phosphate buffed saline (PBS) was injected by intraperitoneal injection. Peptides were injected by every 2-3 day, and we monitored mice' weights, arthritis development levels and indices in injecting the peptides for 7 weeks. We found that the arthritis index in the peptide-treated mice group was lower than that in the negative control group which was injected by PBS (See, FIG. 14A), and that the incidence rate of arthritis was relatively lower in the peptide-injected mice group (See, FIG. 14B).

Example 13: Pathogenic T Cells Assay in Post-Injection Arthritis Model (1) Flow Cytometer Assay We measured the distribution of Th17 cells, which is a major factor in initiating and maintaining inflammatory responses by arthritis, by the injection of active peptides of IK factor. After 8 weeks of injecting active peptides according to example 12, an autopsy was done in order to obtain a spleen of each group. After extracting splenocytes by grinding the obtained spleen, PMA (50 ng/mL) and ionomycin (200 ng/mL) was added to the splenocytes. When incubating the splenocytes at 37° C. for 4 hours, golgi stop (monensin) for staining intracellular IL-17 was added. After incubating, the cells were washed in cold PBS, antibody (APC conjugated to surface molecule of pathogenic Th17 cells, CD4, was wadded, and then was reacted 4° C. for 30 minutes. After completing the reaction, the cells were washed. After increasing cellular permeability for transferring antibody into the cells and staining intracellular IL-17, another antibody (PE conjugated) to IL-17 was added to react at room temperature for 30 minutes. After completing all reactions, the mixture was washed in fixative solution, and finally the stained cells were fixed in 1% paraformaldehyde for flow cytometry assay.

Comparing assay results for the pathogenic Th17 cells in the splenocytes extracted from the arthritis-induced mice between the peptide-injected group and the PBS-injected group, there were less Th17 cells in the splenocytes extracted from the IL1RaKO mice injected by active peptides (See, FIG. 15A). Such results mean that active peptides of IK factor play an important role in suppressing the differentiation and proliferations of Th17 cells which is closely concerned with arthritis development.

(2) Certification of Cytokine Expression Using Tissue Staining

We certified the expressions of inflammatory cytokines in joint synovial sites after injecting IK active peptides. After 8 weeks of injecting active peptides according to example 12, an autopsy was done in order to obtain a spleen of each group. Joint were fixed in 10% neutral formalin, and was dipped in decalcification solution for 7 hours. The decalcificated joint was washed in water for 16 hours, dehydrated, de-alcoholized, and infiltrated to prepare a paraffin block. The paraffin block was cut using a section apparatus so as to obtain 7 mm section, and the section was attached to a slide, and then staining for inflammatory cytokines (IL-17, IL1-β and TNF-α) was performed. After de-parffinizing the paraffin section, an enhydrous procedure was performed. Primary antibodies to IL-17, IL1-β and TNF-α were attached to the section for 16 hours, and then secondary antibodies labeled biotin was attached. After incubating in ABC reagent, color developing process was performed using peroxidase substrate solution. And then, the mixture was washed in water. After certifying the expression of the inflammatory cytokines around the joint synovial sites, we observed the synovial sites with a microscope. The results are shown in FIG. 15B. We certified that inflammatory cytokines in joint were less expressed and infiltrations by inflammatory were remarkably reduced in the active peptide injected mice.

Example 14: Expression and Purification of tIK Using Baculovirus Expression System In order to express IK fragment (tIK) in a large quantity, tIK plasmid which inserts tagged FC sequence was transfected into baculovirus, and then tIK was expressed from insect cell (SF9 cell) infected with a recombinant baculovirus. A nucleic acid sequence (SEQ ID NO: 50) encoding thrombin recognition site and Fc tagging sequence (SEQ ID NO: 51) were linked to 3'-end of the tIK nucleic acid. After preparing viral seeds, baculovirus expressing tIK-Fc was infected into the insect cells of which amount are subsequently increased in the $1^{st}$ infection (100 mm dish scale), the $2^{nd}$ infection (T75 flask scale), and the $3^{rd}$ infection (1 L conical flask). Finally, after infecting the insect cells in the $3^{rd}$ infection for three days, 1 L of cell culture secreting tIK-Fc was obtained. The obtained tIK-Fc protein in the cell culture was purified using immuno-precipitation method. when rProtein A resin was added to Sepharose column and then cell culture was injected into the column, expressed Fc in tIK-Fc protein contained cell culture binds to the resin so that tIK-Fc protein were remained in the column. We certified the expression (~55 kDa) of the tIK-Fc protein using Commassie blue staining method (result not shown). In order to obtain pure tIK-Fc protein, we intended to separate the tIK-Fc region conjugates from the resin by severing non-covalent bonds between the Fc region and rProtein. In order to sever the non-covalent bonds, the protein was eluted using Elute Buffer (0.1M Glycine buffer, pH 2.8), and then neutralized by Neutralization buffer (1M Tris-HCl, pH 8.0) for preventing structural modifications of the protein. Column washing process was performed by using washing buffer (0.15M NaCl-20 mM $Na_2HPO_4$, pH 8.0). All separated solutions with 7 fractions were obtained by Affinity Chromatography assay. And then, we performed SDA-PAGE assay for the each solution of 7 fractions and certified the elution of the protein. We found that the protein analyzed in SDS-PAGE has 55 kDa as tIK-Fc conjugated from (See, FIG. 16).

Example 15: Construction of Recombinant Adeno-Associated Virus (rAAV) Vector System for tIK Gene Transfer Unlikely to retrovirus, since adeno-associated virus (AAV) does not cause disorders and integrates selectively into the 19th chromosome in human cells, it has been used as a gene therapy vector for chronic disease. Using those characteristics of AAV, we constructed recombinant adeno-associated virus (rAAV)-tIK vector system by gene cloning step in which the tIK nucleic acid fragment of SEQ ID NO: 3 was enveloped by inverted terminal repeat (ITR) of AAV so as to transfer the tIK nucleic acid fragment into host cells. We used GFP-expression inducible rAAV viral vector, pSP72-XP7-scAAV2-CMV-GFP, as an expression vector. HA tag sequence (SEQ ID NO: 54) was linked to 5'-end of tIK nucleic acid fragment, and PCR was performed using primers (Forward Primer: SEQ ID NO: 55; and Reverse Primer: SEQ ID NO: 56) which are complementary to both ends of tIK nucleic acid fragment. The ends of the amplified fragment obtained by such processes were cut by restriction enzymes, and the amplified fragment was inserted into the vector so as to prepare tIK-HA-sp72-XP7-scAAV2 recombinant expression vector (AAV2-tIK). After transforming the prepared recombinant expression vector into *E. coli*, it was possible to screen a plasmid with having inserted tIK amplified fragment. The tIK gene conjugated to adeno-associated viral genome was transfected into 293T cells by a transfection process using polyethyleneimine (PEI). The virus, which was certified to express tIK fragment using PEI, was again infected into 293T cells. We certified that tIK was expressed in 293 T cells by Western-blotting assay (See, FIG. 17).

Example 16: Certification of Arthritis Suppression Through AAV-tIK Transfection

We applied the RAAV-tIK prepared in example 15 to in vivo disorder model and certified arthritis treating effect by the expression of the tIK nucleic acid. Each of rAAV2-tIK and rAAV2-GFP viruses (respectively, $1\times10^{11}$ vg/100 μL concentration) was intravenously injected through the tail of spontaneously induced arthritis model IL1RaKO mice. The rAAV2-tIK and rAAV2-GFP viruses were injected every two week, and we monitored the joint states and arthritis incidences in every one week. It was shown that arthritis incidences and arthritis indices were relatively lower in the IL1RaKO mice transfected by rAAV2-tIK compared to the IL1RaKO mice transfected by rAAV2-GFP (See, FIGS. 18A and 18B). We certified that it is likely that transferring IK nucleic acids using viral vector system may result in reducing the arthritis incidences and indices.

Example 17: Construction of tIK Expression System in CHO Cells

Since Chinese hamster ovary (CHO) cells shows high expression efficiencies in case of transfecting genes, they have been widely used as cell lines for preparing gene recombinant protein medicines. In order to certify the expression efficiency of tIK in CHO cells, tIK plasmids (tIK-pcDNA 3.1), which has a HA tag sequence (SEQ ID NO: 54) linked 5'-end of the tIK nucleic acid, were transfected into CHO cells. for the amplification of the tIK gene, a forward primer of SEQ ID NO: 55 and a reveres primer of SEQ ID NO: 56 was used. We certified the expression of tIK in CHO cells by Western blotting assay (See, FIG. 19).

What is claimed is:

1. A method for treating arthritis, the method comprising the step of: administering a pharmaceutically effective amount of at least one fragment of IK factor to a subject having arthritis, wherein the at least one fragment of IK factor comprises a peptide having the amino acid sequence of SEQ ID NO: 4.

2. The method of claim 1, wherein the arthritis comprises rheumatoid arthritis.

3. The method of claim 1, wherein the pharmaceutically effective amount is between 1.0 ng/mL to 10 μg/mL.

* * * * *